(12) United States Patent
Aziz et al.

(10) Patent No.: US 11,724,980 B2
(45) Date of Patent: Aug. 15, 2023

(54) QUINONES HAVING HIGH CAPACITY RETENTION FOR USE AS ELECTROLYTES IN AQUEOUS REDOX FLOW BATTERIES

(71) Applicant: President and Fellows of Harvard College, Cambridge, MA (US)

(72) Inventors: Michael J. Aziz, Cambridge, MA (US); Roy G. Gordon, Cambridge, MA (US); Kaixiang Lin, Cambridge, MA (US); David Gator Kwabi, Somerville, MA (US); Yunlong Ji, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/968,684

(22) PCT Filed: Feb. 11, 2019

(86) PCT No.: PCT/US2019/017479
§ 371 (c)(1),
(2) Date: Aug. 10, 2020

(87) PCT Pub. No.: WO2019/157437
PCT Pub. Date: Aug. 15, 2019

(65) Prior Publication Data
US 2021/0009497 A1 Jan. 14, 2021

Related U.S. Application Data

(60) Provisional application No. 62/740,526, filed on Oct. 3, 2018, provisional application No. 62/628,599, filed on Feb. 9, 2018.

(51) Int. Cl.
*C07C 59/90* (2006.01)
*C07F 9/38* (2006.01)
(Continued)

(52) U.S. Cl.
CPC ............ *C07C 59/90* (2013.01); *C07F 9/3808* (2013.01); *H01M 4/368* (2013.01); *H01M 4/60* (2013.01);
(Continued)

(58) Field of Classification Search
CPC ... C07C 2603/24; C07C 59/90; C07F 9/3808; H01M 2300/0002; H01M 8/08; H01M 8/188

See application file for complete search history.

(56) References Cited

U.S. PATENT DOCUMENTS 3,238,066 A 3/1966 Klass et al.
3,288,641 A 11/1966 Rightmire
(Continued)

FOREIGN PATENT DOCUMENTS

CN 102035007 A 4/2011
CN 103000924 A 3/2013
(Continued)

OTHER PUBLICATIONS

U.S. Appl. No. 14/823,546.
(Continued)

*Primary Examiner* — Sarah A. Slifka
*Assistant Examiner* — Rachel L Zhang
(74) *Attorney, Agent, or Firm* — Clark & Elbing LLP

(57) ABSTRACT

We disclose quinone compounds and related species (Formula I) that possess significant advantages when used as a redox active material in a battery, e.g., a redox flow battery. In particular, the compounds provide redox flow batteries (RFBs) with extremely high capacity retention. For example, RFBs of the invention can be cycled for 500 times with negligible loss of capacity, and such batteries could be employed for years of service. Thus, the invention provides
(Continued)

Symmetric Cell Composition
Negoltye: 5 mL DBEAQ (50% SOC)
Posolyte: 10 mL DBEAQ (50% SOC)
Membrane: Nafion 117

Fuell Cell Composition
Negolyte: 5 mL DBEAQ (0% SOC)
Posolyte: Ferrocyanide (XX% SOC)
Membrane: Fumasep E620K a high efficiency, long cycle life redox flow battery with reasonable power cost, low energy cost, and all the energy scaling advantages of a flow battery.

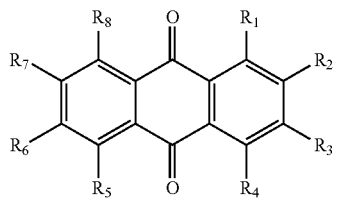

18 Claims, 36 Drawing Sheets

(51) Int. Cl.
H01M 8/18 (2006.01)
H01M 8/08 (2016.01)
H01M 4/36 (2006.01)
H01M 4/60 (2006.01)

(52) U.S. Cl.
CPC ............ H01M 8/08 (2013.01); H01M 8/188 (2013.01); C07C 2603/24 (2017.05); H01M 2300/0002 (2013.01)

(56) References Cited

U.S. PATENT DOCUMENTS

| | | | |
|---|---|---|---|
| 3,300,342 | A | 1/1967 | Klass |
| 4,578,323 | A | 3/1986 | Hertl et al. |
| 4,652,355 | A | 3/1987 | Noding |
| 4,711,828 | A | 12/1987 | Ishida et al. |
| 4,924,015 | A | 5/1990 | Howell et al. |
| 6,020,105 | A | 2/2000 | Wariishi |
| 6,033,784 | A | 3/2000 | Jacobsen et al. |
| 7,056,418 | B2 | 6/2006 | Andoh et al. |
| 8,263,241 | B2 | 9/2012 | Ohtsuka et al. |
| 8,460,814 | B2 | 6/2013 | Deane et al. |
| 8,492,048 | B2 | 7/2013 | Knuckey et al. |
| 8,632,903 | B2 | 1/2014 | Dong et al. |
| 8,722,226 | B2 | 5/2014 | Chiang et al. |
| 8,785,023 | B2 | 7/2014 | Horne et al. |
| 8,906,529 | B2 | 12/2014 | Horne et al. |
| 8,993,183 | B2 | 3/2015 | Pham et al. |
| 9,614,245 | B2 | 4/2017 | Narayan et al. |
| 9,777,299 | B2 | 10/2017 | Amao et al. |
| 9,812,727 | B2 | 11/2017 | Stahl et al. |
| 9,837,679 | B2 | 12/2017 | Reece |
| 9,966,622 | B2 | 5/2018 | Huskinson et al. |
| 10,040,763 | B2 | 8/2018 | Lin et al. |
| 10,153,651 | B2 | 12/2018 | Taylor et al. |
| 10,589,231 | B2 | 3/2020 | Brozell |
| 10,840,532 | B2 | 11/2020 | Chen et al. |
| 10,847,829 | B2 | 11/2020 | Huskinson et al. |
| 2002/0088576 | A1 | 7/2002 | Andoh et al. |
| 2006/0194151 | A1 | 8/2006 | Inagaki et al. |
| 2007/0134520 | A1 | 6/2007 | Shimomura et al. |
| 2007/0184309 | A1 | 8/2007 | Gust, Jr. et al. |
| 2009/0017379 | A1 | 1/2009 | Inatomi et al. |
| 2009/0094822 | A1 | 4/2009 | Ohtsuka et al. |
| 2010/0112393 | A1 | 5/2010 | Knuckey et al. |
| 2011/0027624 | A1 | 2/2011 | Deane et al. |
| 2011/0045332 | A1 | 2/2011 | Horne et al. |
| 2011/0189520 | A1 | 8/2011 | Carter et al. |
| 2011/0223450 | A1 | 9/2011 | Horne et al. |
| 2011/0284456 | A1 | 11/2011 | Brozell |
| 2013/0157162 | A1 | 6/2013 | Dong et al. |
| 2014/0186731 | A1 | 7/2014 | Pham et al. |
| 2014/0370403 | A1 | 12/2014 | Narayan et al. |
| 2015/0079497 | A1 | 3/2015 | Lavastre et al. |
| 2015/0104724 | A1 | 4/2015 | Chang et al. |
| 2015/0176037 | A1 | 6/2015 | Amao et al. |
| 2015/0207165 | A1 | 7/2015 | Schubert et al. |
| 2015/0243991 | A1 | 8/2015 | Huskinson et al. |
| 2016/0043423 | A1 | 2/2016 | Huskinson et al. |
| 2016/0105042 | A1 | 4/2016 | Taylor et al. |
| 2016/0229803 | A1 | 8/2016 | Lin et al. |
| 2016/0248114 | A1* | 8/2016 | Huskinson ......... B29C 48/2528 |
| 2017/0047592 | A1* | 2/2017 | Surendranath ........ C07F 15/006 |
| 2017/0279148 | A1 | 9/2017 | Stahl et al. |
| 2017/0291916 | A1 | 10/2017 | Millard |
| 2018/0048011 | A1 | 2/2018 | Aziz et al. |
| 2018/0219241 | A1 | 8/2018 | Chen et al. |
| 2018/0241107 | A1 | 8/2018 | Su et al. |
| 2020/0373599 | A1 | 11/2020 | Gordon et al. |
| 2021/0083311 | A1 | 3/2021 | Huskinson et al. |

FOREIGN PATENT DOCUMENTS

| | | |
|---|---|---|
| CN | 104882624 A | 9/2015 |
| CN | 105308785 A | 2/2016 |
| EP | 0298034 A2 | 1/1989 |
| EP | 0911893 A1 | 4/1999 |
| EP | 2772494 A1 | 9/2014 |
| EP | 2901520 A2 | 8/2015 |
| EP | 2901520 A4 | 11/2016 |
| JP | S5028645 A | 3/1975 |
| JP | S6273577 A | 4/1987 |
| JP | H0419966 A | 1/1992 |
| JP | 0758625 B2 | 6/1995 |
| JP | H08185868 A | 7/1996 |
| JP | H11126610 A | 5/1999 |
| JP | 2002-100398 A | 4/2002 |
| KR | 20100040606 A | 4/2010 |
| WO | WO-2006/129635 A1 | 12/2006 |
| WO | WO-2011/131959 A1 | 10/2011 |
| WO | WO-2014/052682 A2 | 4/2014 |
| WO | WO-2014/052682 A3 | 4/2014 |
| WO | WO-2014/204985 A1 | 12/2014 |
| WO | WO-2015/048550 A1 | 4/2015 |
| WO | WO-2016/144909 A1 | 9/2016 |
| WO | WO-2016/156451 A1 | 10/2016 |
| WO | WO-2018/032003 A1 | 2/2018 |
| WO | WO-2018/146343 A1 | 8/2018 |
| WO | WO-2018/146344 A1 | 8/2018 |
| WO | WO-2020/072406 A2 | 4/2020 |

OTHER PUBLICATIONS

U.S. Appl. No. 15/025,040, Huskinson et al..
U.S. Appl. No. 15/556,140, Aziz et al..
U.S. Appl. No. 16/324,951, Gordon et al..
Alt et al., "Evaluation of organic battery electrodes: voltammetric study of the redox behaviour of solid quinones," J Appl Electrochem. 2(3):193-200 (1972).
Beh et al., "A Neutral pH Aqueous Organic-Organometallic Redox Flow Battery with Extremely High Capacity Retention," ACS Energy Lett. 2(3):639-44 (2017).
Bird et al., "Electrochemistry of the viologens," Chem Soc Rev. 10:49-82 (1981).
Borisova et al., "Simple Preparative Synthesis of Spinochrome E, a Pigment from Sea Urchins of the Genus *Echinothrix*," Chem Nat Comp. 48(2):202-4 (2012).
Chen et al., "A quinone-bromide flow battery with 1 W/cm2 power density," published in final form as: J Electrochem Soc. 163(1):A5010-3 (2016) (9 pages) (author manuscript).
Conant et al., "Free and total energy changes in the reduction of quinones," J Am Chem Soc. 44(11):2480-93 (1922).
Conant et al., "Reduction potentials of quinones. I. The effect of the solvent on the potentials of certain benzoquinones," J Am Chem Soc. 45(9):2194-218 (1923).
Conant et al., "Reduction potentials of quinones. II. The potentials of certain derivatives of benzoquinone, naphthoquinone and anthraquinone," J Am Chem Soc. 46(8):1858-1881 (1924).

(56) References Cited

OTHER PUBLICATIONS

Costentin et al., "Electrochemical approach to the mechanistic study of proton-coupled electron transfer," Chem Rev. 108(7):2145-79 (2008).
Diaz, "Analytical applications of 1,10-anthraquinones: A review," Talanta. 38(6):571-88 (1991).
EMD Millipore Corporation "Pyridinium chloride for synthesis—Material Safety Data Sheet," revised Aug. 22, 2013 (9 pages).
Er et al., "Computational design of molecules for an all-quinone redox flow battery," Chem Sci. 6(2):885-93 (2015) (10 pages).
Gerhardt et al., "Anthraquinone derivatives in aqueous flow batteries," Adv Energy Mater. 7(8):1601488 (2017) (9 pages).
Goulet et al., "Flow battery molecular reactant stability determined by symmetric cell cycling methods," J Electrochem Soc. 165(7):A1466-77 (2018) (23 pages).
Hori, Chapter 3: Electrochemical CO2 reduction on metal electrodes. *Modern aspects of electrochemistry.* C. Vayenas et al., 89-189 (2008).
Hull et al., "Reversible hydrogen storage using CO2 and a proton-switchable iridium catalyst in aqueous media under mild temperatures and pressures," Nat Chem. 4(5):383-8 (2012).
Hunyh et al., "Quinone 1 e- and 2 e-/2 H+ reduction potentials: identification and analysis of deviations from systematic scaling relationships," J Am Chem Soc. 138(49):15903-10 (2016) (23 pages).
Huskinson et al., "A high power density, high efficiency hydrogen-chlorine regenerative fuel cell with a low precious metal content catalyst," Energy Environ Sci. 5(9):8690-98 (2012).
Huskinson et al., "A metal-free organic-inorganic aqueous flow battery," Nature. 505(7482):195-8 (2014) (16 pages).
Huskinson et al., "Cycling of a quinone-bromide flow battery for large-scale electrochemical energy storage," published in final form as: ECS Trans. 61(37):27-30 (2014) (4 pages) (author manuscript).
Huskinson et al., "Novel quinone-based couples for flow batteries," published in final form as: ECS Trans. 53(7):101-5 (2013) (5 pages) (author manuscript).
International Search Report and Written Opinion for International Application No. PCT/US2019/017479, dated May 28, 2019 (18 pages).
Khatee et al., "Differential pH as a method for increasing cell potential in organic aqueous flow batteries," J Mater Chem A. 5(41):21875-82 (2017).
Knox et al., "134. Ferrocene derivatives. Part VII. Some sulphur derivatives," J Chem Soc. 692-96 (1958).
Krishnan et al., "Reduction potentials for 2,2'-bipyridine and 1,10-phenanthroline couples in aqueous solutions," J Am Chem Soc. 105(17):5617-23 (1983).
Kwabi et al., "Alkaline quinone flow battery with long lifetime at pH 12," Joule. 2:1894-1906 (2018) (14 pages).
Li et al., "$CO_2$ reduction at low overpotential on Cu electrodes resulting from the reduction of thick Cu2O films," J Am Chem Soc. 134(17):7231-4 (2012).
Lin et al., "A redox-flow battery with an alloxazine-based organic electrolyte," Nature Energy. 1(9):16102 (2016) (38 pages).
Lin et al., "Alkaline quinone flow battery," Science. 349(6255):1529-32 (2015) (28 pages).
Liu et al., "A Total Organic Aqueous Redox Flow Battery Employing a Low Cost and Sustainable Methyl Viologen Anolyte and 4-HO-TEMPO Catholyte," Adv Energy Mater. 6(3):1501449 (2016).
Mortimer et al., "Electrochemic materials," Chem Soc Rev. 26(3):147-56 (1997).
National Center for Biotechnology Information. "PubChem substance record for SID 234866994, SCHEMBL9466422, source: SureChEMBL." PubChem, <https://pubchem.ncbi.nlm.nih.gov/substance/234866994>, Accessed Dec. 2, 2020 (7 pages).
Nawar et al., "Benzoquinone-hydroquinone couple for flow battery," published in final form as: MRS Proceedings. 1491:mrsf12-1491 (2013) (6 pages) (author manuscript).
Nielson et al., "Electron Self-Exchange Kinetics for a Water-Soluble Ferrocenium/Ferrocene Couple: Rate Modulation via Charge Dependent Calix[6]arene-p-sulfonate Encapsulation," Inorg Chem. 35(5):1402-4 (1996).
Pubchem, Substance Record for SID 142148551, <https://pubchem.ncbi.nlm.nih.gov/substance/142148551#section=Top>, available date Aug. 20, 2012, retrieved Jun. 20, 2016 (6 pages).
Quan et al., "Voltammetry of quinones in unbuffered aqueous solution: reassessing the roles of proton transfer and hydrogen bonding in the aqueous electrochemistry of quinones," J Am Chem Soc. 129(42):12847-56 (2007).
Rasmussen, "A single substance organic redox flow battery," ESS, 2012 (Poster presentation).
Rieger et al., "Methyl viologen reactions. 5. Rates and mechanism of cation-radical formation in aqueous base," J Org Chem. 53(7):1481-85 (1988).
Smith et al., "The pH-Rate Profile for the Hydrolysis of a Peptide Bond," J Am Chem Soc. 120(35):8910-13 (1998).
Wang et al., "Anthraquinone with tailored structure for a nonaqueous metal-organic redox flow battery," Chem Commun (Camb). 48(53):6669-71 (2012).
Weber et al., "Redox flow batteries: a review," J Appl Electrochem 41:1137-64 (2011).
Xu et al., "A study of tiron in aqueous solutions for redox flow battery application," Electrochimica Acta. 55:715-20 (2010).
Xu et al., "Novel organic redox flow batteries using soluble quinonoid compounds as positive materials," IEEE. (4 pages) (2009).
Yang et al., "High-performance aqueous organic flow battery with quinone-based redox couples at both electrodes," J Electrochem Soc. 163(7):A1442-49 (2016).
Yao et al., "High-capacity organic positive-electrode material based on a benzoquinone derivative for use in rechargeable lithium batteries," J Power Sources. 195(24): 8336-40 (2010).
Lin et al., "Alkaline quinone flow battery," published in final edited form as: Science. 349(6255):1529-32 (2015) (27 pages).
Tao et al., "Anticancer Effect and Structure-Activity Analysis of Marine Products Isolated from Metabolites of Mangrove Fungi in the South China Sea," Mar Drugs. 8(4):1094-105 (2010).
Comninellis et al., "The electrochemical reduction of anthraquinone to anthrone in concentrated $H_2SO_4$," Journal of Applied Electrochemistry. 15(5):771-3 (1985) (Sep. 1985).
Jing et al., "Anthraquinone Flow Battery Reactants with Nonhydrolyzable Water-Solubilizing Chains Introduced via a Generic Cross-Coupling Method," ACS Energy Lett. 7(1):226-235 (includes supporting information) (Dec. 14, 2021) (44 pages).
Kerr et al., "High Energy Density Aqueous Flow Battery Utilizing Extremely Stable, Branching-Induced High-Solubility Anthraquinone near Neutral pH," ACS Energy Lett. 8(1):600-7 (includes supporting information) (Dec. 20, 2022) (54 pages).
Shi et al., "1,1',8,8'-Tetramethoxy-10,10'-bianthrone," Acta Cryst. 60:o2275-o2277 (2004) (Dec. 2004) (7 pages).
Tabor et al., "Supplementary Material to 'Theoretical and Experimental Investigation of the Stability Limits of Quinones in Aqueous Media: Implications for Organic Aqueous Redox Flow Batteries,'" ChemRxiv. DOI: 10.26434/chemrxiv.6990053.v2 (2018) (Aug. 22, 2018) (19 pages).
Wendlandt, Chapter 14: Quinones in Hydrogen Peroxide Synthesis and Catalytic Aerobic Oxidation Reactions. *Liquid Phase Aerobic Oxidation Catalysis: Industrial Applications and Academic Perspectives, First Edition.* Wiley-VCH Verlag GmbH & Co. KGaA., 221-237 (2016) (Aug. 17, 2016).
Wu et al., "Extremely Stable Anthraquinone Negolytes Synthesized from Common Precursors," Chem. 6(6):1432-1442 (includes supporting information) (Jun. 11, 2020) (33 pages).

* cited by examiner

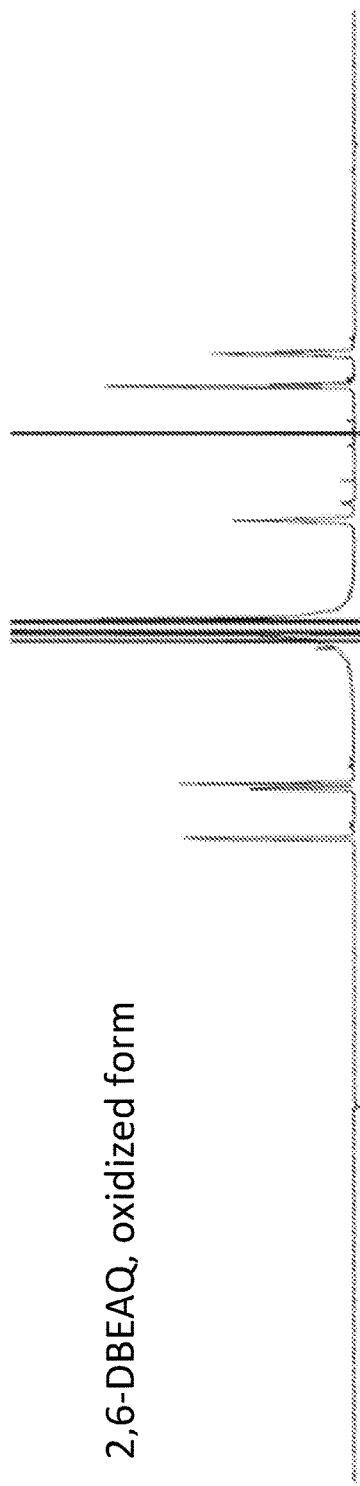
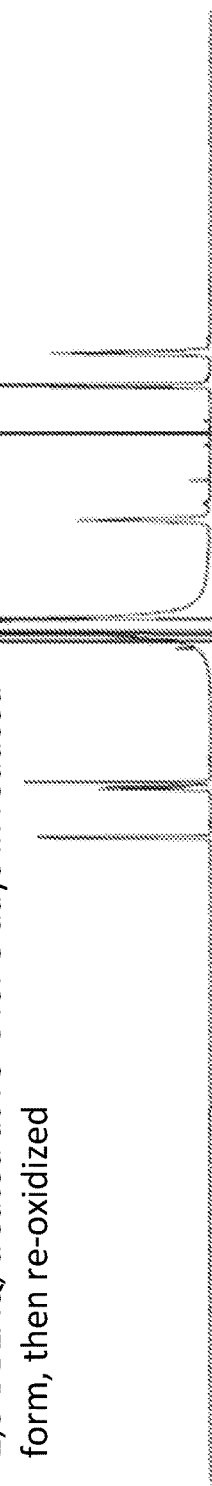
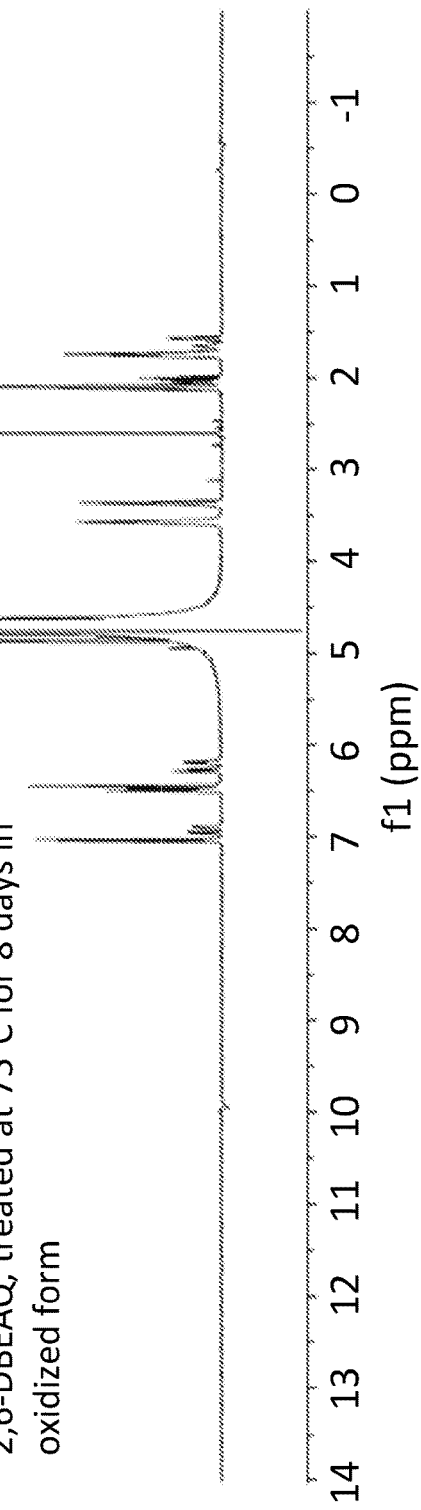
FIG. 10A  2,6-DBEAQ, oxidized form
FIG. 10B  2,6-DBEAQ, treated at 75°C for 8 days in reduced form, then re-oxidized
FIG. 10C  2,6-DBEAQ, treated at 75°C for 8 days in oxidized form

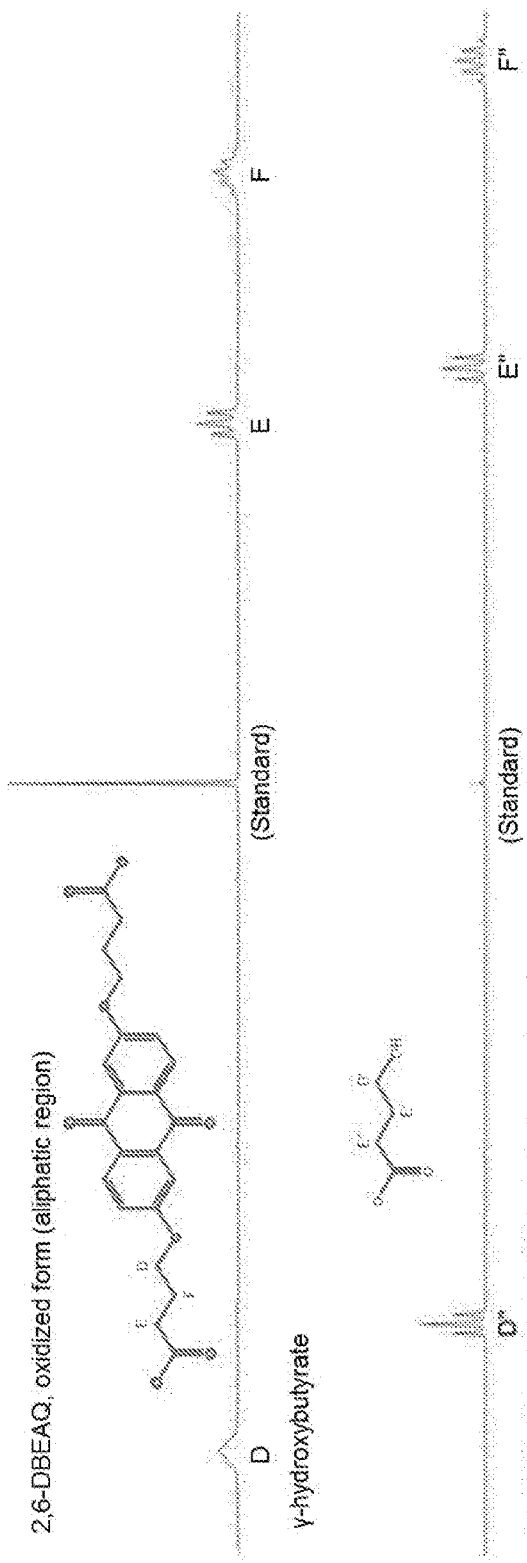
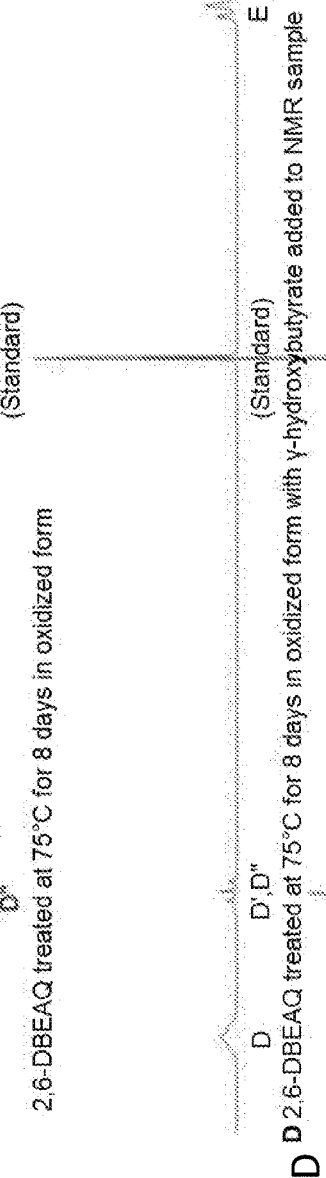
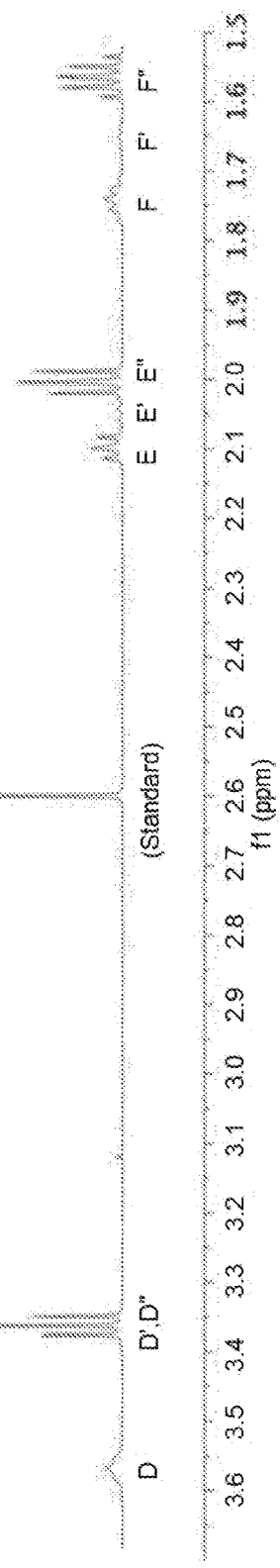
FIG. 11A  2,6-DBEAQ, oxidized form (aliphatic region)
FIG. 11B  γ-hydroxybutyrate
FIG. 11C  2,6-DBEAQ treated at 75°C for 8 days in oxidized form
FIG. 11D  2,6-DBEAQ treated at 75°C for 8 days in oxidized form with γ-hydroxybutyrate added to NMR sample

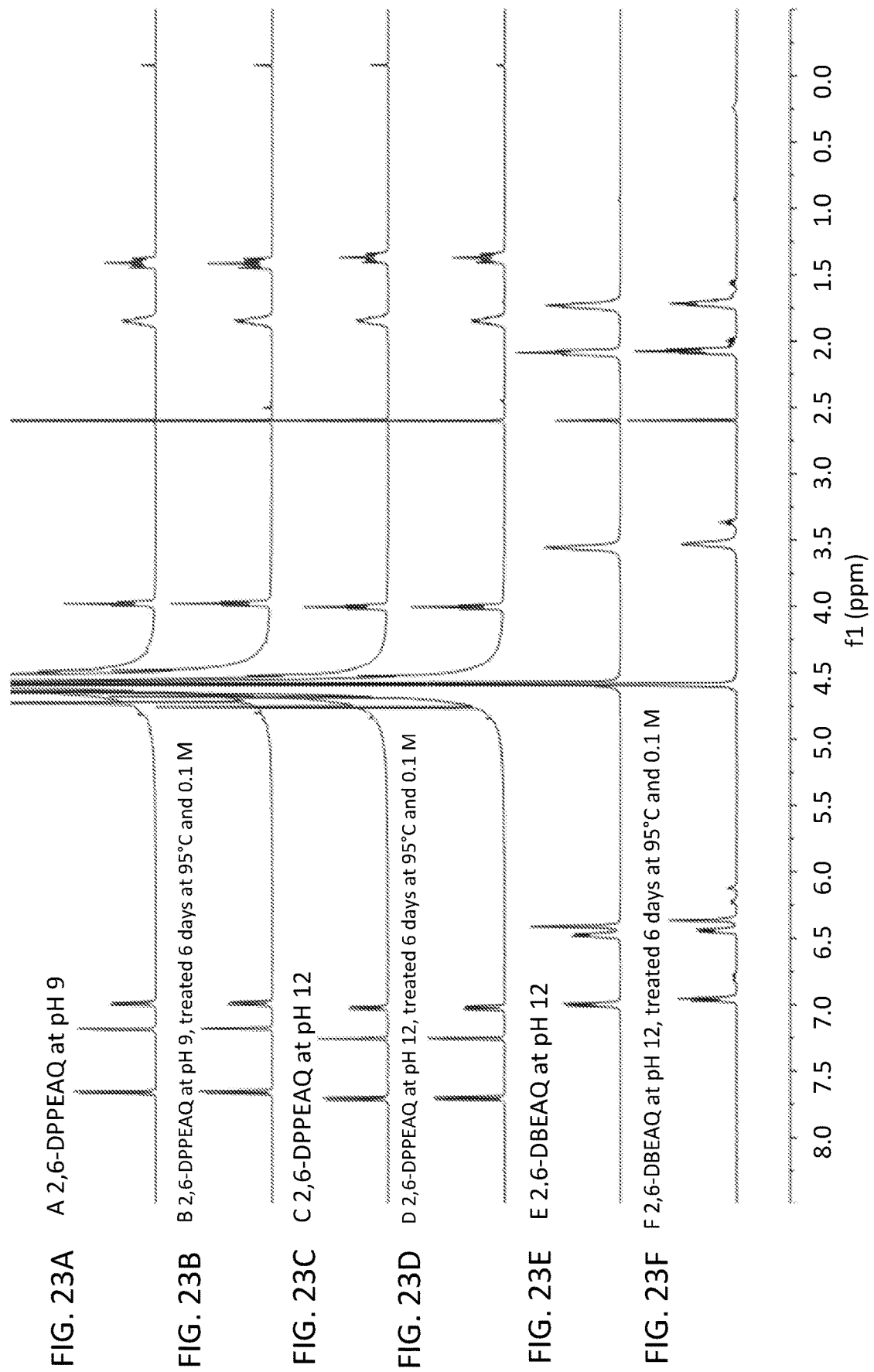
FIG. 23A  A 2,6-DPPEAQ at pH 9
FIG. 23B  B 2,6-DPPEAQ at pH 9, treated 6 days at 95°C and 0.1 M
FIG. 23C  C 2,6-DPPEAQ at pH 12
FIG. 23D  D 2,6-DPPEAQ at pH 12, treated 6 days at 95°C and 0.1 M
FIG. 23E  E 2,6-DBEAQ at pH 12
FIG. 23F  F 2,6-DBEAQ at pH 12, treated 6 days at 95°C and 0.1 M

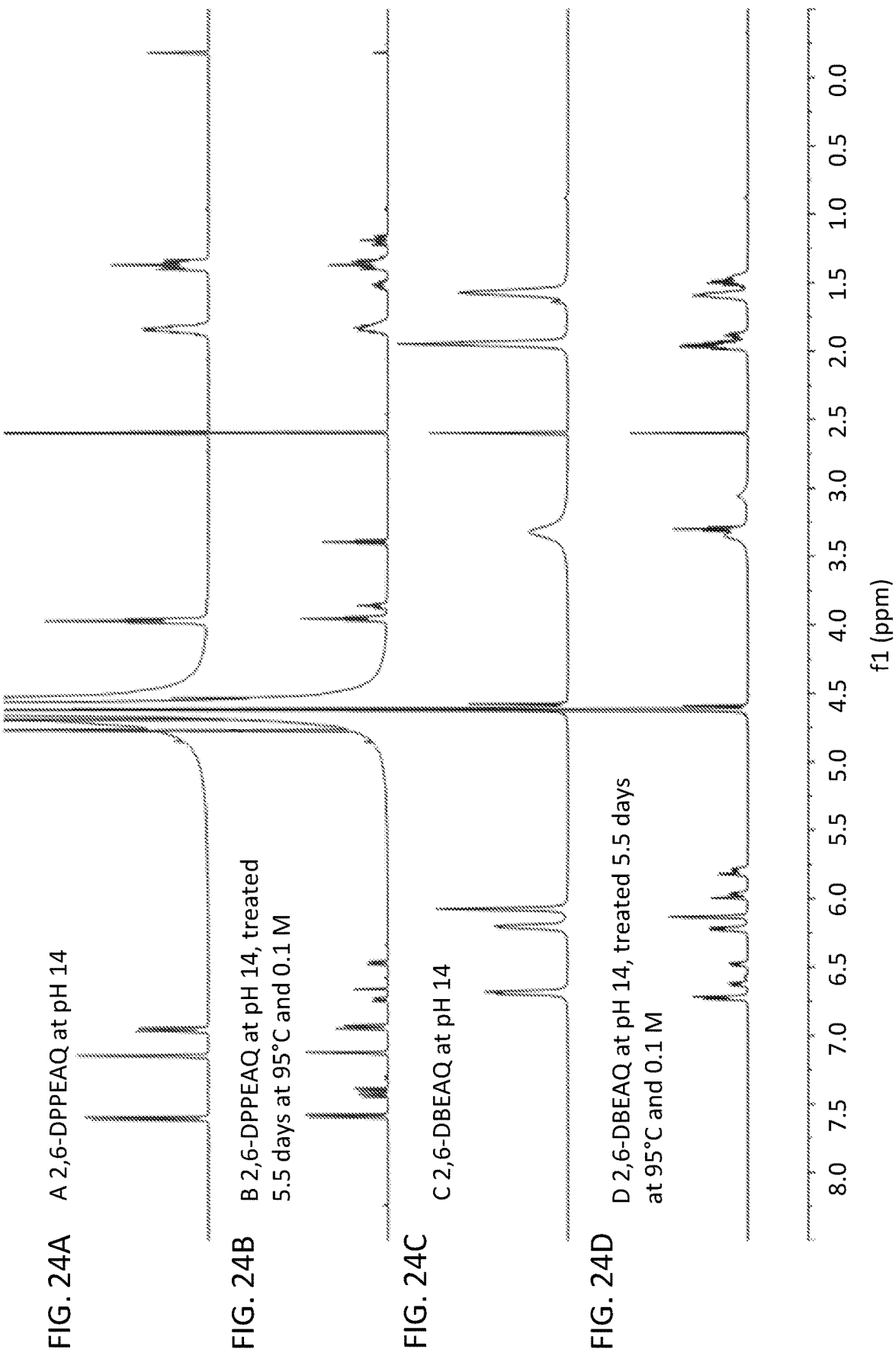

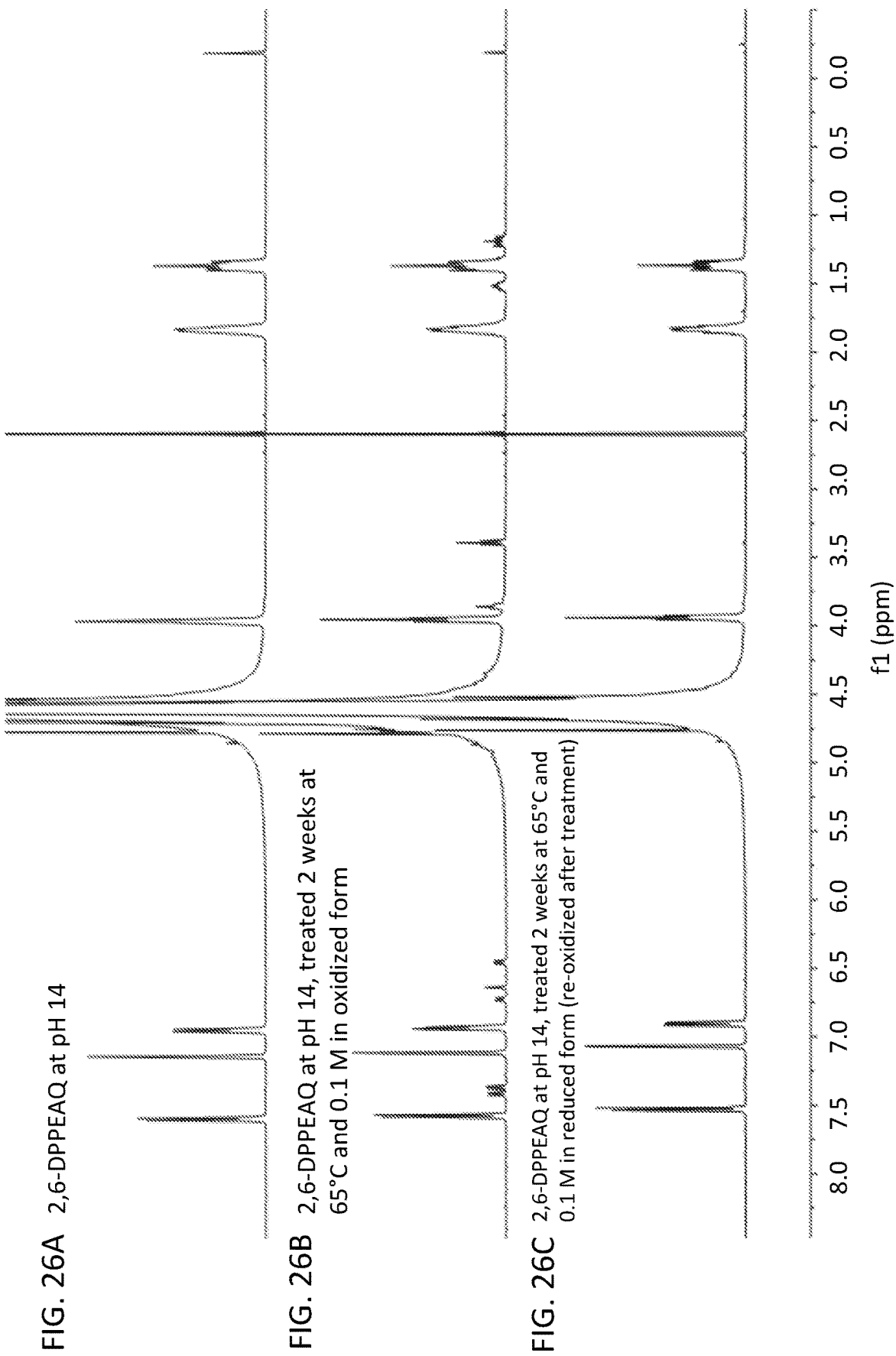
FIG. 26A 2,6-DPPEAQ at pH 14
FIG. 26B 2,6-DPPEAQ at pH 14, treated 2 weeks at 65°C and 0.1 M in oxidized form
FIG. 26C 2,6-DPPEAQ at pH 14, treated 2 weeks at 65°C and 0.1 M in reduced form (re-oxidized after treatment)

QUINONES HAVING HIGH CAPACITY RETENTION FOR USE AS ELECTROLYTES IN AQUEOUS REDOX FLOW BATTERIES

STATEMENT REGARDING FEDERALLY SPONSORED RESEARCH

This invention was made with government support under DE-AC05-76RL01830, DE-AR0000348, and DE-AR0000767 awarded by the U.S. Department of Energy and under 1509041 awarded by the National Science Foundation. The government has certain rights to the invention.

TECHNICAL FIELD

This invention relates generally to energy storage. More specifically, the invention relates to a new class of compounds and their operation in a redox flow battery. The compounds are composed only of earth-abundant elements, having high electrochemical stability and high water solubility.

BACKGROUND OF THE INVENTION

Redox flow batteries (RFBs) represent a class of energy storage devices that are especially suited for large-scale stationary deployment. The cost of RFB electrolytes, which are the charge-storing materials, usually constitutes a large proportion of the cost of a complete RFB system. For other system components, large cost savings are realized by utilizing water as the solvent for the electrolytes and carbon for the electrodes. Long term stability of the electrolytes is also important to the commercial success of the battery.

Accordingly, there is a need for new redox active species having long term stability for use in RFBs.

SUMMARY OF THE INVENTION

The invention features redox flow batteries and compounds useful therein as negolytes or posolytes. The batteries and compounds are advantageous in terms of being useable in water solutions at neutral pH and have extremely high capacity retention. Flow batteries based on these materials can store large amounts of energy. Because of the non-hazardous nature of these compounds, this method of energy storage is safe for use in the large-scale electrical grid or for smaller-scale use in buildings. Flow batteries have scaling advantages over solid electrode batteries for large scale energy storage. Batteries based on quinones can have high current density, high efficiency, and long lifetime in a flow battery. High current density drives down power-related costs. The other advantages this particular technology has over other flow batteries include inexpensive chemicals, energy storage in the form of safer liquids, an inexpensive separator, little or no precious metals usage in the electrodes, and other components made of plastic or inexpensive metals with coatings proven to afford corrosion protection.

In one aspect, the invention features, a redox flow battery including a first aqueous electrolyte comprising a first redox active material; and a second aqueous electrolyte comprising a second redox active material that is a compound of formula I:

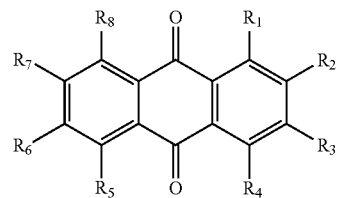

or an ion, salt, or hydroquinone thereof, wherein each of $R_1$-$R_8$ is independently H; halo; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo; $-NO_2$; $-OR_a$; $-N(R_a)_2$; $-C(=O)R_a$; $-C(=O)OR_a$; $-S(=O)_2R_a$; $-S(=O)_2OR_a$; $-OS(=O)_2OR_a$; $-P(=O)R_{a2}$; $-P(=O)(OR_a)_2$; and $-OP(=O)(OR_a)_2$; $-X_1$-$L_1$-C(O)O$-Y_1$; $-X_2$-$L_2$-C(O)O$-Y_2$; $-X_3$-$L_3$-P(=O)(OY_3)_2$; or $-X_4$-$L_4$-P(=O)(OY_4)_2$; wherein each $R_a$ is independently H; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; or optionally substituted $C_{1-9}$ heteroaryl having one to four heteroatoms independently selected from O, N, and S;

$X_1$, $X_2$, $X_3$, and $X_4$ are independently O, S, or $CH_2$; $L_1$, $L_2$, $L_3$, and $L_4$ are independently $C_1$-$C_6$ alkylene; and $Y_1$, $Y_2$, $Y_3$, and $Y_4$ are independently H or optionally substituted $C_1$-$C_6$ alkyl, provided that one and only one of $R_1$-$R_8$ is $-X_1$-$L_1$-C(O)O$-Y_1$ or $-X_3$-$L_3$-P(=O)(OY_3)_2$ and one and only one of $R_1$-$R_8$ is $-X_2$-$L_2$-C(O)O$-Y_2$ or $-X_4$-$L_4$-P(=O)(OY_4)_2$.

In certain embodiments, $X_1$ and $X_2$ are O. In other embodiments, each of $R_1$-$R_8$ is independently H; halo; optionally substituted $C_{1-6}$ alkyl; $-X_1$-$L_1$-C(O)O$-Y_1$; or $-X_2$-$L_2$-C(O)O$-Y_2$. In further embodiments, $R_2$ is $-X_1$-$L_1$-C(O)O$-Y_1$, and $R_6$ is $-X_2$-$L_2$-C(O)O$-Y_2$. In yet other embodiments, $Y_1$ and $Y_2$ are H.

In certain embodiments, $X_3$ and $X_4$ are O. In other embodiments, each of $R_1$-$R_8$ is independently H; halo; optionally substituted $C_{1-6}$ alkyl; $-X_3$-$L_3$-P(=O)(OY_3)_2$; or $-X_4$-$L_4$-P(=O)(OY_4)_2$. In further embodiments, $R_2$ is $-X_3$-$L_3$-P(=O)(OY_3)_2$, and $R_6$ $-X_4$-$L_4$-P(=O)(OY_4)_2$. In yet other embodiments, $Y_3$ and $Y_4$ are H.

Exemplary quinones are

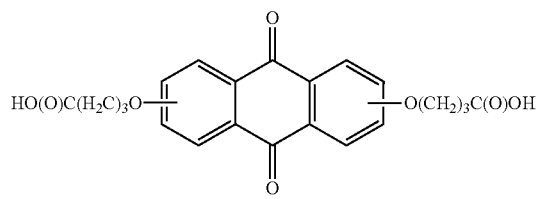

or an ion, salt, or hydroquinone thereof; or

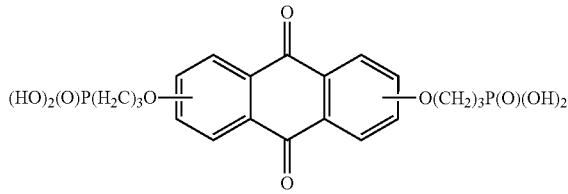

or an ion, salt, or hydroquinone thereof.

For example, the quinone is

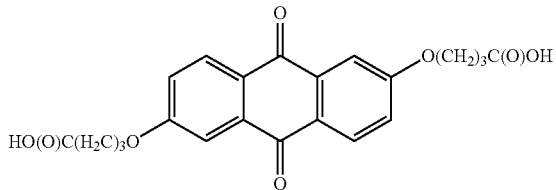

or an ion, salt, or hydroquinone thereof, or the quinone is

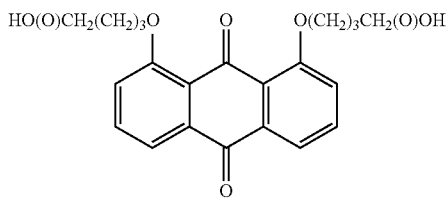

or an ion, salt, or hydroquinone thereof, or the quinone is

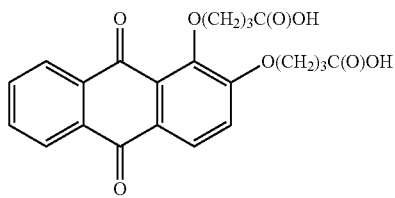

or an ion, salt, or hydroquinone thereof.

In certain embodiments, the quinone is

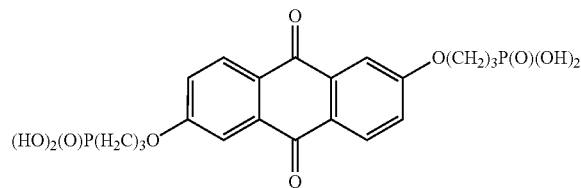

or an ion, salt, or hydroquinone thereof.

In further embodiments, the second redox active material is the hydroquinone of formula I, which is oxidized to the corresponding quinone during discharge. The pH of the second aqueous electrolyte is, for example, ≥7. In particular embodiments, the pH is from 8-13. The first redox active material may include bromine, chlorine, iodine, oxygen, vanadium, chromium, cobalt, iron, aluminum, manganese, cobalt, nickel, copper, or lead.

In a related aspect, the invention features a compound of formula I:

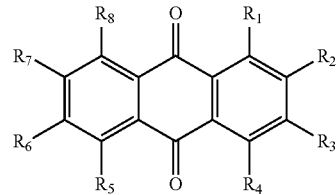

or an ion, salt, or hydroquinone thereof,
wherein each of $R_1$-$R_8$ is independently H; halo; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo; —$NO_2$; —$OR_a$; —$N(R_a)_2$; —$C(=O)R_a$; —$C(=O)OR_a$; —$S(=O)_2R_a$; —$S(=O)_2OR_a$; —$OS(=O)_2R_a$; —$P(=O)R_{a2}$; —$P(=O)(OR_a)_2$; —$OP(=O)(OR_a)_2$; —$X_1$-$L_1$-$C(O)O$—$Y_1$; —$X_2$-$L_2$-$C(O)O$—$Y_2$; —$X_3$-$L_3$-$P(=O)(OY_3)_2$; or —$X_4$-$L_4$-$P(=O)(OY_4)_2$; wherein each $R_a$ is independently H; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; or optionally substituted $C_{1-9}$ heteroaryl having one to four heteroatoms independently selected from O, N, and S;
$X_1$, $X_2$, $X_3$, and $X_4$ are independently O, S, or $CH_2$; $L_1$, $L_2$, $L_3$, and $L_4$ are independently $C_1$-$C_6$ alkylene; and $Y_1$, $Y_2$, $Y_3$, and $Y_4$ are independently H or optionally substituted $C_1$-$C_6$ alkyl, provided that one and only one of $R_1$-$R_8$ is —$X_1$-$L_1$-$C(O)O$—$Y_1$ or —$X_3$-$L_3$-$P(=O)(OY_3)_2$ and one and only one of $R_1$-$R_8$ is —$X_2$-$L_2$-$C(O)O$—$Y_2$ or —$X_4$-$L_4$-$P(=O)(OY_4)_2$.

In certain embodiments, when $R_2$-$R_4$ and $R_6$-$R_8$ are H, $R_1$ and $R_5$ are not both —$SCH_2C(O)OH$, —$OCH_2C(O)OH$, or —$OCH_2C(O)OCH_2CH_3$; when $R_4$ and $R_8$ are H and $R_2$, $R_3$, $R_6$, and $R_7$ are —$O(CH_2)_3(CH_3)$, $R_1$ and $R_5$ are not both —$O(CH_2)_3C(O)OH$; when $R_4$ and $R_8$ are H and $R_2$, $R_3$, $R_6$, and $R_7$ are —$O(CH_2)_4(CH_3)$, $R_1$ and $R_5$ are not both —$O(CH_2)_4C(O)OH$; when $R_1$ and $R_8$ are OH and $R_3$-$R_6$ are H, $R_2$ and $R_7$ are not both —$(CH_2)_3C(O)OH$ or —$(CH_2)_3C(O)OCH_3$; when $R_1$, $R_4$, $R_5$, and $R_8$ are $NH_2$ and $R_3$ and $R_6$ are H, $R_2$ and $R_7$ are not both —$O(CH_2)_3C(O)O(CH_2)_4CH_3$; when $R_1$, $R_3$-$R_5$, $R_7$, and $R_8$ are H, $R_2$ and $R_6$ are not both —$OCH(CH_3)C(O)OCH_3$, —$OCH(CH_3)C(O)OH$, or —$OCH_2C(O)OCH_3$; when $R_1$, $R_3$, $R_5$, and $R_7$ are H, and $R_4$ and $R_8$ are —$N(R_a)_2$, $R_2$ and $R_6$ are not both —$S(CH_2)_nC(O)OCH_2CH_3$, wherein n is 1 to 5; when $R_1$ and $R_4$ are $OCH_3$, and $R_5$-$R_8$ are H, $R_2$ and $R_3$ are not both —$CH_2CH_2C(O)OH$, —$CH_2CH_2C(O)OCH_3$, or —$CH_2CH(C(O)CH_3)C(O)OCH_2CH_3$; when $R_1$ and $R_4$ are OH, and $R_5$-$R_8$ are H, $R_2$ and $R_3$ are not both —$CH_2CH_2C(O)OCH_3$; when $R_1$ and $R_4$-$R_8$ are H, $R_2$ and $R_3$ are not both —$CH_2C(NHC(O)CH_3)(C(O)OCH_2CH_3)_2$ or —$CH_2CH(NHC(O)CH_3)C(O)OCH_2CH_3$; when $R_2$-$R_7$ are H, $R_1$ and $R_8$ are not both —$OCH_2C(O)OCH_2CH_3$ or —$SCH_2CH_2C(O)OH$; when $R_2$ and $R_4$-$R_7$ are H and $R_3$ is —$CH_3$, $R_1$ and $R_8$ are not both —$OCH_2C(O)OCH_2CH_3$; when $R_2$, $R_3$, $R_6$, and $R_7$ are H and $R_4$ and $R_5$ are —$N(R_a)_2$, $R_1$ and $R_8$ are not both —$OCH_2C(O)OCH_2CH_3$ or —$OCH_2C(O)OH$; when $R_2$-$R_4$, $R_7$, and $R_8$ are H and $R_5$ is $NH_2$, $R_1$ and $R_6$ are not both —$SCH_2C(O)$ OH; when $R_2$-$R_6$ are H and $R_8$ is $NH_2$, $R_1$ and $R_7$ are not both —$SCH_2C(O)OH$; when $R_3$-$R_8$ are H, $R_1$ and $R_2$ are not both —$OC(O)CH_2CH_2C(O)O$ $CH_2CH_3$; when $R_1$, $R_3$-$R_5$, $R_7$, and $R_8$ are H, $R_2$ and $R_6$ are not both —$OC(O)CH_2CH_2C(O)O$ $CH_2CH_3$; when $R_2$, $R_3$, and $R_5$-$R_8$ are H, $R_1$ and $R_4$ are not both —$OC(O)CH_2CH_2C(O)OCH_2CH_3$ or —$SCH_2C(O)OH$; when $R_2$-$R_7$ are H, $R_1$ and $R_8$ are not both —$OC(O)CH_2CH_2C(O)OCH_2CH_3$; when $R_2$, $R_3$, $R_6$, and $R_7$ are H and $R_4$ and $R_5$ are —$(CH_2)_5CH_3$, $R_1$ and $R_8$ are not both —$(CH_2)_7C(O)OH$; when $R_2$, $R_3$, $R_6$, and $R_7$ are H and $R_4$ and $R_8$ are —$(CH_2)_5CH_3$, $R_1$ and $R_5$ are not both —$(CH_2)_7C(O)OH$; and/or when $R_3$ and $R_6$ are H and $R_1$, $R_4$, $R_5$, and $R_8$ are —$NH_2$, $R_2$ and $R7_5$ are not both —$O(CH_2)_3C(O)OCH_3$.

In certain embodiments, $X_1$ and $X_2$ are O. In other embodiments, each of $R_1$-$R_8$ is independently H; halo; optionally substituted $C_{1-6}$ alkyl; —$X_1$-$L_1$-C(O)O—$Y_1$; or —$X_2$-$L_2$-C(O)O—$Y_2$. In further embodiments, $R_2$ is —$X_1$-$L_1$-C(O)O—$Y_1$, and $R_6$ is —$X_2$-$L_2$-C(O)O—$Y_2$. In yet other embodiments, $Y_1$ and $Y_2$ are H.

In certain embodiments, $X_3$ and $X_4$ are O. In other embodiments, each of $R_1$-$R_8$ is independently H; halo; optionally substituted $C_{1-6}$ alkyl; —$X_3$-$L_3$-P(=O)(O$Y_3$)$_2$; or —$X_4$-$L_4$-P(=O)(O$Y_4$)$_2$. In further embodiments, $R_2$ is —$X_3$-$L_3$-P(=O)(O$Y_3$)$_2$, and $R_6$ is —$X_4$-$L_4$-P(=O)(O$Y_4$)$_2$. In yet other embodiments, $Y_3$ and $Y_4$ are H.

Exemplary compounds are

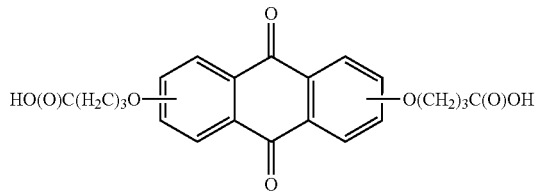

or an ion, salt, or hydroquinone thereof, or

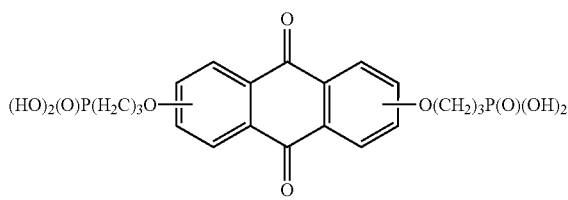

or an ion, salt, or hydroquinone thereof.

For example, the compound is

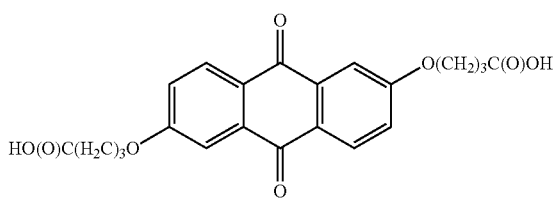

or an ion, salt, or hydroquinone thereof, or the compound is

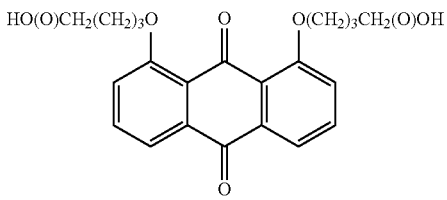

or an ion, salt, or hydroquinone thereof, or the compound is

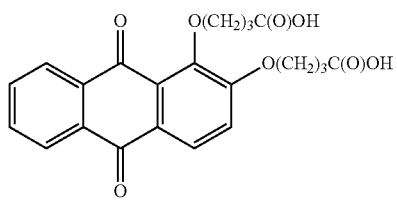

or an ion, salt, or hydroquinone thereof.

In certain embodiments, the compound is

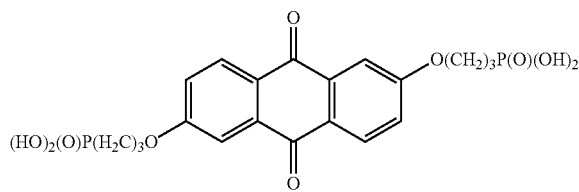

or an ion, salt, or hydroquinone thereof.

By "alkyl" is meant straight chain or branched saturated groups from 1 to 6 carbons. Alkyl groups are exemplified by methyl, ethyl, n- and iso-propyl, n-, sec-, iso- and tert-butyl, neopentyl, and the like, and may be optionally substituted with one or more, substituents.

By "aryl" is meant an aromatic cyclic group in which the ring atoms are all carbon. Exemplary aryl groups include phenyl, naphthyl, and anthracenyl. Aryl groups may be optionally substituted with one or more substituents.

By "carbocyclyl" is meant a non-aromatic cyclic group in which the ring atoms are all carbon. Exemplary carbocyclyl groups include cyclopropyl, cyclobutyl, cyclopentyl, cyclohexyl, cycloheptyl, and cyclooctyl. Carbocyclyl groups may be optionally substituted with one or more substituents.

By "halo" is meant, fluoro, chloro, bromo, or iodo.

By "heteroaryl" is meant an aromatic cyclic group in which the ring atoms include at least one carbon and at least one O, N, or S atom, provided that at least three ring atoms are present. Exemplary heteroaryl groups include oxazolyl, isoxazolyl, tetrazolyl, pyridyl, thienyl, furyl, pyrrolyl, imidazolyl, pyrimidinyl, thiazolyl, indolyl, quinolinyl, isoquinolinyl, benzofuryl, benzothienyl, pyrazolyl, pyrazinyl, pyridazinyl, isothiazolyl, benzimidazolyl, benzothiazolyl, benzoxazolyl, oxadiazolyl, thiadiazolyl, and triazolyl. Heteroaryl groups may be optionally substituted with one or more substituents.

By "heterocyclyl" is meant a non-aromatic cyclic group in which the ring atoms include at least one carbon and at least one O, N, or S atom, provided that at least three ring atoms are present. Exemplary heterocyclyl groups include epoxide, thiiranyl, aziridinyl, azetidinyl, thietanyl, dioxetanyl, morpholinyl, thiomorpholinyl, piperazinyl, piperidinyl, pyrrolidinyl, tetrahydropyranyl, tetrahydrofuranyl, dihydrofuranyl, tetrahydrothienyl, dihydrothienyl, dihydroindolyl, tetrahydroquinolyl, tetrahydroisoquinolyl, pyranyl, pyrazolinyl, pyrazolidinyl, dihydropyranyl, tetrahydroquinolyl, imidazolinyl, imidazolidinyl, pyrrolinyl, oxazolidinyl, isoxazolidinyl, thiazolidinyl, isothiazolidinyl, dithiazolyl, and 1,3-dioxanyl. Heterocyclyl groups may be optionally substituted with one or more substituents.

By a "nitrogen protecting group" is meant those groups intended to protect an amino group against undesirable reactions during synthetic procedures. Commonly used nitrogen protecting groups are disclosed in Greene, "Protective Groups in Organic Synthesis," 3$^{rd}$ Edition (John Wiley & Sons, New York, 1999), which is incorporated herein by reference. Nitrogen protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, alkaryl groups such as benzyl, triphenylmethyl, and benzyloxymethyl, and silyl groups, such as trimethylsilyl. Preferred nitrogen protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

By "oxo" is meant =O.

By an "oxygen protecting group" is meant those groups intended to protect an oxygen containing (e.g., phenol, hydroxyl, or carbonyl) group against undesirable reactions during synthetic procedures. Commonly used oxygen protecting groups are disclosed in Greene, "Protective Groups in Organic Synthesis," 3rd Edition (John Wiley & Sons, New York, 1999), which is incorporated herein by reference. Exemplary oxygen protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxyl, such methyl, methoxymethyl, tetrahydropyranyl, benzyl, p-methoxybenzyl, and trityl; alkoxycarbonyls, such as methylcarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, and 1,3-dioxolane; acylal groups; and dithiane groups, such as 1,3-dithianes, and 1,3-dithiolane); carboxylic acid-protecting groups (e.g., ester groups, such as methyl ester, benzyl ester, t-butyl ester, and orthoesters; and oxazoline groups.

As noted, substituents may be optionally substituted with halo, optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo; —CN; —NO$_2$; —OR$_a$; —N(R$_a$)$_2$; —C(=O)R$_a$; —C(=O)OR$_a$; —S(=O)$_2$R$_a$; —S(=O)$_2$OR$_a$; —P(=O)R$_{a2}$; —O—P(=O)(OR$_a$)$_2$, or —P(=O)(OR$_a$)$_2$, or an ion thereof; wherein each R$_a$ is independently H, $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; when bound to an oxygen atom, an oxygen protecting group; or when bound to a nitrogen atom, a nitrogen protecting group. Cyclic substituents may also be substituted with $C_{1-6}$ alkyl.

Exemplary ions of substituent groups are as follows: an exemplary ion of hydroxyl is —O$^-$; an exemplary ion of —COOH is —COO$^-$; exemplary ions of —PO$_3$H$_2$ are —PO$_3$H$^-$ and —PO$_3$$^{2-}$; an exemplary ion of —PO$_3$HR$_a$ is —PO$_3$R$_a^-$, where R$_a$ is not H; exemplary ions of —PO$_4$H$_2$ are —PO$_4$H$^-$ and —PO$_4^{2-}$; and an exemplary ion of —SO$_3$H is —SO$_3^-$.

BRIEF DESCRIPTION OF THE DRAWINGS

FIGS. 10A-10C. NMR evidence of decomposition of 2,6-DBEAQ in the oxidized form. $^1$H NMR spectra (500 MHz, 1 M KOD in D$_2$O with 10 mM NaCH$_3$SO$_3$ internal standard) of (A) the oxidized form of 2,6-DBEAQ in pH 14 aqueous solution (1 M KOH); (B) 2,6-DBEAQ treated at 75° C. for 8 days at 0.1 M concentration in pH 14 aqueous solution (1 M KOH) in the reduced form and then reoxidized in order to compare to samples tested in the oxidized form; (C) 2,6-DBEAQ treated at 75° C. for 8 days at 0.1 M concentration in pH 14 aqueous solution (1 M KOH) in the oxidized form.

FIGS. 11A-11D. Identification of a decomposition product of 2,6-DBEAQ. 1H NMR spectra (500 MHz, 1 M KOD in D$_2$O with 10 mM NaCH$_3$SO$_3$ internal standard) of (A) aliphatic region of the oxidized form of 2,6-DBEAQ in pH 14 aqueous solution (1 M KOH); (B) γ-hydroxybutyrate; (C) aliphatic region of 2,6-DBEAQ treated at 75° C. for 8 days at 0.1 M concentration in pH 14 aqueous solution (1 M KOH) in the oxidized form; (D) aliphatic region of 2,6-DBEAQ treated at 75° C. for 8 days at 0.1 M concentration in pH 14 aqueous solution (1 M KOH) in the oxidized form with 10 mM γ-hydroxybutyrate added to the NMR sample.

The capacity-limiting side was 5 mL 0.1 M DBEAQ, while the non-capacity-limiting side was 10 mL of the same. Capacities were obtained by full potentiostatic reduction and oxidation of 5 mL of capacity-limiting side; potential was switched between ±0.2 V when magnitude of current dropped to 2 mA/cm$^2$. Linear fits between 0.01 and 10%/day are drawn to compare against experimental data.

Figure 17:
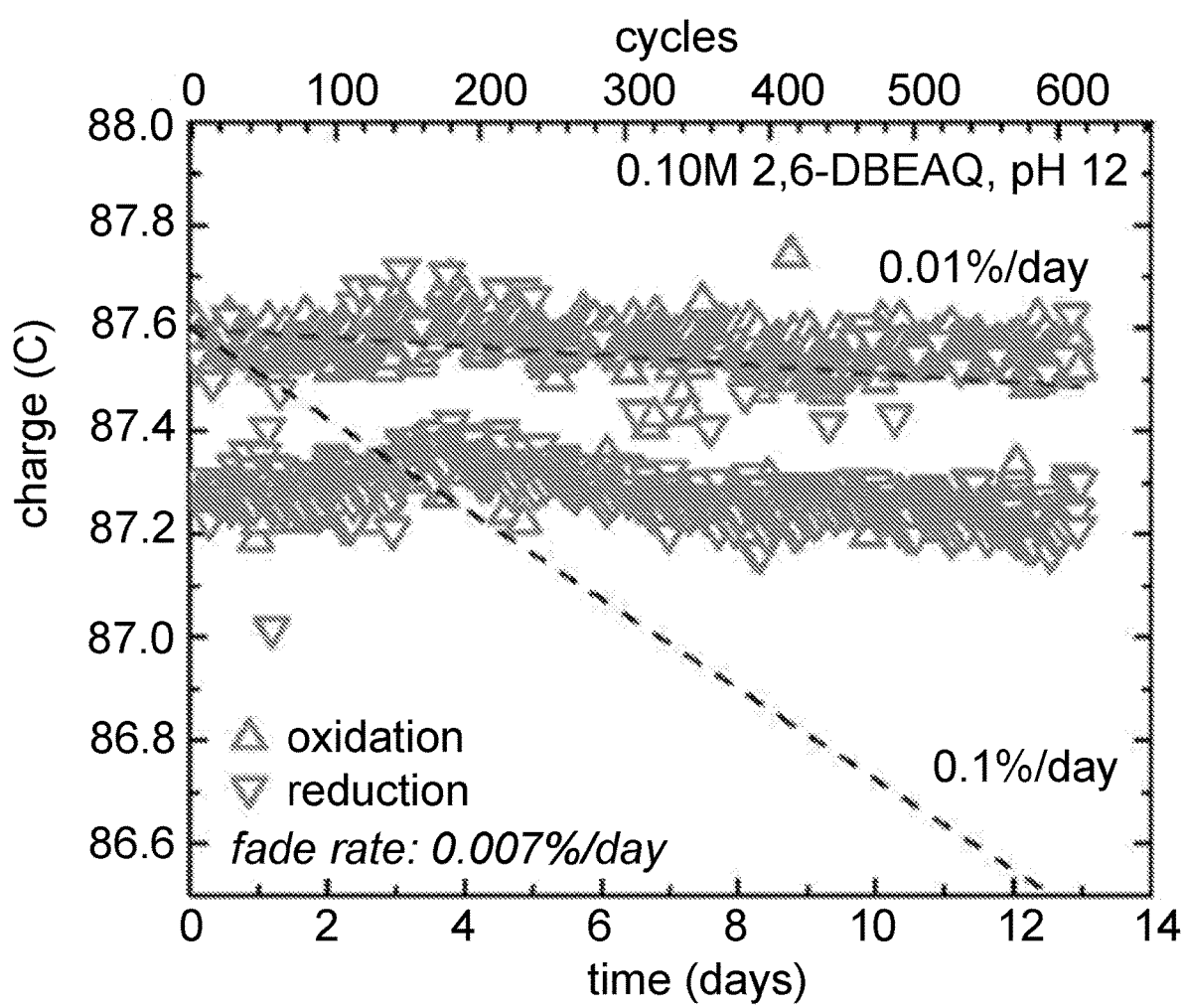

FIG. 17. Unbalanced compositionally-symmetric cell cycling of 0.10 M 2,6-DBEAQ, showing capacity vs. time in 0.01 M KOH (pH 12). The capacity-limiting side was 5 mL 0.1 M 2,6-DBEAQ, while the non-capacity-limiting side was 10 mL of the same. Capacities were obtained by full potentiostatic reduction and oxidation of 5 mL of capacity-limiting side; potential was switched between ±0.2 V when magnitude of current dropped to 2 mA/cm$^2$. Dashed lines with slopes of 0.01 and 0.1%/day are drawn to compare against experimental data, which showed a temporal fade rate of approximately 0.007%/day.

Figure 18A:
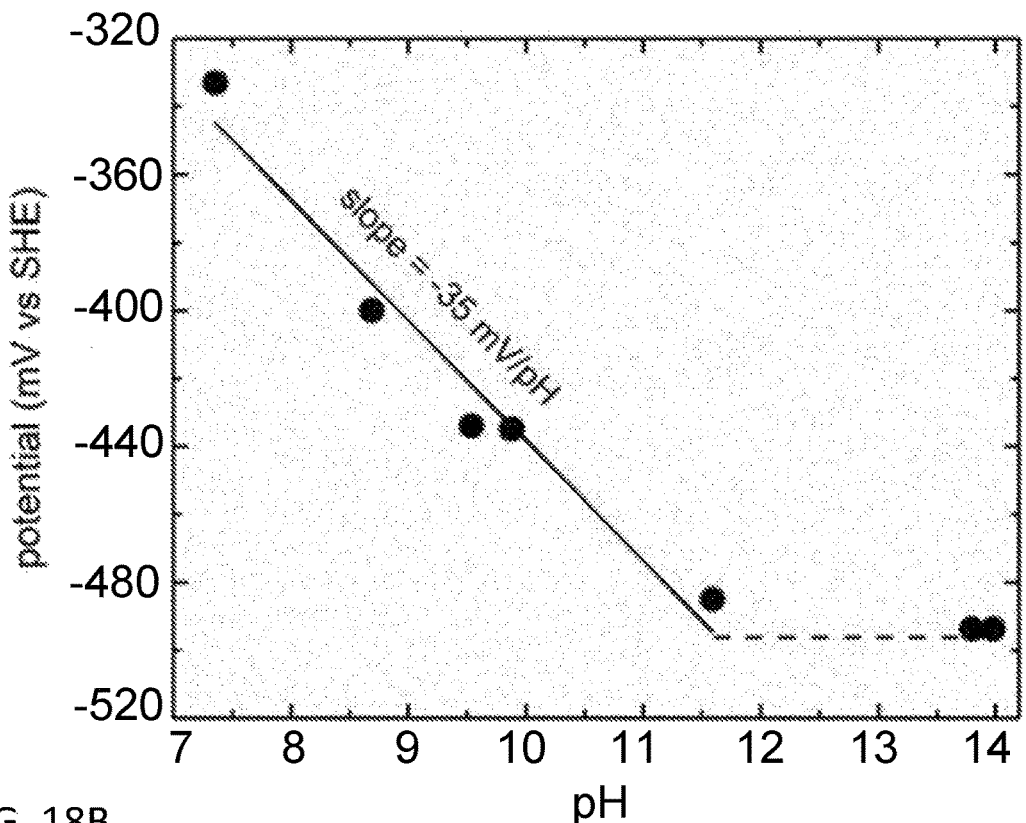
Figure 18B:
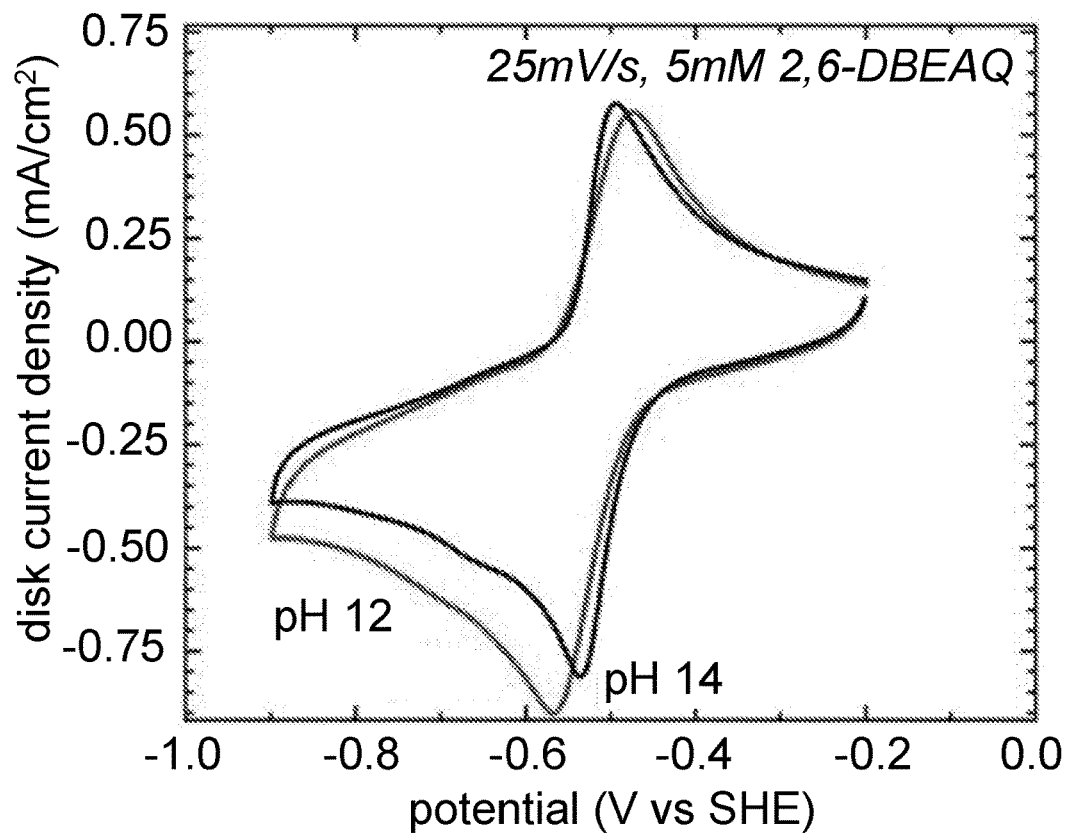

FIGS. 18A-18B. (A) Pourbaix diagram of 2,6-DBEAQ with a slope fit to the data of −35 mV/pH below pH 12. Above pH ~11.5, the potential is pH-independent, indicating that both oxidized and reduced forms of 2,6-DBEAQ are deprotonated. The dashed line has zero slope. (b) Capacitance-corrected CVs of 5 mM 2,6-DBEAQ in 1 M KOH (black curve) and pH 12 buffer (red curve) solution. We hypothesize the wider peak separation in the buffered pH 12 solution to be a result of slower kinetics for the first and second electron reduction steps' rather than a larger difference between their redox potentials.

FIGS. 19A-19D. (A) Cell voltage versus discharge current density at room temperature at 10%, 30%, 50%, 70%, 90%, and 100% SOC. Electrolytes included 5 mL of 2,6-DBEAQ (negolyte) at pH 12 (10 mM KOH) and 38 mL of 0.3 M potassium ferrocyanide and 0.1 M potassium ferricyanide (posolyte) at pH 12. (B) OCV, high-frequency, and polarization ASR versus SOC. (C) Galvanostatic charge and discharge curves from 25 to 250 mA/cm$^2$. The vertical dashed lines indicate the maximum capacity realized with potentiostatic charge and discharge at the voltage cutoffs (1.4 and 0.6 V, respectively), as well as the theoretical capacity. (D) Columbic efficiency, round-trip energy efficiency, and capacity utilization as a percentage of potentiostatic capacity versus current density.

Figure 20:
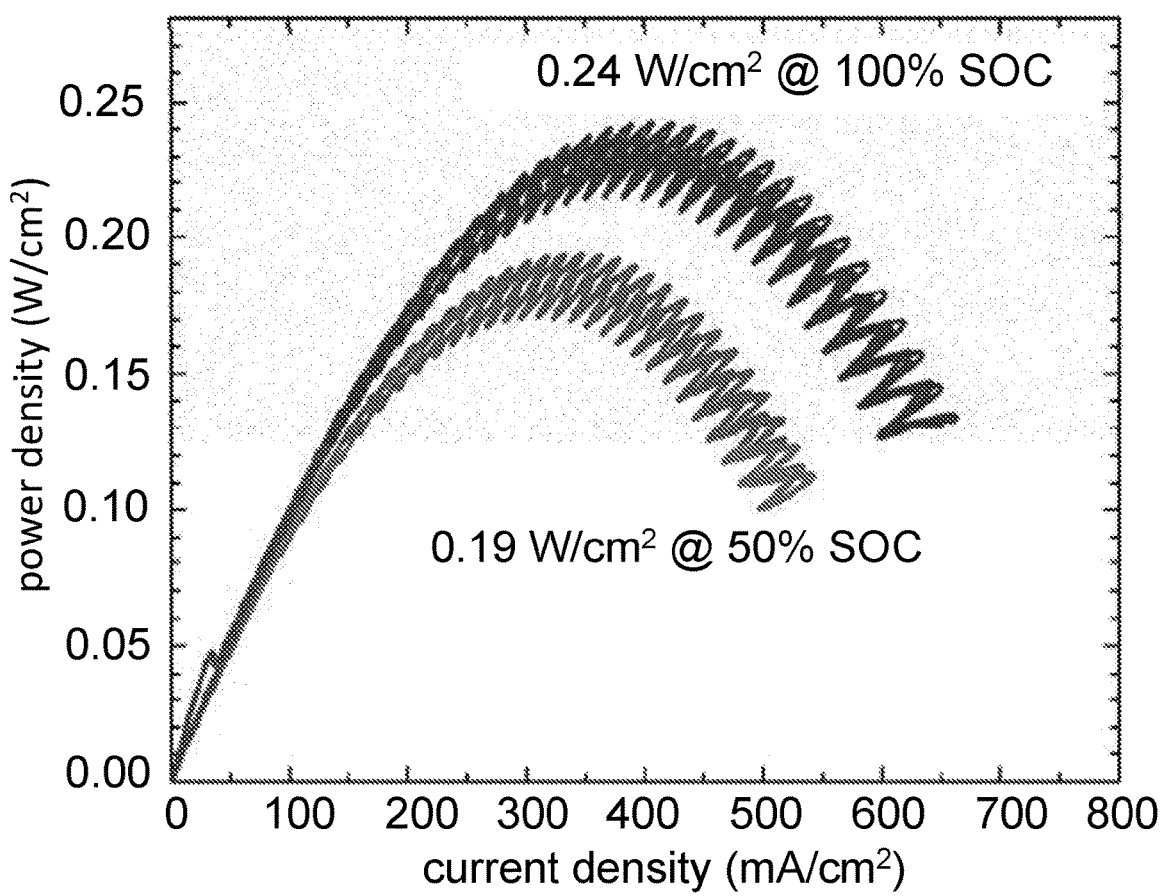

FIG. 20. Power density versus current density for 0.5 M 2,6-DBEAQ at 20° C. at 50% and ~100% SOC.

Figure 21A:
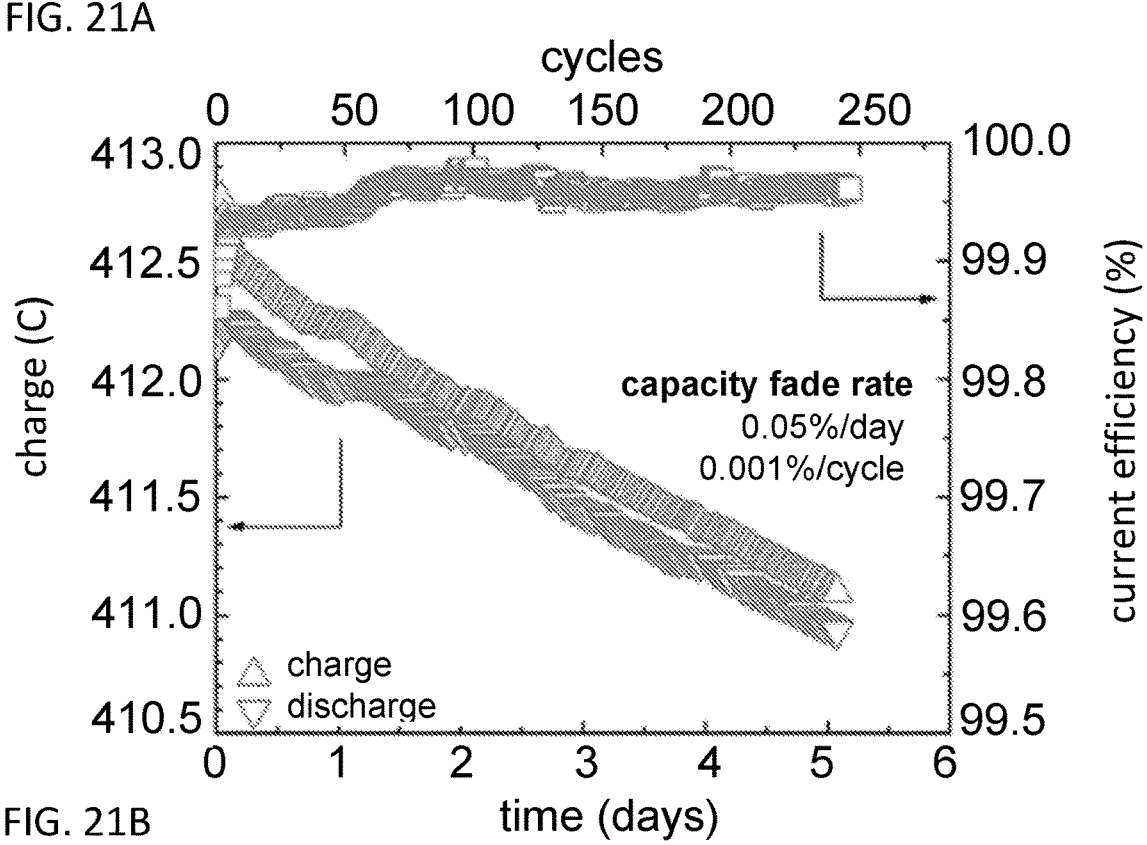
Figure 21B:
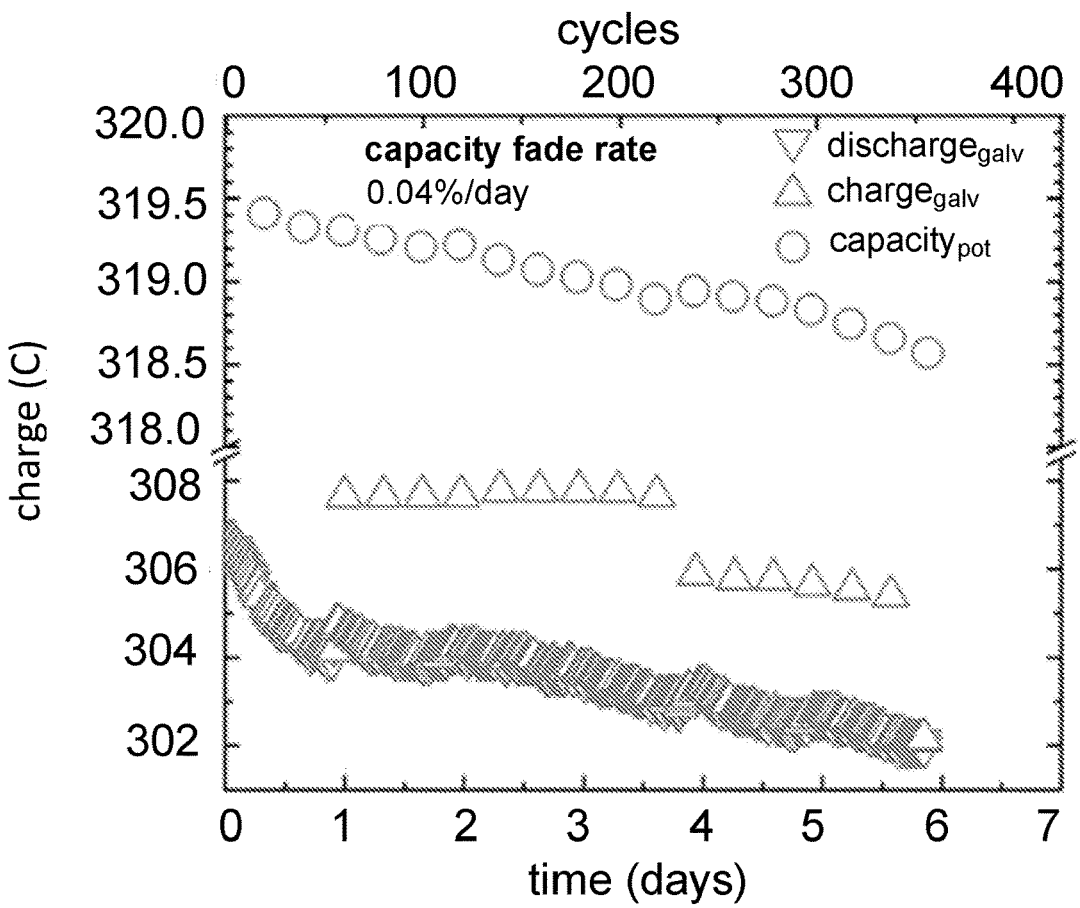

FIGS. 21A-21B. (A) Current efficiency (squares) and charge (upward pointing triangles) and discharge (downward pointing triangles) capacity versus time and cycle number for a negolyte-limited 2,6-DBEAQ-Fe(CN)$_6$ cell. The cell was cycled galvanostatically at 100 mA/cm$^2$ between 1.4 and 0.6 V, and each half-cycle ended with a potentiostatic hold until the magnitude of the current density fell below 2 mA/cm$^2$. The negolyte included 5 mL of 0.5 M 2,6-DBEAQ at pH 12 while the posolyte included 30 mL of 0.3 M potassium ferrocyanide and 0.1 M potassium ferricyanide at pH 12. (B) Evolution of charge (upward pointing triangles) and discharge (downward pointing triangles) capacity for extended charge cycling at 100 mA/cm$^2$. After every twentieth galvanostatic cycle, a potentiostatic charge-discharge cycle was performed, the discharge capacity of which is shown in the open circles. Because the concentration of 2,6-DBEAQ is at its maximum after each potentiostatic discharge, the capacity of the galvanostatic charge step immediately following potentiostatic charge-discharge is higher than in subsequent cycles. This particular cell showed only 65% of its theoretical capacity because a large fraction of salt was left over from the synthesis of 2,6-DBEAQ.

Figure 22A:
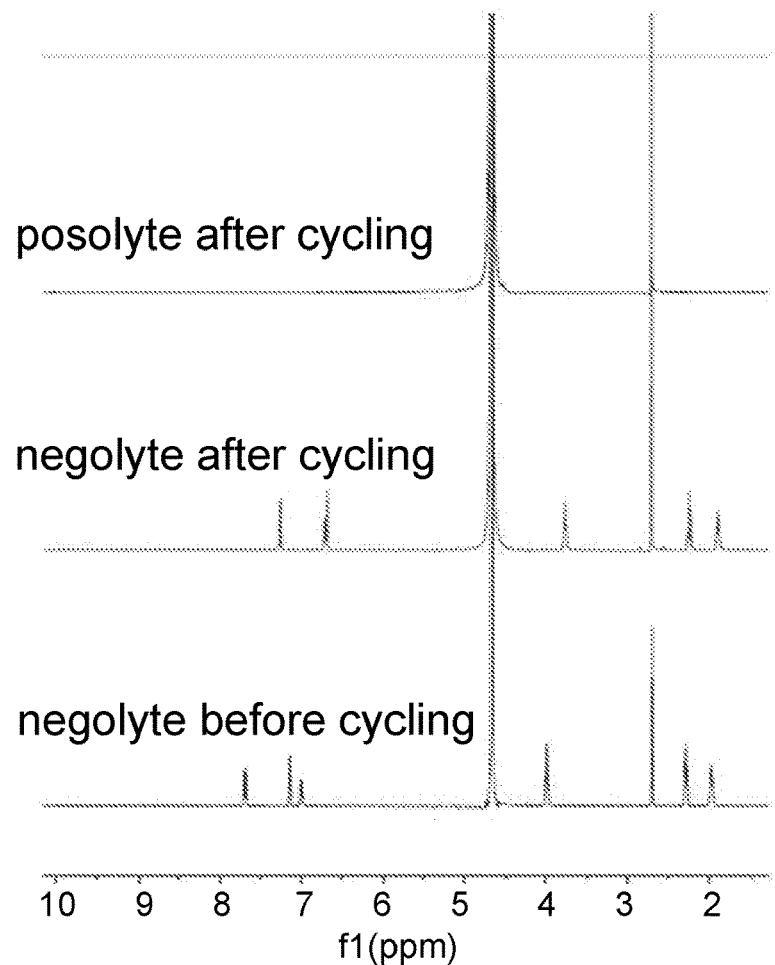
Figure 22B:
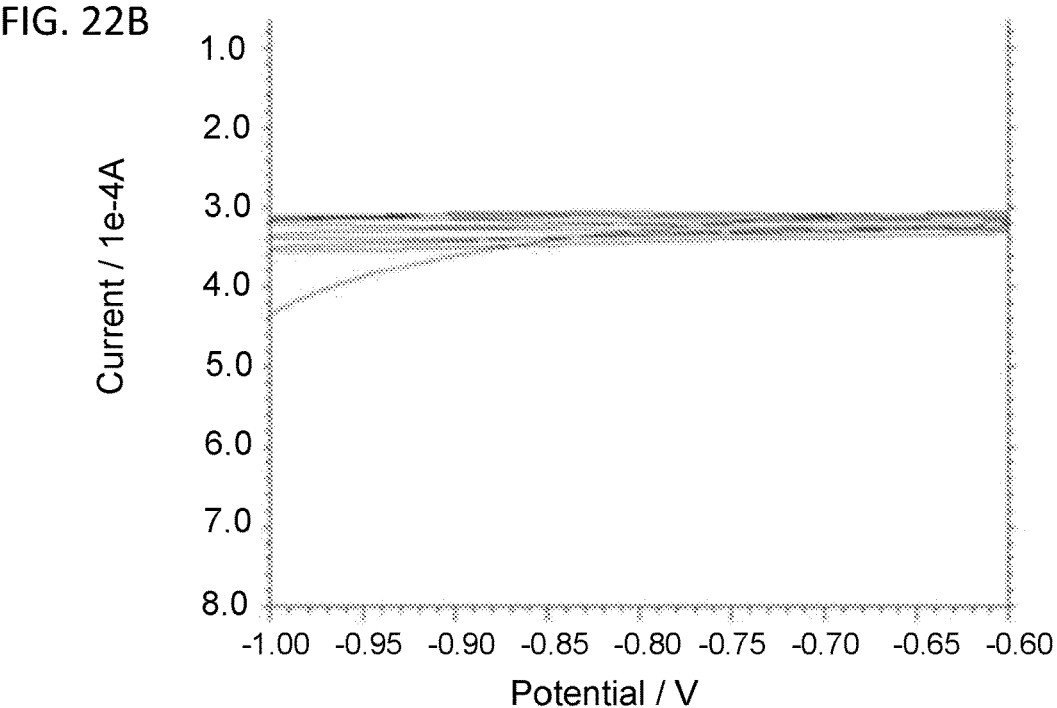

FIGS. 22A-22B. (A) NMR analysis of electrolytes from a cell compositionally similar to that in FIG. 19 and cycled for 11 days. The origin of the peak shifts in NMR is unknown but could stem from differences slight differences in pH. (B) CV measurement of cycled posolyte showing no 2,6-DBEAQ redox peaks within the potential window (vs. Ag/AgCl).

FIGS. 23A-23F. Comparison of the stability of DPPEAQ with respect to alkyl chain cleavage at pH 9 and 12 to that of 2,6-DBEAQ at pH 12. $^1$H NMR spectra (500 MHz, 10 mM NaCH$_3$SO$_3$ internal standard, δ 2.6 ppm) of (A) DPPEAQ at pH 9; (B) DPPEAQ at pH 9, treated for 6 days at 95° C. and 0.1 M concentration; (C DPPEAQ at pH 12; (D) DPPEAQ at pH 12, treated for 6 days at 95° C. and 0.1 M concentration; (E) 2,6-DBEAQ at pH 12; (F) 2,6-DBEAQ at pH 12, treated for 6 days at 95° C. and 0.1 M concentration. After treatment, 2,6-DBEAQ at pH 12 exhibits 15% decomposition, whereas DPPEAQ at both pH 9 and pH 12 exhibits no significant decomposition.

FIGS. 24A-24D. Comparison of the stability of DPPEAQ with respect to alkyl chain cleavage to that of 2,6-DBEAQ at pH 14. $^1$H NMR spectra (500 MHz, 10 mM NaCH$_3$SO$_3$ internal standard, δ 2.6 ppm) of (A) DPPEAQ at pH 14; (B) DPPEAQ at pH 14, treated for 5.5 days at 95° C. and 0.1 M concentration; (C) 2,6-DBEAQ at pH 14; (D) 2,6-DBEAQ at pH 14, treated for 5.5 days at 95° C. and 0.1 M concentration. After treatment, 2,6-DBEAQ and DPPEAQ both exhibit 45% decomposition. The relative integrals and splitting of the peaks in the spectra of DPPEAQ after treatment are consistent with the products of (3-hydroxypropyl)phosphonate cleavage. Samples of DPPEAQ at 0.1 M concentration and pH 14 in both the oxidized and reduced form were stored in FEP bottles and heated in an oven at 65° C. for 2 weeks. The extent of decomposition was determined by $^1$H NMR, with peak integrals measured relative to an internal standard of NaCH$_3$SO$_3$ prepared at 10 mM concentration in D$_2$O.

Figure 25:
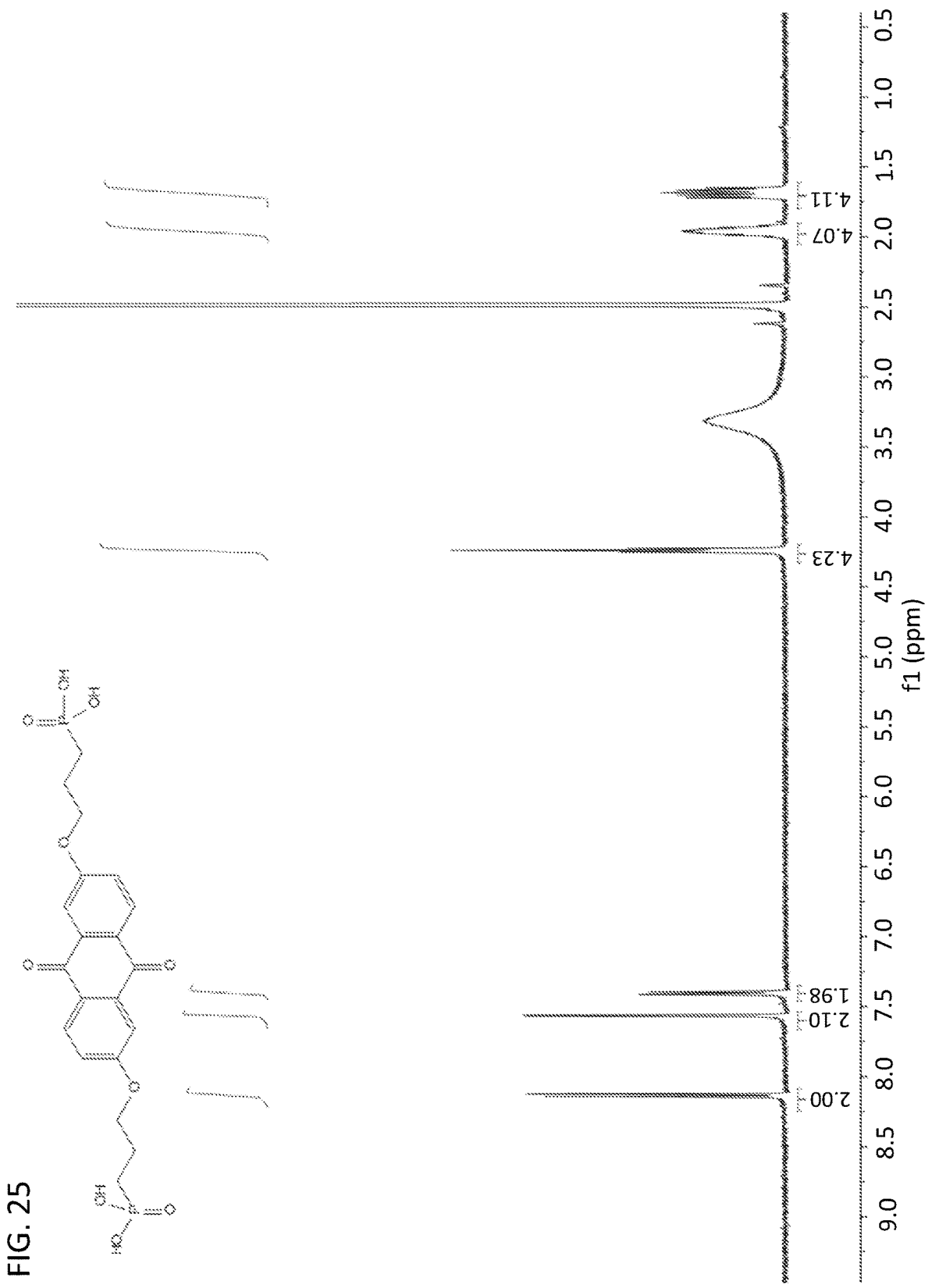

FIG. 25. $^1$H NMR spectrum of DPPEAQ. Solvent peaks are those that are not integrated.

FIGS. 26A-26C. Comparison of DPPEAQ stability in the oxidized and reduced forms at pH 14. $^1$H NMR spectra (500 MHz, 10 mM NaCH$_3$SO$_3$ internal standard, δ 2.6 ppm) of (A) DPPEAQ at pH 14; (B) DPPEAQ at pH 14, treated for 2 weeks at 65° C. and 0.1 M concentration in the oxidized form; (C) DPPEAQ at pH 14, treated for 12 days at 65° C. and 0.1 M concentration in the reduced form (sample reoxidized prior to collecting $^1$H NMR spectrum). Unlike the oxidized form of DPPEAQ, the reduced form exhibits robust chemical stability after treatment, even at pH 14.

Figure 27A:
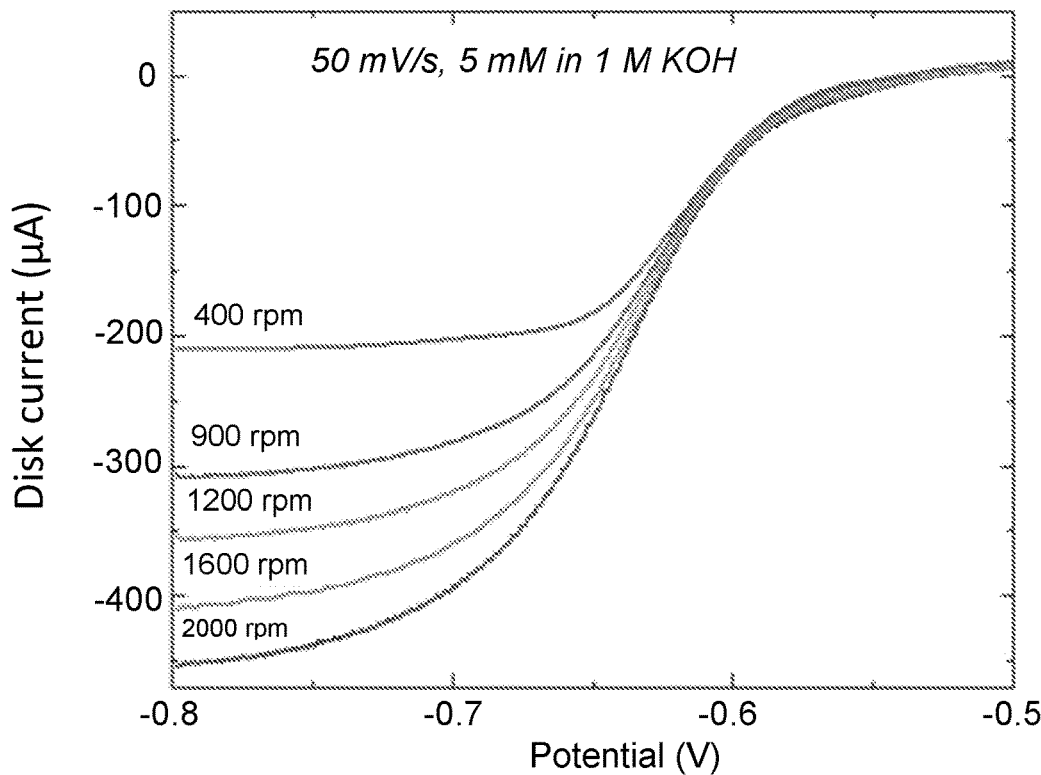
Figure 27B:
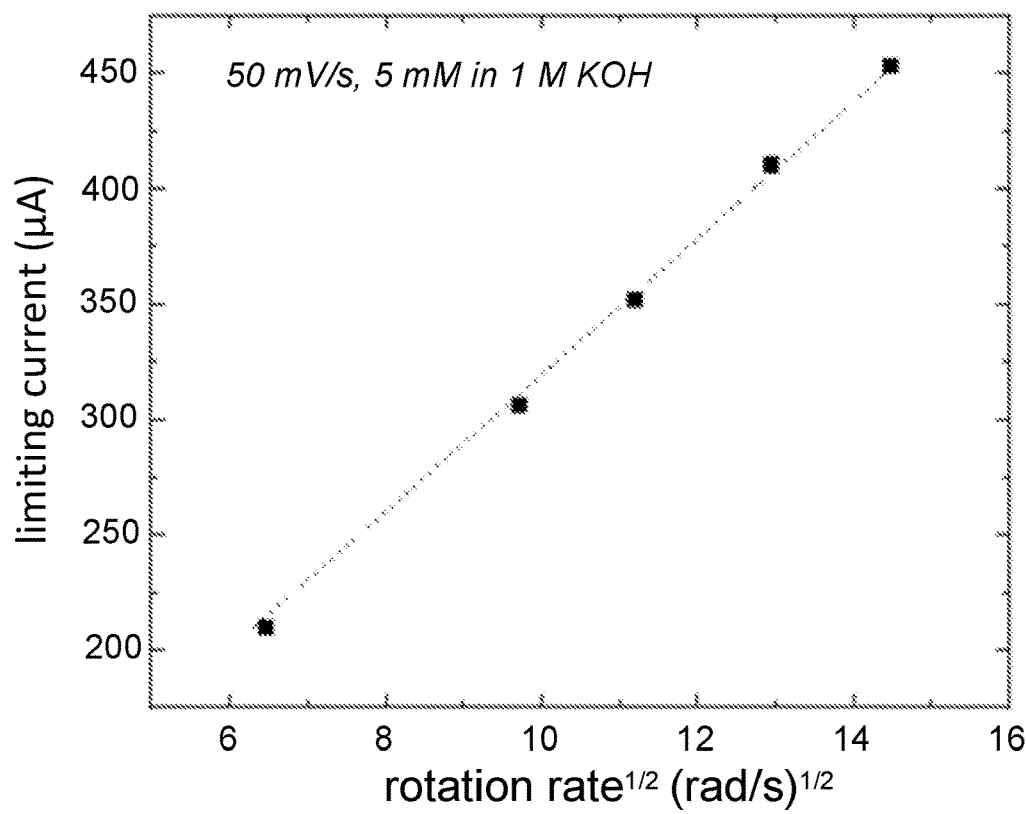

FIGS. 27A-27B. (A) Rotating Disk Electrode study of the reduction of 5 mM DPPEAQ in 1M KOH on a glassy carbon electrode at rotation rates between 400 and 2000 rpm. (B) Levich plot (limiting current vs. square root of rotation rate in rad/s) of 5 mM DPPEAQ in 1 M KOH. The slope yields a diffusion coefficient for the oxidized form of DPPEAQ of 1.37×10$^{-6}$ cm$^2$/s.

FIGS. 28A-28D. (A) Cyclic voltammograms of 1 mM DPPEAQ at pH 9 buffer (black solid), pH 12 buffer (red solid), pH 9 unbuffered (black dash) and pH 12 unbuffered (red dash), at a scan rate of 100 mV s$^{-1}$, on a glassy carbon working electrode. (B) Galvanostatic cycling of the DPPEAQ cell at 20 mA/cm$^2$ for 16 consecutive cycles in the glove bag. Electrolytes included 6.5 mL 0.1 M DPPEAQ (negolyte) in 1 M KCl solution at pH 9 and 40 mL 0.1 M potassium ferrocyanide and 0.01 M potassium ferricyanide (posolyte) in 1 M KCl solution at pH 9. The pH probe was immersed in the negolyte to monitor the pH of the solution.

Charge/discharge capacity, current efficiency (CE), and pH of the negolyte before and after charging were plotted as functions of the cycle number. (C) Representative curves of cell potential and negolyte pH vs. time. (D) Repeating experiments (B) and (C) but in a glove box instead of in the glove bag.

Figure 29:
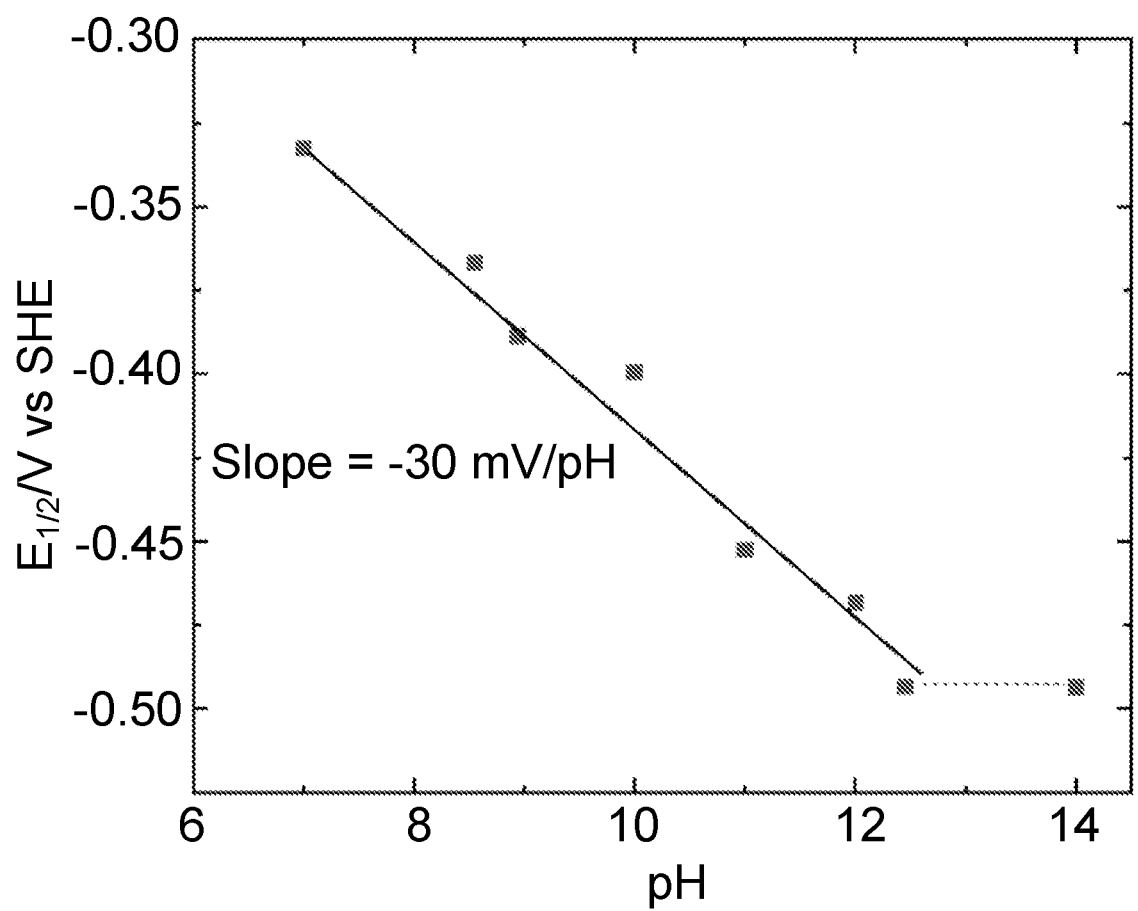

FIG. 29. Pourbaix diagram of DPPEAQ with a slope of −30 mV/pH fit to the data below pH 12. Above pH ~12.4, the potential is pH-independent, indicating that both oxidized and reduced forms of DPPEAQ are deprotonated. The dashed line has zero slope.

FIGS. 30A-30D. (A) Unbalanced compositionally-symmetric cell cycling of 0.1 M DPPEAQ at pH 13, showing capacity as a function of time. Capacities were obtained by full potentiostatic reduction and oxidation at ±0.2 V of the capacity-limiting side. (B) Full cell OCV vs. SOC at room temperature at 10, 50, and 90% SOC. Electrolytes included 5 mL 0.5 M DPPEAQ (negolyte) at pH 9 and 80 mL 0.4 M potassium ferrocyanide and 0.1 M potassium ferricyanide (posolyte) at pH 9. (C) Cell potential and power density vs. current density. (D) Current efficiency (squares) and charge (upward-pointing triangles) and discharge (downward-pointing triangles) capacity vs. time and cycle number. The cell was cycled galvanostatically at 100 mA/cm² between 1.5 and 0.5 V, and each half-cycle ended with a potentiostatic hold until the magnitude of the current density fell below 2 mA/cm². Inset: capacity vs. cell voltage at the 1$^{st}$, the 10$^{th}$, the 100$^{th}$ and the 480$^{th}$ cycle, respectively.

Figure 31:
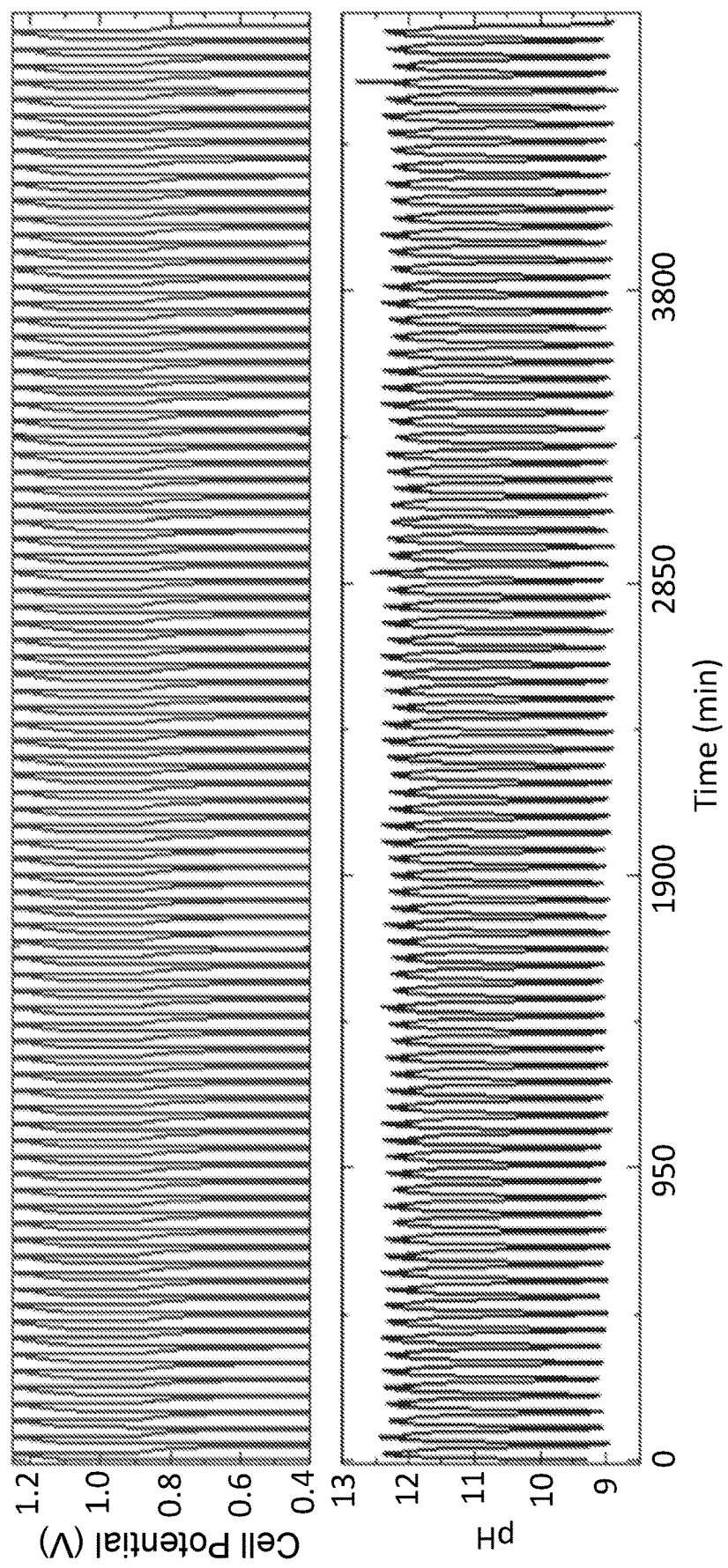

FIG. 31. Representative curves of cell potential and negolyte pH versus time of the DPPEAQ cell in the glove box. Electrolytes included 5 mL 0.5 M DPPEAQ (negolyte) at pH 9 and 80 mL 0.4 M potassium ferrocyanide and 0.1 M potassium ferricyanide (posolyte) at pH 9. The pH probe was immersed in the negolyte to monitor the pH of the solution.

DETAILED DESCRIPTION

We disclose quinone compounds and related species that possess significant advantages when used as a redox active material in a battery, e.g., a redox flow battery. In particular, the compounds provide RFBs with extremely high capacity retention. For example, RFBs of the invention can be cycled for 500 times with negligible loss of capacity, and such batteries could be employed for years of service. Thus, the invention provides a high efficiency, long cycle life redox flow battery with reasonable power cost, low energy cost, and all the energy scaling advantages of a flow battery. Quinone-to-hydroquinone cycling occurs rapidly and reversibly and provides high current density (high current density is very important because the cost per kW of the system is typically dominated by the electrochemical stack's cost per kW, which is inversely proportional to the power density—the product of current density and voltage), high efficiency, and long lifetime in a flow battery.

Batteries of the invention employ a first redox active material and a second redox active material, which is the quinone compound of the invention. Typically, the quinone compound is in the negolyte and therefore in its reduced, hydroquione form when fully charged. As the battery is discharged, the hydroquinone is then oxidized to its corresponding quinone. During charging the quinone is similarly reduced to the hydroquinone. In the batteries of the invention, energy is stored in the quinone/hydroquinone, which is not merely a charge transfer catalyst in the reduction or oxidation of a secondary species.

Exemplary quinone compounds are of formula I:

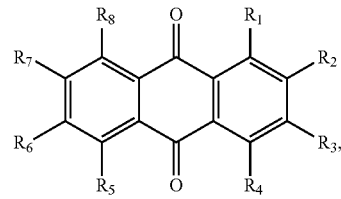

wherein each of $R_1$-$R_8$ is independently H; halo; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo, —NO$_2$; —OR$_a$; —N(R$_a$)$_2$; —C(=O)R$_a$; —C(=O)OR$_a$; —S(=O)$_2$R$_a$; —S(=O)$_2$OR$_a$; —OS(=O)$_2$OR$_a$; —P(=O)R$_{a2}$; —P(=O)(OR$_a$)$_2$; and —OP(=O)(OR$_a$)$_2$; —X$_1$- L$_1$-C(O)O—Y$_1$; —X$_2$-L$_2$-C(O)O—Y$_2$; —X$_3$-L$_3$-P(=O)(OY$_3$)$_2$; or —X$_4$-L$_4$-P(=O)(OY$_4$)$_2$;

wherein each R$_a$ is independently H; optionally substituted $C_1$-6 alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; or optionally substituted $C_{1-9}$ heteroaryl having one to four heteroatoms independently selected from O, N, and S;

$X_1$, $X_2$, $X_3$, and $X_4$ are independently O, S, or CH$_2$; $L_1$, $L_2$, $L_3$, and $L_4$ are independently $C_1$-$C_6$ alkylene; and $Y_1$, $Y_2$, $Y_3$, and $Y_4$ are independently H or optionally substituted $C_1$-$C_6$ alkyl, provided that one and only one of $R_1$-$R_8$ is —X$_1$-L$_1$-C(O)O—Y, or —X$_3$-L$_3$-P(=O)(OY$_3$)$_2$ and one and only one of $R_1$-$R_8$ is —X$_2$-L$_2$-C(O)O—Y$_2$ or —X$_4$-L$_4$-P(=O)(OY$_4$)$_2$. In particular embodiments, each of $R_1$-$R_8$ is independently H; halo; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo, —NO$_2$; —OR$_a$; —N(R$_a$)$_2$; —C(=O)R$_a$; —C(=O)OR$_a$; —S(=O)$_2$R$_a$; —S(=O)$_{20}$R$_a$; —P(=O)R$_{a2}$; and —P(=O)(OR$_a$)$_2$—X$_1$-L$_1$-C(O)O—Y$_1$; —X$_2$-L$_2$-C(O)O—Y$_2$; —X$_3$-L$_3$-P(=O)(OY$_3$)$_2$; or —X$_4$-L$_4$-P(=O)(OY$_4$)$_2$, e.g., when the pH of the electrolyte is ≥7 e.g., the pH is from 8-13. Exemplary compounds are 2,6-DBEAQ, 1,2-DBEAQ, 1,8-DBEAQ, and DPPEAQ.

Compounds also include salts, ions (e.g., —COO$^-$, —PO$_3$H$^-$, or —PO$_3^{2-}$), or a hydroquinone thereof. As will be understood, a hydroquinone of a compound of formula I has the formula:

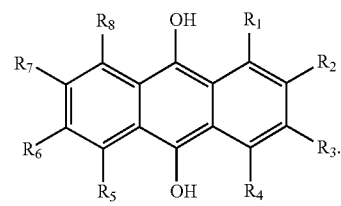

Salts or ions may also be in hydroquinone form.

Examples of first redox active materials that may be used in a battery of the invention are bromine, chlorine, iodine, oxygen, vanadium, chromium, cobalt, iron (e.g., ferricyanide/ferrocyanide or a ferrocene derivative, e.g., as described in PCT/US2017/046783), aluminum, e.g., aluminum(III) biscitrate monocatecholate, manganese, cobalt, nickel, copper, or lead, e.g., a manganese oxide, a cobalt oxide, or a lead oxide. Other redox active species suitable for use in batteries of the invention are described in WO 2014/052682, WO 2015/048550, and WO 2016/144909, the redox active species of which are incorporated by reference.

Electrolytes

In some embodiments, the electrolytes are both aqueous, where the first and second redox active species are in aqueous solution or aqueous suspension. In addition to the redox active species, the electrolyte may include other solutes, e.g., acids (e.g., HCl) or bases (e.g., NaOH or KOH) or alcohols (e.g., methyl, ethyl, or propyl) and other co-solvents to increase the solubility of a particular quinone/hydroquinone. In certain embodiments, the pH of the electrolyte may be >7, e.g., at least 8, 9, 10, 11, 12, 13, or 14, 8-14, 9-14, 10-14, 11-14, 12-14, 13-14, or about 14. The electrolyte may or may not be buffered to maintain a specified pH. The first and second redox actives species will be present in amounts suitable to operate the battery, for example, from 0.1-15 M, or from 0.1-10 M. In some embodiments, the solution is at least 10%, 20%, 30%, 40%, 50%, 60%, 70%, or 80% water, by mass. Quinones, hydroquinones, salts, and/or ions thereof may be present in a mixture.

Electrode Materials

Electrodes for use with an organic compound or ion thereof (e.g., quinone or hydroquinone) include any carbon electrode, e.g., glassy carbon electrodes, carbon paper electrodes, carbon felt electrodes, or carbon nanotube electrodes. Titanium electrodes may also be employed. Electrodes can also be made of a high specific surface area conducting material, such as a nanoporous metal sponge (T. Wada, A. D. Setyawan, K. Yubuta, and H. Kato, *Scripta Materialia* 65, 532 (2011)), which has been synthesized previously by electrochemical dealloying (J. D. Erlebacher, M. J. Aziz, A. Karma, N. Dmitrov, and K. Sieradzki, *Nature* 410, 450 (2001)), or a conducting metal oxide, which has been synthesized by wet chemical methods (B. T. Huskinson, J. S. Rugolo, S. K. Mondal, and M. J. Aziz, arXiv:1206.2883 [cond-mat.mtrl-sci]; *Energy & Environmental Science* 5, 8690 (2012); S. K. Mondal, J. S. Rugolo, and M. J. Aziz, *Mater. Res. Soc. Symp. Proc.* 1311, GG10.9 (2010)). Chemical vapor deposition can be used for conformal coatings of complex 3D electrode geometries by ultra-thin electrocatalyst or protective films. Electrodes suitable for other redox active species are known in the art.

Ion Conducting Barriers

The ion conducting barrier allows the passage of ions, such as sodium or potassium, but not a significant amount of the quinone, hydroquinone, or other redox active species. Examples of ion conducting barriers are NAFION®, i.e., sulfonated tetrafluoroethylene based fluoropolymer-copolymer, FUMASEP®, i.e., non-fluorinated, sulfonated polyaryletherketone-copolymer, e.g., FUMASEP® E-620(K), hydrocarbons, e.g., polyethylene, and size exclusion barriers, e.g., ultrafiltration or dialysis membranes with a molecular weight cut off of 100, 250, 500, or 1,000 Da. For size exclusion membranes, the required molecular weight cut off is determined based on the molecular weight of the organic compound (e.g., quinone or hydroquinone) or other redox active species employed. Porous physical barriers may also be included, when the passage of redox active species is tolerable.

Additional Components

A battery of the invention may include additional components as is known in the art. Quinones, hydroquinones, and other redox active species in aqueous solution or aqueous suspension are housed in a suitable reservoir. A battery may further include one or more pumps to pump aqueous solutions or suspensions past one or both electrodes. Alternatively, the electrodes may be placed in a reservoir that is stirred or in which the solution or suspension is recirculated by any other method, e.g., convection, sonication, etc. Batteries may also include graphite flow plates and corrosion-resistant metal current collectors.

The balance of the system around the cell includes fluid handling and storage, and voltage and round-trip energy efficiency measurements can be made. Systems configured for measurement of catholyte and anolyte (e.g., negolyte and posolyte) flows and pH, pressure, temperature, current density and cell voltage may be included and used to evaluate cells. Testing is performed as quinone and pH and the cell temperature are varied. In one series of tests, the current density is measured at which the voltage efficiency drops to 90%. In another, the round-trip efficiency is evaluated by charging and discharging the same number of amp-minutes while tracking the voltage in order to determine the energy conversion efficiency. This is done initially at low current density, and the current density is then systematically increased until the round-trip efficiency drops below 80%. Fluid sample ports can be provided to permit sampling of both electrolytes, which will allow for the evaluation of parasitic losses due to reactant crossover or side reactions. Electrolytes can be sampled and analyzed with standard techniques.

Suitable cells, electrodes, membranes, and pumps for redox flow batteries are known in the art, e.g., WO 2014/052682, WO 2015/048550, and WO 2016/144909, the battery components of which are hereby incorporated by reference.

Example 1. Synthesis of 2,6-DBEAQ

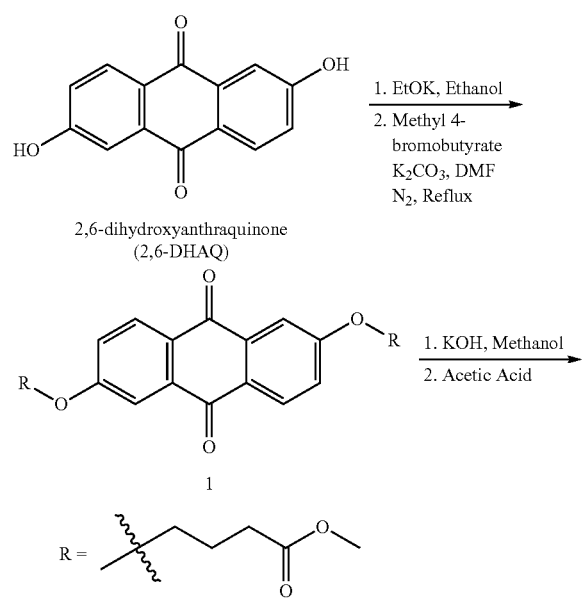

Scheme 1.
Synthesis of 4,4'-((9,10-anthraquinone-2,6-diyl)dioxy)dibutyric acid, abbreviated as 2,6-DBEAQ -continued

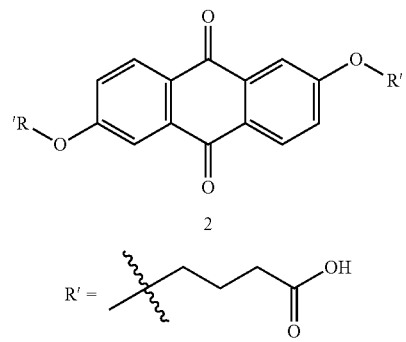

Scheme 2. Alternative Synthesis of 2,6-DBEAQ

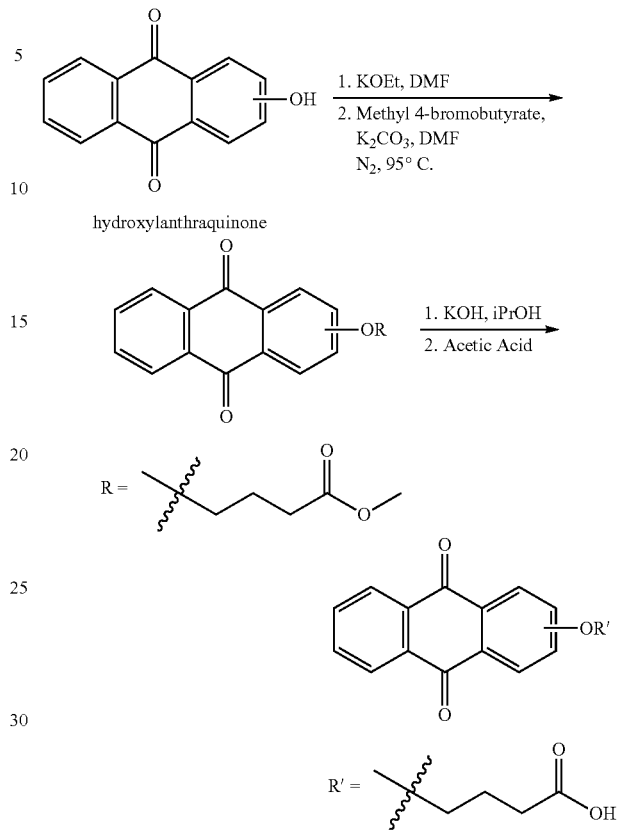

2,6-di hydroxyanthraquinone (2,6-DHAQ) was purchased from AK Scientific. Methyl 4-bromobutyrate was purchased from VWR. All other chemicals were purchased from Sigma Aldrich. All chemicals were used as received unless specified otherwise.

Dimethyl 4,4'-((9,10-anthraquinone-2,6-diyl)dioxy)dibutyrate (1) 2,6-DHAQ was first converted to its dipotassium salt (2,6-DHAQK$_2$) by adding 2,6-DHAQ (5 g, 20.8 mmol) to a beaker of absolute ethanol (200 mL). Under vigorous stirring, potassium ethoxide (24 wt % solution in ethanol, 32.6 mL, 83.3 mmol) was added dropwise. The mixture was stirred at room temperature for 15 minutes, and the red solid was vacuum filtered, washed twice with cold absolute ethanol (20+20 mL), and dried under vacuum overnight at 40° C. For the O-alkylation reaction, 2,6-DHAQK$_2$ (2 g, 6.3 mmol) was added to a 100 mL round-bottom flask followed by the addition of anhydrous DMF (40 mL) and anhydrous K$_2$CO$_3$ (0.87 g, 6.3 mmol). The solution was first stirred and heated to 120° C. under nitrogen for 30 minutes, and then methyl 4-bromobutyrate (2 mL, 15.8 mmol) was added. The reaction mixture was then brought to reflux for 12 hours. After cooling to room temperature, DI water (25 mL) was added to the mixture to dissolve inorganic salt and to precipitate the product 1. The precipitate was vacuum filtered and washed thoroughly with DI water (50 mL). The product was analyzed by $^1$H NMR and used for the next step reaction without further purification. Final yield: 57%.

4,4'-((9,10-anthraquinone-2,6-diyl)dioxy)dibutyric acid, 2,6-DBEAQ (2) Product 1 (1 g, 2.23 mmol) was added along with KOH (0.52 g, 9 mmol) to a flask filled with water-methanol mixture (2:1 v/v, 60 mL). The solution was vigorously stirred and heated to 40° C. for 12 hours. During the reaction, all solids dissolved, and the solution turned into a dark red color. After reaction, the solution was transferred to a larger 500 mL flask, diluted with DI water (200 mL), and glacial acetic acid was added until the solution pH dropped down to 4. The mixture was vigorously stirred for 1 hour followed by vacuum filtration and thorough washing with DI water (100 mL). The product was dried under vacuum at 40° C., analyzed by $^1$H NMR and used for electrochemical measurement without further purification. Final yield: 99%.

Figure 1:
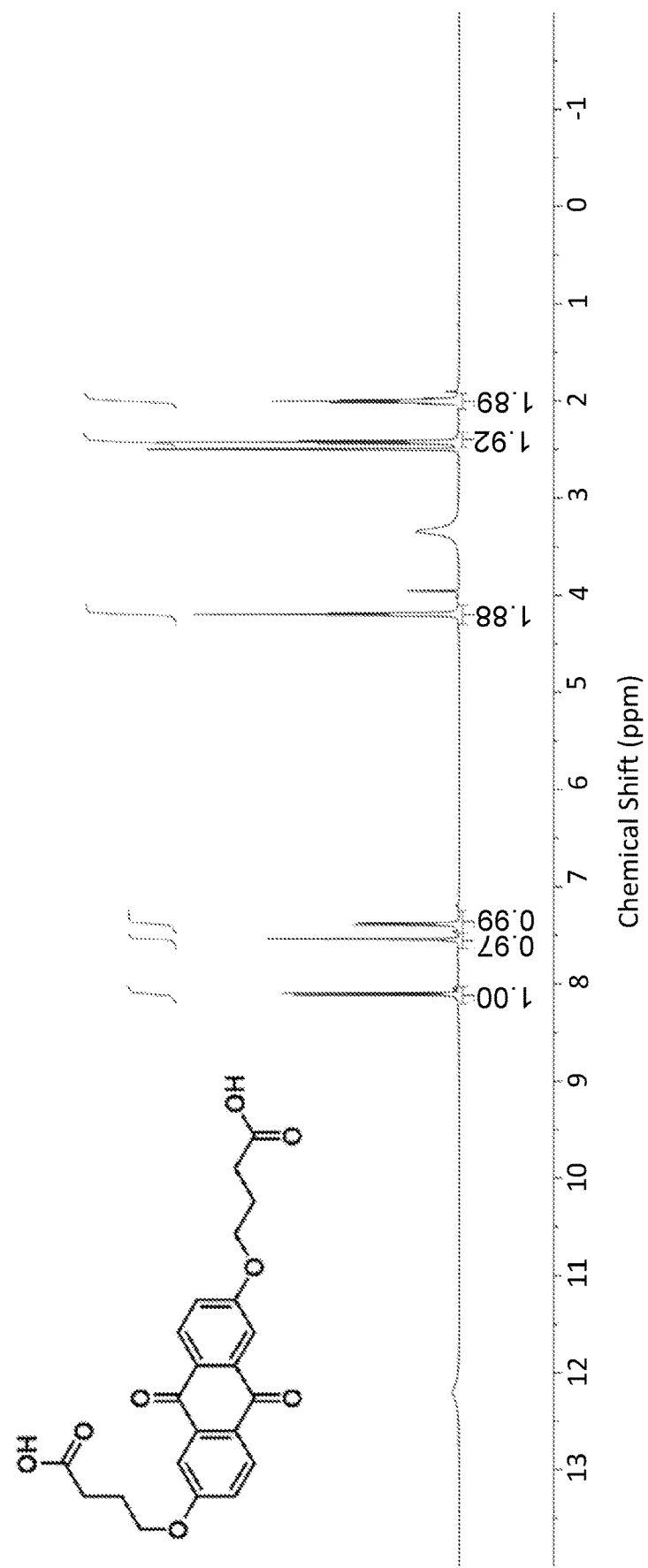
FIG. 1. $^1$H NMR Spectrum of 4,4'-((9,10-anthraquinone-2,6-diyl)dioxy)dibutyric acid (2,6-DBEAQ). $^1$H NMR (500 MHz, DMSO-d$_6$): δ 8.11 (d, J=8.6 Hz, 1H), 11.79 (s, 1H), 7.54 (d, J=2.6 Hz, 1H), 7.38 (dd, J=8.7, 2.6 Hz, 1H), 4.20 (t, J=6.4 Hz, 2H), 2.43 (t, J=7.3, 2H), 2.00 (m, 2H). Solvent peaks are the ones that are not integrated. Final yield: 57%.

The $^1$H NMR spectrum of 4,4'-((9,10-anthraquinone-2,6-diyl)dioxy)dibutyric acid (2,6-DBEAQ) is shown in FIG. 1.

2,6-di hydroxyanthraquinone (2,6-DHAQ) was purchased from AK Scientific. Methyl 4-bromobutyrate was purchased from VWR. All other chemicals were purchased from Sigma Aldrich. All chemicals were used as received unless specified otherwise.

Dimethyl 4,4'-((9,10-anthraquinone-2,6-diyl)dioxy)dibutyrate (1) 2,6-DHAQ was first converted to its dipotassium salt (2,6-DHAQK$_2$) by adding 2,6-DHAQ (5 g, 20.8 mmol) to a 250 mL oven-dried flask of dimethylformamide (250 mL). Under vigorous stirring, potassium ethoxide (6.1 g, 72.9 mmol) was added. The mixture solution was stirred at room temperature for 15 minutes. For the O-alkylation reaction, 2,6-DHAQK$_2$ (6.5 g, 20.8 mmol) was mixed with anhydrous K$_2$CO$_3$ (14.3 g, 104 mmol) and 4-bromobutyrate (12.4 mL, 104 mmol). The reaction mixture was then heated to 95° C. overnight. After cooling to 0° C., DI water (150 mL) was added to the mixture to dissolve inorganic salt and to precipitate the ester precursor of DBEAQ. The precipitate was vacuum filtered and washed thoroughly with DI water (50 mL). The product was analyzed by $^1$H NMR and used for the next step reaction without further purification. Final yield: 87%.

4,4'-((9,10-anthraquinone-2,6-diyl)dioxy)dibutyric acid (2) The ester precursor of DBEAQ (1 g, 2.23 mmol) was added along with KOH (0.52 g, 9 mmol) to a flask filled with water-isopropanol mixture (2:1 v/v, 60 mL). The solution was vigorously stirred and heated to 60° C. for 12 hours. During the reaction, all solid dissolved, and the solution turned into a dark red color. After reaction, the solution was transferred to a larger 500 mL flask and diluted with DI water (200 mL). Glacial acetic acid was added until the solution pH dropped to 4. The mixture was vigorously stirred for 1 hour, followed by vacuum filtration and thorough washing with DI water (100 mL). The product was vacuum dried, analyzed by 1H NMR, and used for electrochemical measurement without further purification. Final yield: 99%

Figure 2:
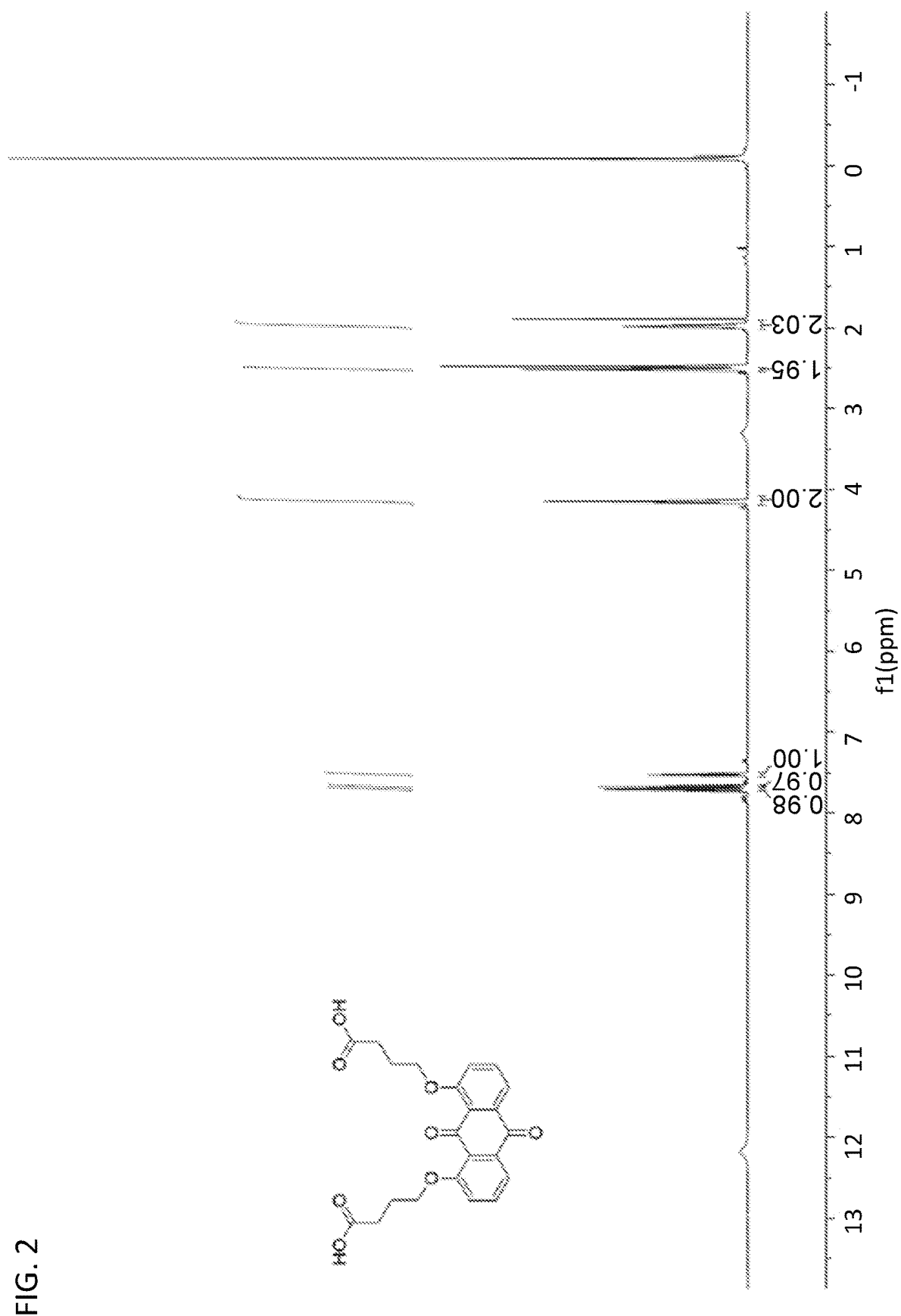
FIG. 2. $^1$H NMR spectrum of 1,8-DBEAQ. 1H NMR (500 MHz, DMSO-d$_6$): δ 12.17 (s, 2H), 7.71 (m, 2H), 7.65 (m, 2H), 7.52 (dd, J=8.3, 1.3 Hz, 2H), 4.15 (t, J=6.3 Hz, 4H), 2.53 (t, J=7.3 Hz, 4H), 1.89 (m, 4H). Final yield: 64.4%.
Figure 3:
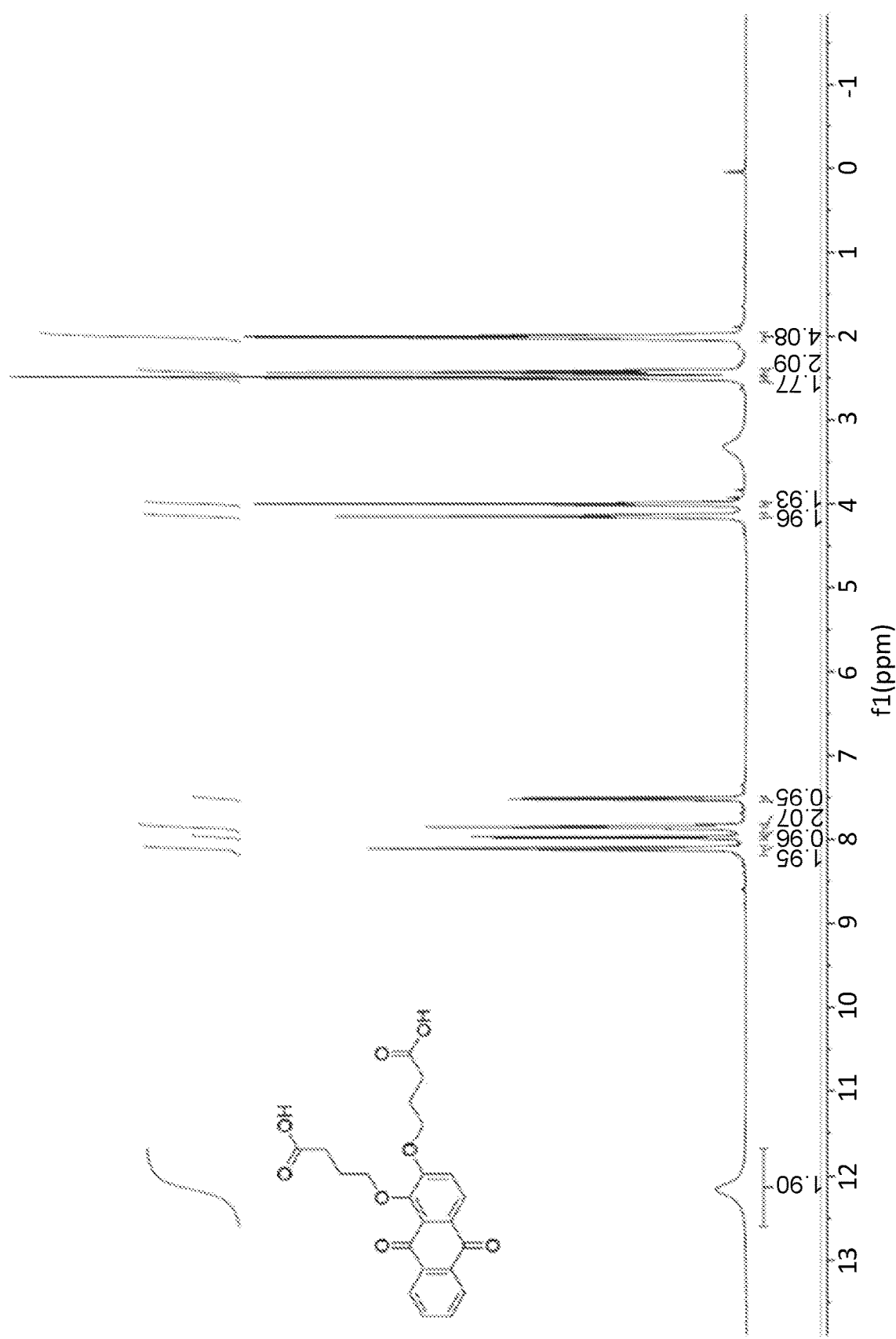
FIG. 3. $^1$H NMR spectrum of 1,2-DBEAQ. 1H NMR (500 MHz, DMSO-d$_6$): δ 12.15 (s, 2H), 8.11 (m, 2H), 7.97 (dd, J=8.6, 1.4 Hz, 1H), 7.85 (m, 2H), 7.51 (d, J=8.7 Hz, 1H), 4.14 (t, J=6.4 Hz, 2H), 4.00 (t, J=6.2 Hz, 2H), 2.51 (t, J=7.4 Hz, 2H), 2.43 (t, J=7.2 Hz, 2H), 2.01 (m, 4H). Final yield: 72.1%.

The $^1$H NMR spectrum of 2,6-DBEAQ is shown in FIG. 1. 1,8- and 1,2-isomers were synthesized similarly, using 1,2-DHAQ and 1,8-DHAQ as precursors. Potassium tert-butoxide (8.16 g, 72.9 mmol) replaced potassium ethoxide to deprotonate the 1,2-DHAQ and 1,8-DHAQ isomers because of the higher p$K_a$ of the hydroxyl groups of these isomers. $^1$H NMR spectra of the final products are shown in FIG. 2 and FIG. 3, respectively, along with their structures.

Solubility limits of all DBEAQ isomers were measured in their oxidized forms by adding the potassium salt of DBEAQ (prepared by reacting DBEAQ with potassium hydroxide in water) until no further solid could be dissolved. After filtering the mixture through a PTFE 0.45 µm syringe filter, a saturated solution of DBEAQ in KOH was obtained. The saturated solution was then diluted by a known amount, and the concentration was evaluated by UV-Vis (Ocean Optics Flame-S Spectrometer Assembly) at 280 and 364 nm. The concentration was calculated according to a pre-calibrated absorbance-concentration curve of known concentrations of DBEAQ. Solubility of the oxygen-sensitive reduced form of DBEAQ was not measured but was assumed to be higher than the oxidized form because: (1) no precipitation after full electrochemical reduction of DBEAQ was observed and (2) increasing the number of negative charges from two for DBEAQ in the oxidized form to four for DBEAQ in the reduced form is expected to make quinone-quinone interactions even more unfavorable and increase its solubility.[2]

After the functionalization, the resulting DBEAQ isomers showed a significant improvement of solubility versus their hydroxyl counterparts at both pH 14 and pH 12. For instance, the room temperature solubility of 2,6-DBEAQ exceeded 1 M in pH 14 and 0.5 M in pH 12 KOH solution (Table 1), as opposed to 0.6 M$^3$ and 0.1 M for 2,6-DHAQ under similar conditions, respectively. Several avenues exist for further increasing reactant solubility and the corresponding energy density, such as the use of mixed cations in the electrolytes[4] or mixtures of different DBEAQ isomers or different molecules with nearly the same reduction potential.

TABLE 1

Effect of pH and counter-ion on maximum solubilities of potassium ferrocyanide, potassium ferricyanide, and 2,6-DBEAQ in KOH. Ranges represent uncertainties in solubility based on different peaks used in UV-Vis calibration measurements.

| Compound | Conditions | Maximum Solubility (M) |
|---|---|---|
| Potassium Ferrocyanide | KOH, pH 14 | 0.5 |
| | KOH, pH 12 | 1.2-1.3 |
| Potassium Ferricyanide | KOH, pH 14 | 1.05-1.13 |
| | KOH, pH 12 | 1.8-2.0 |
| 2,6-DBEAQ | KOH, pH 14 | 1.10 |
| | KOH, pH 12 | 0.60 |

Example 2. Cyclic Voltammetry (CV) of 2,6-DBEAQ

Figure 4A:
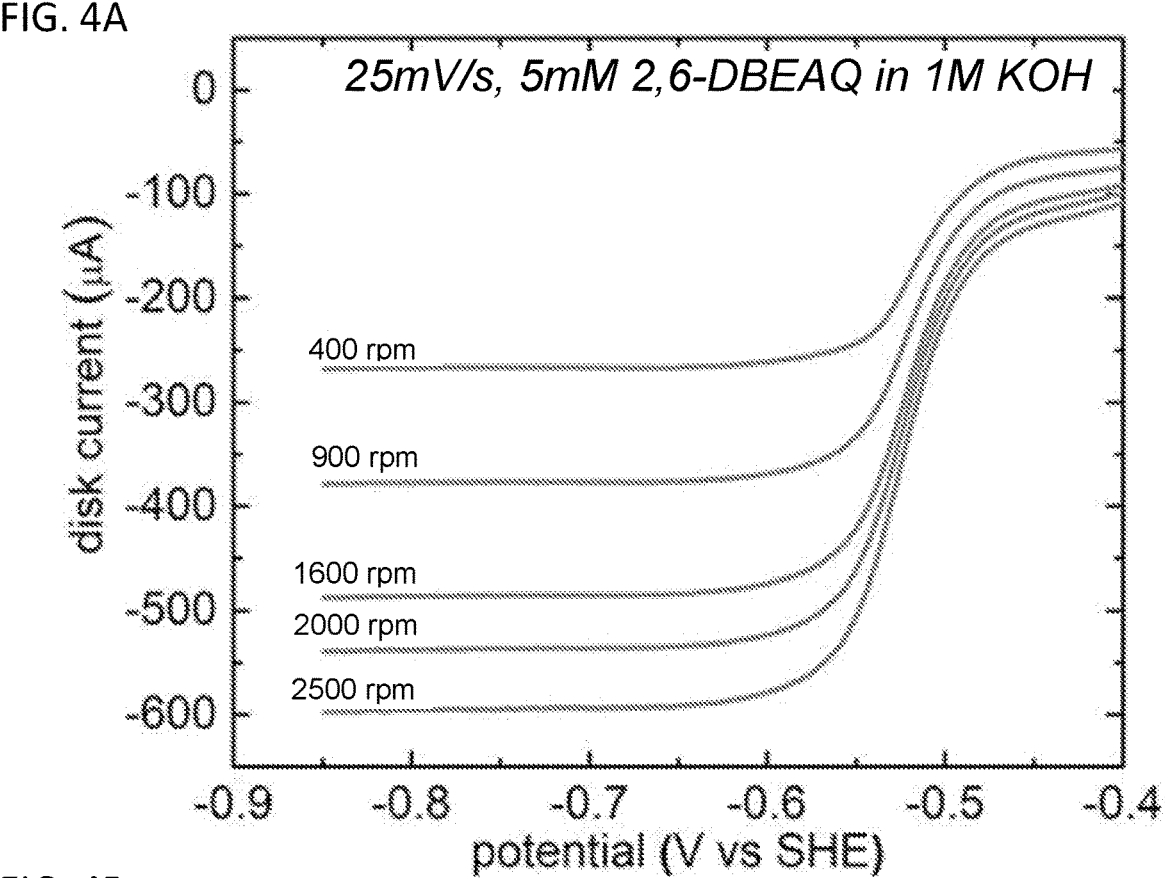
FIGS. 4A-4B. (A) Rotating Disk Electrode study of the reduction of 5 mM 2,6-DBEAQ in 1M KOH on a glassy carbon electrode at rotation rates between 400 and 2500 rpm. (B) Levich plot (limiting current vs. square root of rotation rate in rad/s) of 5 mM 2,6-DBEAQ in 1 M KOH. Data are taken from the current at −0.8 V vs. SHE. The slope yields a diffusion coefficient for the oxidized form of 2,6-DBEAQ of 1.58×10$^{-6}$ cm$^2$/s.
Figure 4B:
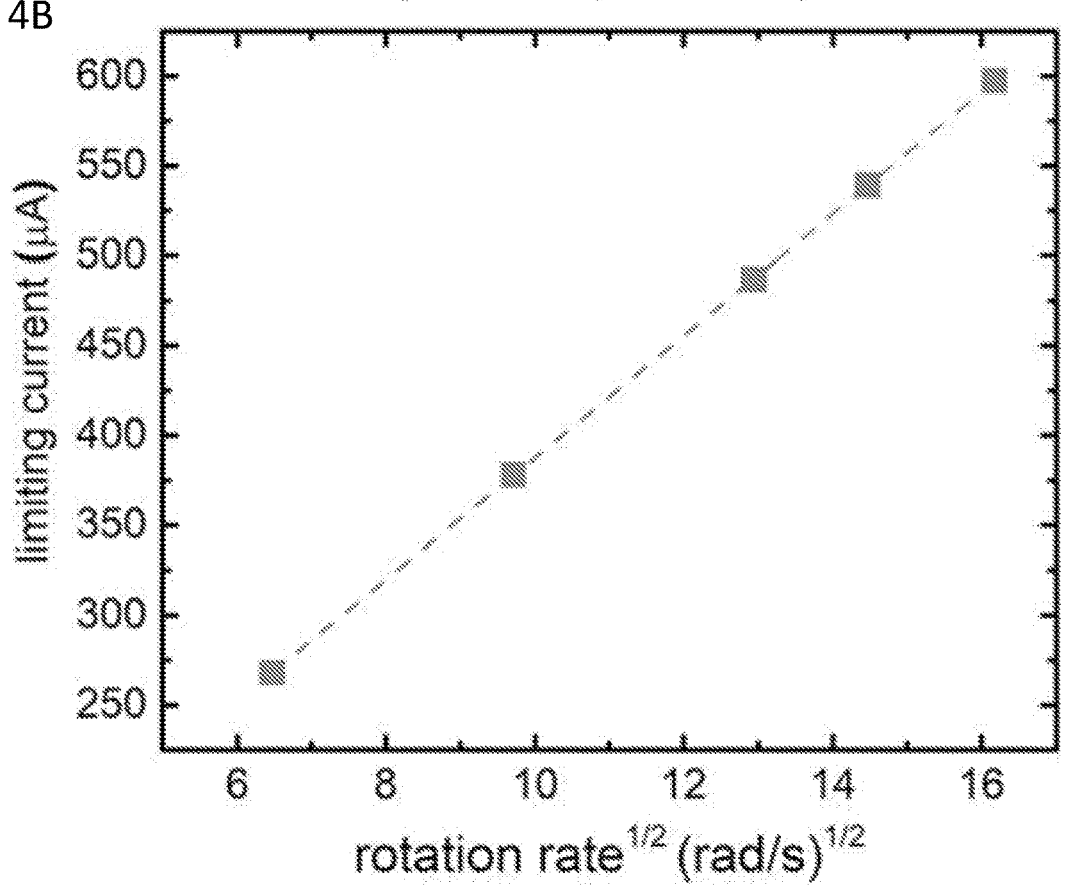

Glassy carbon was used as the working electrode for all three-electrode CV tests. RDE experiments were conducted using a Pine Instruments Modulated Speed Rotator AFMSRCE equipped with a 5 mm diameter glassy carbon working electrode, a Ag/AgCl reference electrode (BASi, pre-soaked in 3 M NaCl solution), and a graphite counter electrode. The electrode was rotated at a specific speed while the voltage was linearly swept from −0.4 to −0.11 V vs. Ag/AgCl (FIG. 4A). The diffusion coefficient of the oxidized form of 2,6-DBEAQ was calculated using the Levich equation, which relates the mass-transport-limited current to the number of electrons transferred (n), the area of the electrode (A), and the concentration of redox-active species in the electrolyte (C), by plotting the mass-transport-limited current against the square root of the rotation rate (FIG. 4B) with the following parameters: n=2, F=96,485 Coulombs/mol, A=0.196 cm$^2$, C=5 mM, kinematic viscosity of 1 M KOH v=1.08×10$^{-6}$ m$^2$/s. The resulting value of the diffusion coefficient for the oxidized form of 2,6-DBEAQ is 1.58×10$^{-6}$ cm$^2$/s.

Figure 5A:
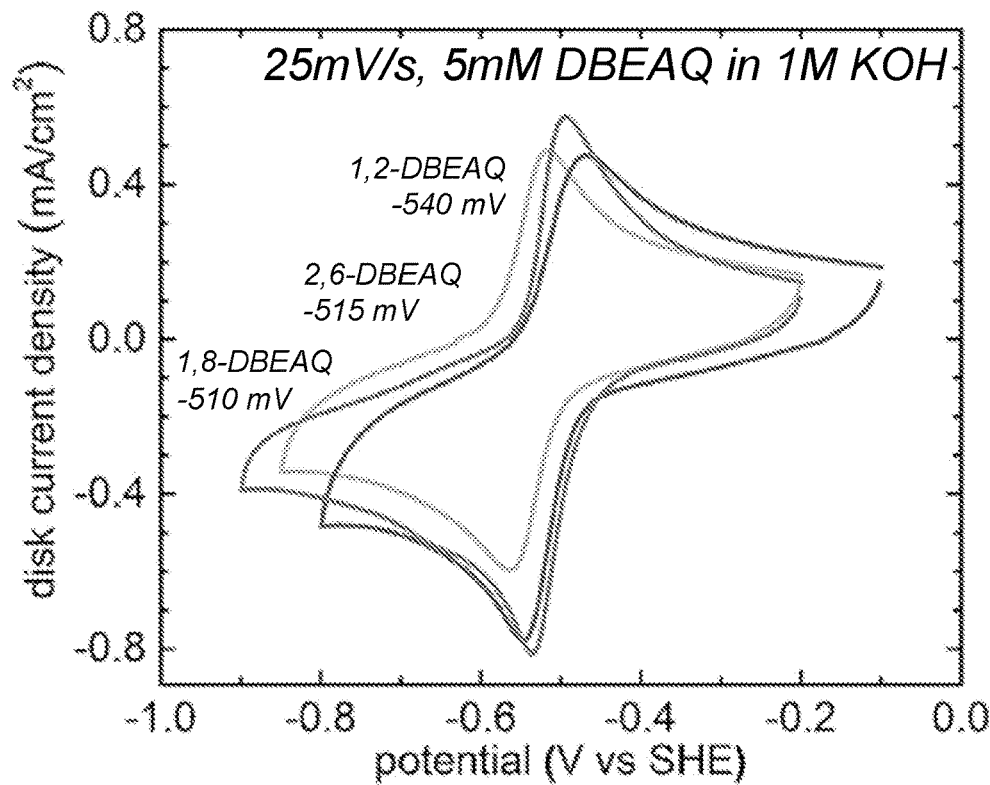
FIGS. 5A-5B. (A) Cyclic voltammogram of 1,2-(blue), 2,6-(gray), and 1,8-(green) DBEAQ. The redox potential versus SHE of each isomer is also indicated. Measurements were made at a scan rate of 25 mV s$^{-1}$. (B) CV of 2,6-DBEAQ. Measurements were made at a scan rate of 10 mV s$^{-1}$ on a polished glassy carbon electrode. The dashed lines indicate the potentials at the peaks in the current density. The arrows indicate the CV scan direction.
Figure 5B:
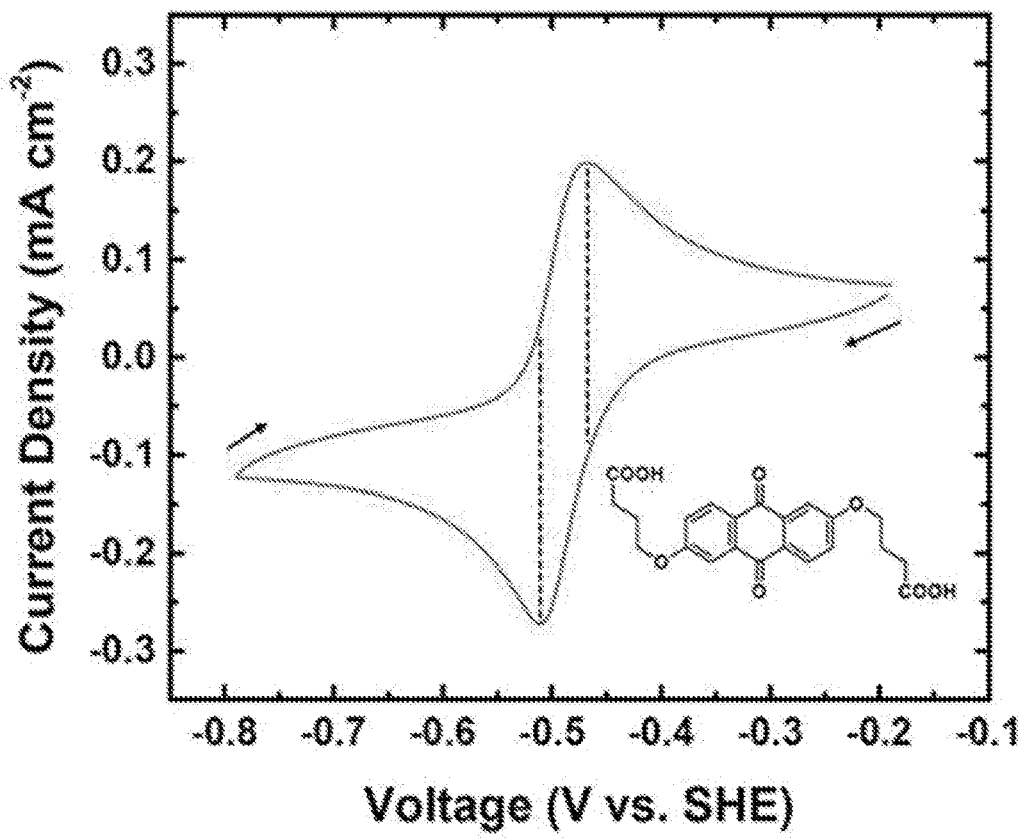
Figure 6:
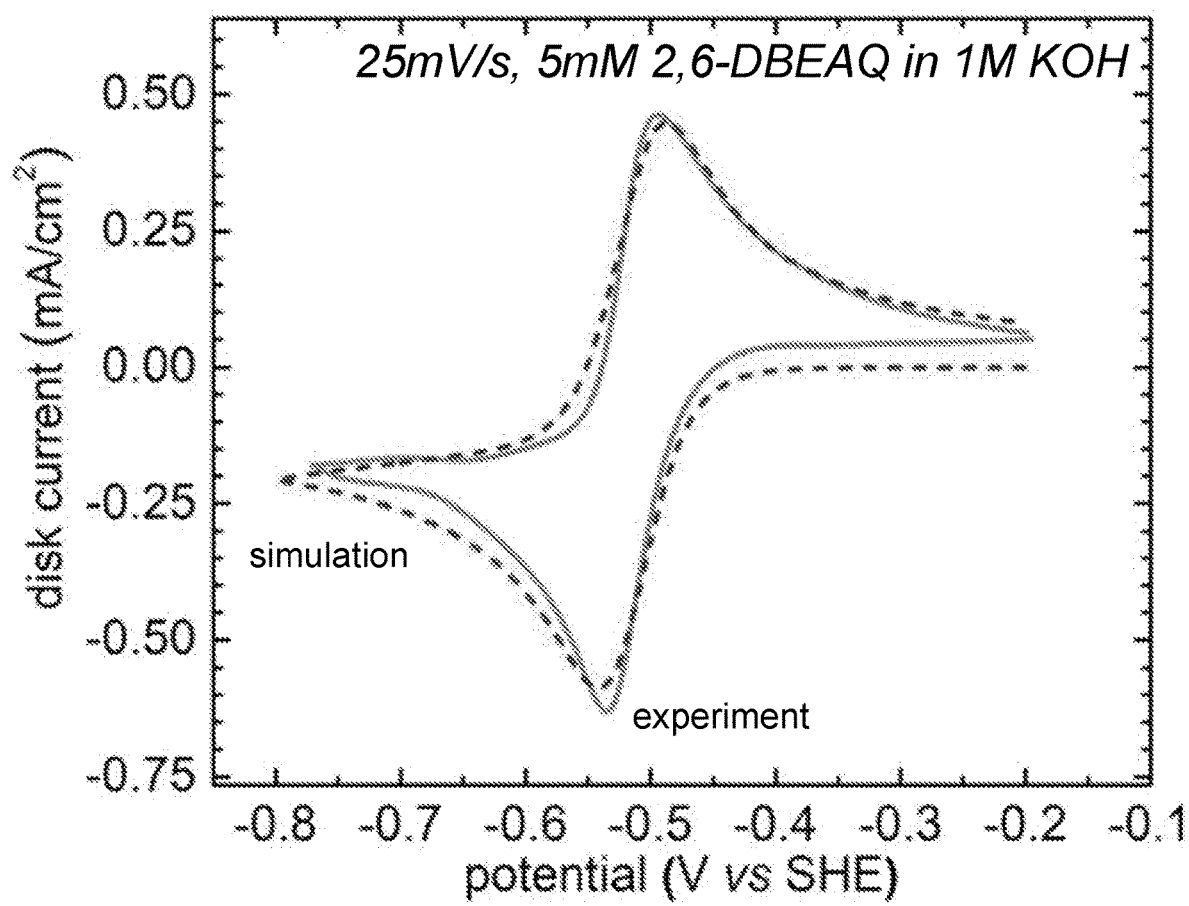
FIG. 6. Capacitance-corrected CV of 5 mM 2,6-DBEAQ in 1 M KOH (solid grey line). The dashed red line represents the simulated total current arising from two successive one-electron reductions with reduction potentials of −0.517 and −0.511 V vs. SHE, according to the procedure outlined in a previous publication.[1] Each simulated reduction has a rate constant k$_o$=7×10$^{-3}$ cm/s and α=0.5. The diffusion coefficient of all redox states of 2,6-DBEAQ (oxidized, semiquinoid, and reduced) was assumed to be 1.58×10$^{-6}$ cm$^2$/s.
Figure 7:
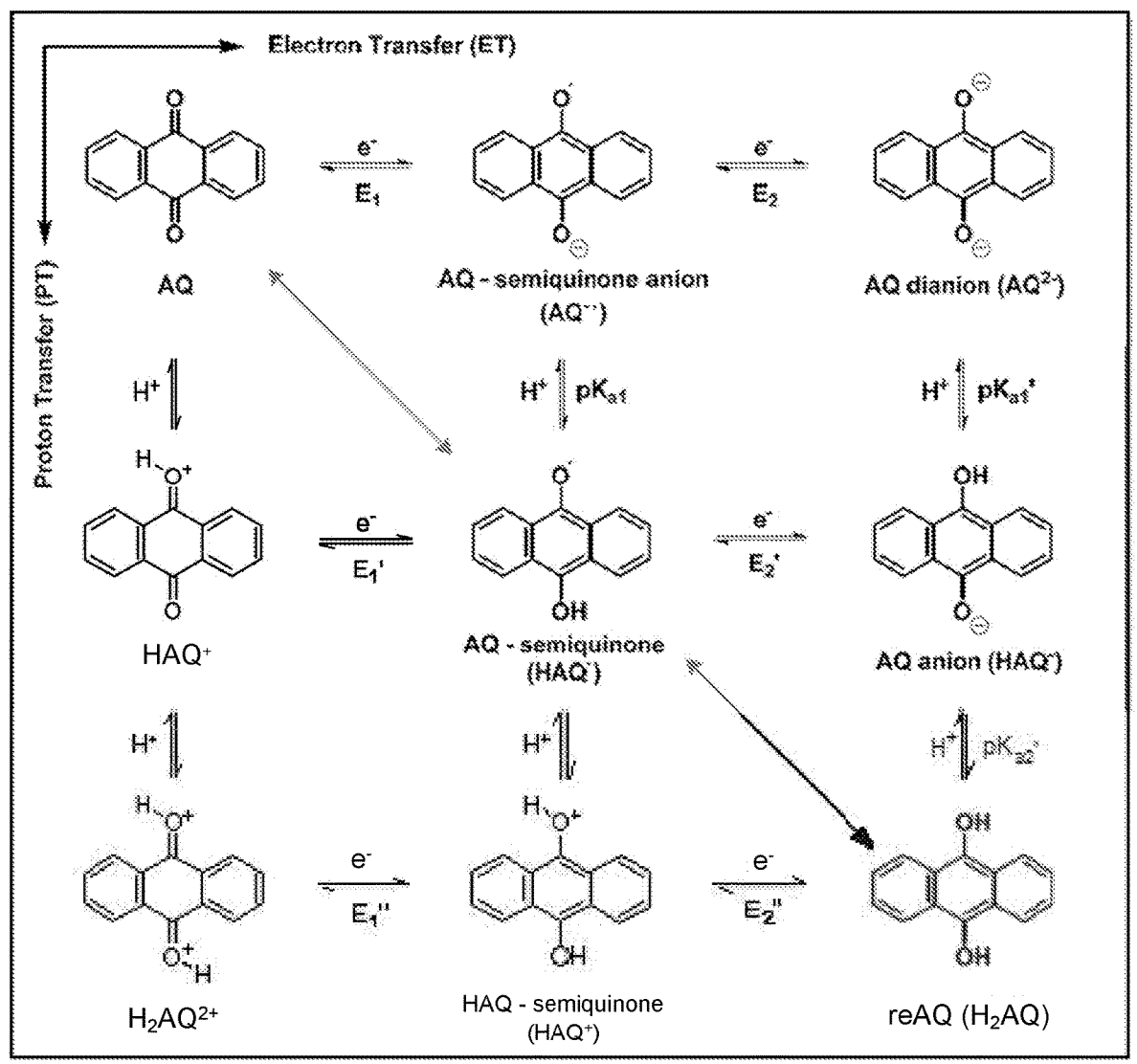
FIG. 7. 9-membered Square Scheme of AQ Reduction. The horizontal direction indicates electron transfer onto the molecule at a given potential, i.e., E$_1$ and E$_2$, and the vertical direction indicates protonation of the species depending on the pK$_a$ of the generated anion and the solution pH. AQ states that are unstable under alkaline conditions are shown in grey. Blue arrows indicate PCET.

A first CV experiment was performed in which 2,6-DBEAQ was dissolved in pH 14 KOH solution at a concentration of 5 mM. CV measurements were plotted in FIG. 5A and include results for the isomers of 2,6-DBEAQ. All DBEAQ isomers showed very similar redox potential between −510 and −540 mV vs. SHE, which would yield battery voltages above 1 V versus ferri-/ferrocyanide posolyte. Despite the increase in reduction potential compared with 2,6-DHAQ (−680 mV vs. SHE), their CVs exhibited high reversibility with redox peaks ~40 mV apart, much smaller than the ~90 mV value from 2,6-DHAQ.[3] A Levich analysis was used to obtain the diffusion coefficient of the oxidized form of 2,6-DBEAQ (1.58×10$^{-6}$ cm$^2$/s, FIGS. 4A-4B), which was then used in a CV simulation of its redox kinetics (FIG. 6). The results show, in agreement with an analogous study of the 2,6-DHAQ CV, that the peak shape and separation is consistent with two one-electron reduction steps at different potentials, $E_1$ and $E_2$, whose values are modulated by the energetics of semiquinone reduction (FIG. 7). In comparison with 2,6-DHAQ, which exhibited an $E_1$-$E_2$ separation of 60 mV[3], the 2,6-DBEAQ CV exhibits a much smaller $E_1$-$E_2$ separation of 6 mV, implying that 2,6-DHAQ is more thermodynamically susceptible to the formation of semiquinone radicals than is 2,6-DBEAQ.

A second CV experiment was performed in which 2,6-DBEAQ was dissolved in pH 14 KOH solution at a concentration of 2 mM. CV measurements were plotted in FIG. 4C. The standard equilibrium potential was determined to be −0.49 V vs. SHE. The separation between the peaks in the CV curves was 42 mV, indicating fairly rapid and reversible electrochemical reactions at the surface of the electrodes.

Example 3. Theoretical Calculations of DBEAQ Isomer Susceptibility to Alkyl Chain Cleavage The stability of disubstituted DBEAQ isomers against the loss of the alkyl groups was evaluated computationally. The first approach taken was to evaluate the relative reaction energies of the loss of the alkyl chain of both the oxidized and reduced forms of different isomers of DBEAQ. These reactions are shown in Scheme 3.

Scheme 3.
Reaction energies evaluated to determine the relative thermodynamic stability of different isomers of DBEAQ in different oxidation states

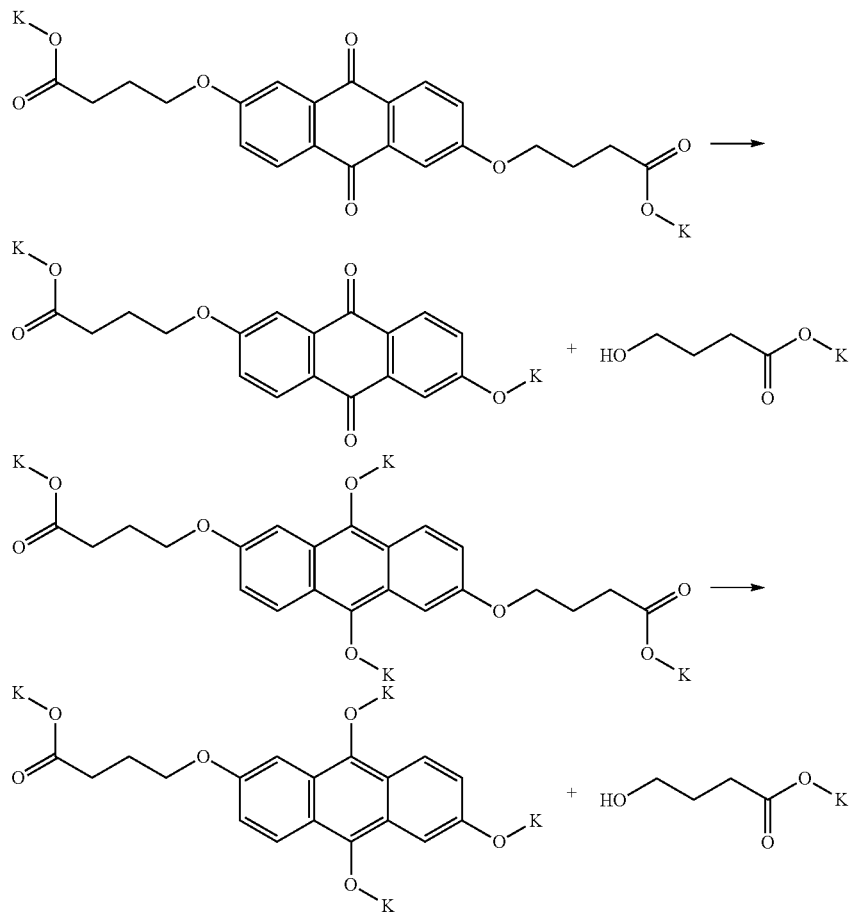

Optimizations were conducted at the PM7 level of theory with the COSMO solvation model using the MOPAC package.[5] Up to 20 conformers for each molecule were generated using RDKit.[6] Because the molecule is in alkaline conditions, the energies were evaluated for the deprotonated forms where explicit potassium cations are placed near the negative charges. The relative energies are shown in Table 2. Two important observations from these results are: (1) the reaction energies associated with chain loss are more thermodynamically favorable for the oxidized form in all cases, except in 2,6-DBEAQ, where the reduced form is slightly more susceptible. Second, the thermodynamic stability of both the oxidized and reduced forms of 2,6-DBEAQ are among the highest of all the isomers examined.

TABLE 2

Relative Energies of DBEAQ.

| DBEAQ Chain Positions | Thermodynamic Loss of Chain (eV) | | Reaction Energy to form Tetrahedral Intermediate (eV) From Oxidized Form[a,c] |
|---|---|---|---|
| | Oxidized Form[a,b] | Reduced Form[a,b] | |
| 2,6 | 0.00 | −0.06 | 0.00 |
| 1,2 | −0.38 | −0.19 | −0.21 |

TABLE 2-continued

Relative Energies of DBEAQ.

| DBEAQ Chain Positions | Thermodynamic Loss of Chain (eV) | | Reaction Energy to form Tetrahedral Intermediate (eV) From Oxidized Form[a,c] |
|---|---|---|---|
| | Oxidized Form[a,b] | Reduced Form[a,b] | |
| 1,3 | −0.27 | −0.09 | −0.38 |
| 1,4 | −0.33 | 0.03 | −0.20 |
| 1,5 | −0.32 | −0.13 | −0.35 |
| 1,6 | −0.35 | 0.00 | −0.29 |
| 1,7 | −0.56 | −0.21 | −0.21 |
| 1,8 | −0.34 | 0.02 | −0.27 |
| 2,3 | −0.30 | 0.71 | −0.21 |
| 2,7 | 0.00 | 0.86 | −0.04 |

[a]Energies calculated at the PM7 level of theory with the COSMO solvation model;
[b]Reaction energies are tabulated relative to the energy of 2,6-DBEAQ losing an alkyl chain in its oxidized form;
[c]Reaction energies to form tetrahedral intermediate are relative to the reaction energy for the oxidized form of 2,6-DBEAQ to form a tetrahedral intermediate.

Because the relative stability of the reduced form over the oxidized form cannot be completely explained by looking at only the thermodynamics of the final products, we investigated the thermodynamic landscape of possible intermediates. As the oxidized form is more electron deficient, we estimate the susceptibility to chain loss by evaluating the energy of a hydroxide-substituted intermediate of the DBEAQ molecule (Scheme 4). This intermediate should more easily form for the oxidized form. As done previously with bromination of anthraquinones,[7] the energy is estimated by evaluating the relative energy of the tetrahedral intermediate to that of the oxidized molecule (right-most column of Table 2). Here, we see that 2,6-DBEAQ is the most stable isomer, whereas 1,2- and 1,8-DBEAQ are less stable than 2,6-DBEAQ, which is consistent with experimental observation. Based on these findings, it appears that DBEAQ stability against alkyl chain loss is highly sensitive to the exact positioning of the two alkyl chains, particularly with respect to the ketone groups on the anthraquinone core.

DBEAQ concentration being used in both electrolytes. 7.5 mL of 2,6-DBEAQ was fully reduced (i.e., charged to 100% state of charge, or SOC) against a posolyte of excess potassium ferrocyanide and then mixed with 7.5 mL of oxidized 2,6-DBEAQ (0% SOC) to afford a 2,6-DBEAQ electrolyte at 50% SOC. 5 mL of the resulting electrolyte was used as the capacity-limiting side of a volumetrically unbalanced compositionally-symmetric cell, while the remaining 10 mL was used as the non-capacity-limiting side, i.e., with twice the nominal capacity of the capacity-limiting side. The capacity-limiting side was then cycled potentiostatically between 0 and ~100% SOC with potential limits of ±0.2 V versus the non-capacity limiting side, switched when Scheme 4.
Reaction of OH⁻ with oxidized form to form tetrahedral intermediate. Used as a means of estimating the vulnerability of the oxidized form to decompositon

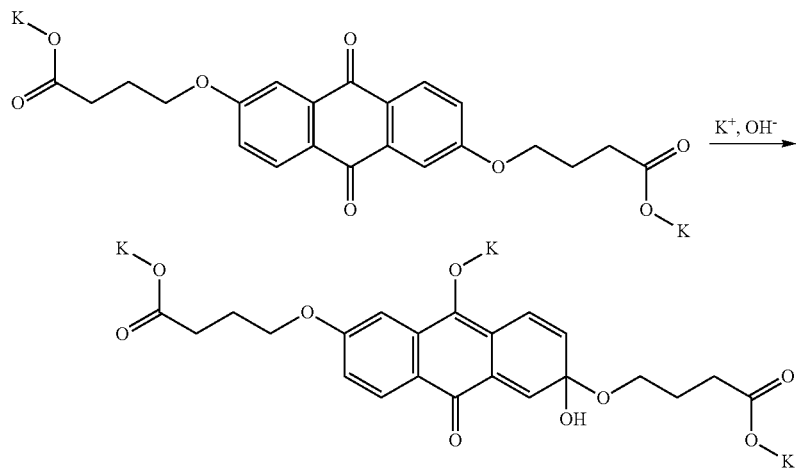

Example 4. Temporal Cycling of with 2,6-DBEAQ 2,6-DBEAQ has superior chemical stability over other quinones reported to date, notably including 2,6-DHAQ. As a direct probe of the effect of O-alkylation of anthraquinone on its chemical stability, 2,6-DBEAQ was cycled potentiostatically in a volumetrically unbalanced compositionally-symmetric cell configuration. The symmetric cell configuration, in which the two sides have the same electrolyte composition, is a simple and direct probe of chemical and electrochemical stability of redox flow battery reactants.[8] Any observed capacity fade is directly related to deactivation of the reactant on the capacity-limiting side in either its oxidized or reduced state because (1) there is negligible reactant crossover with symmetric compositions; (2) changes to membrane resistance do not result in temporal capacity variations in potentiostatic cycling; and (3) the unbalanced volumes permit the capacity-limiting side to be taken to its limiting states of charge despite potential side reactions.

Potentiostatic symmetric cell cycling was performed according to a reported procedure[8] in order to assess the temporal chemical stability of DBEAQ, independent of any variations in apparent capacity as a result of changes to membrane resistance, and in a configuration where there is negligible water or reactant crossover due to the same the absolute value of the current density decayed to 2 mA/cm², which is ~3× higher than the background current.

Full cell cycling (i.e. with a ferro/ferricyanide-based posolyte) was performed with the same flow cell hardware but with a FUMASEP® E-620(K) membrane due to its high conductivity and low permeability of DBEAQ and ferricyanide compared to other membranes. For studies at pH 14, the posolyte volume was 30 mL, and its composition, when assembled, was 0.20 M potassium ferrocyanide, 0.08 M potassium ferricyanide, and 1 M KOH. The negolyte was prepared by dissolving 0.1 M 2,6-DBEAQ in its oxidized form in 1.2 M KOH solution, resulting in 0.1 M 2,6-DBEAQ, 1.2 M K+, and 1 M OH⁻ electrolyte solution. For studies at pH 12, both electrolytes comprised 10 mM OH⁻; the pH was checked both with a pH meter and pH paper and adjusted where necessary. For all full cell studies, the negolyte was assembled in the fully discharged state. Galvanostatic cycling was performed at ±0.1 A/cm² at room temperature, with voltage limits of 0.6 and 1.4 V. To obtain the polarization curves, the cell was first charged to the desired state of charge and then polarized via linear sweep voltammetry at a rate of 100 mV/s. This method was found to yield polarization curves very close to point-by-point galvanostatic holds, yet to impose minimal perturbation to the SOC of the small-electrolyte-volume cell. Electrochemical impedance spectroscopy (EIS) was performed at SOCs between 10 and 100% at open-circuit potential with a 10 mV perturbation and with frequency ranging from 1 to 300,000 Hz.

Figure 8A:
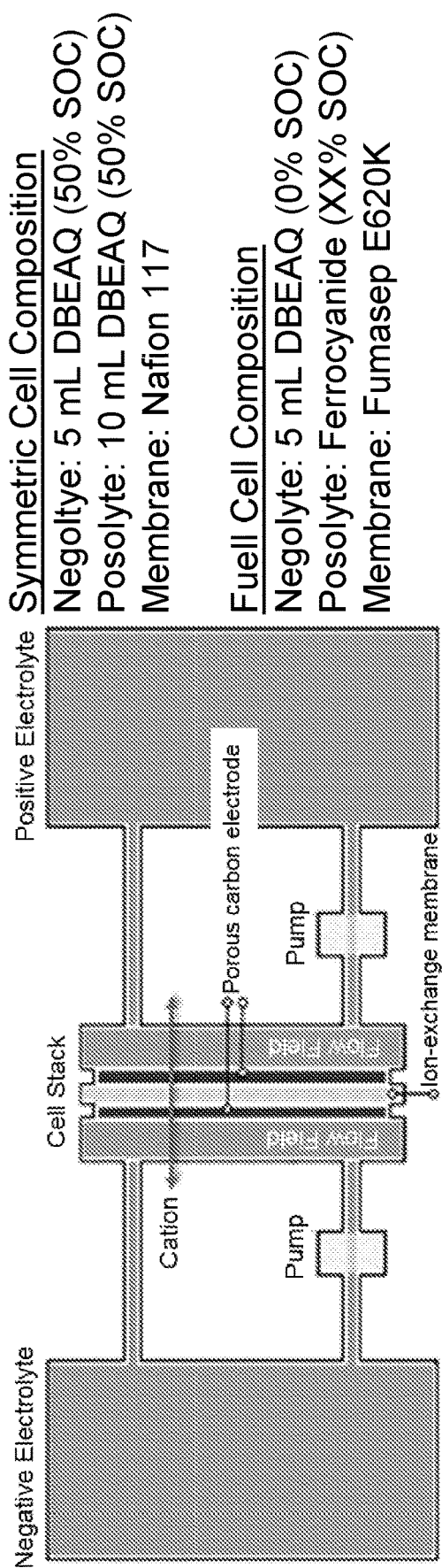
FIGS. 8A-8C. (A) Cell schematic for unbalanced compositionally symmetric cell cycling and full cell cycling. (B) Unbalanced compositionally symmetric cell cycling of 0.1 M 2,6-DBEAQ showing capacity as a function of time. Inset in the plot is the temporal capacity fade rate from a linear fit of the first 5 days of cycling. (C) Unbalanced compositionally symmetric cell cycling of 0.65 M 2,6-DBEAQ capacity as a function of time. Inset in the plot is the temporal capacity fade rate from a linear fit of the first 5 days of cycling. In both (B) and (C), the capacity-limiting side was 5 mL 2,6-DBEAQ while the non-capacity-limiting side was 10 mL 2,6-DBEAQ, both at pH 14. Capacities were obtained by full potentiostatic reduction and oxidation at +/−0.2 V of the capacity-limiting side; the potential was switched when the magnitude of the current density decayed to 2 mA/cm$^2$. Note that the y-axis scales in (B) and (C) represent about 2% of the capacity of the capacity-limiting side.
Figure 8B:
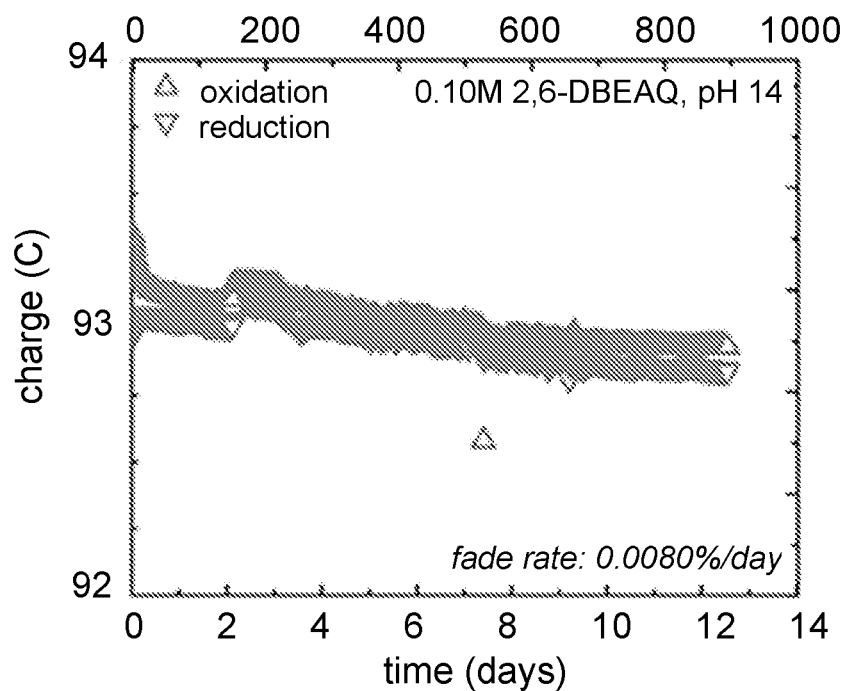
Figure 8C:
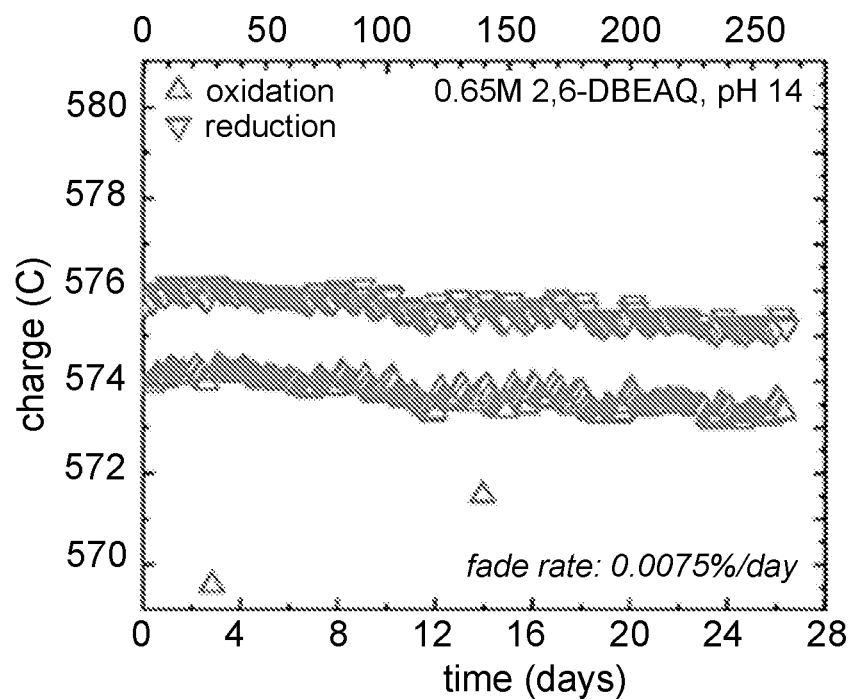
Figure 9:
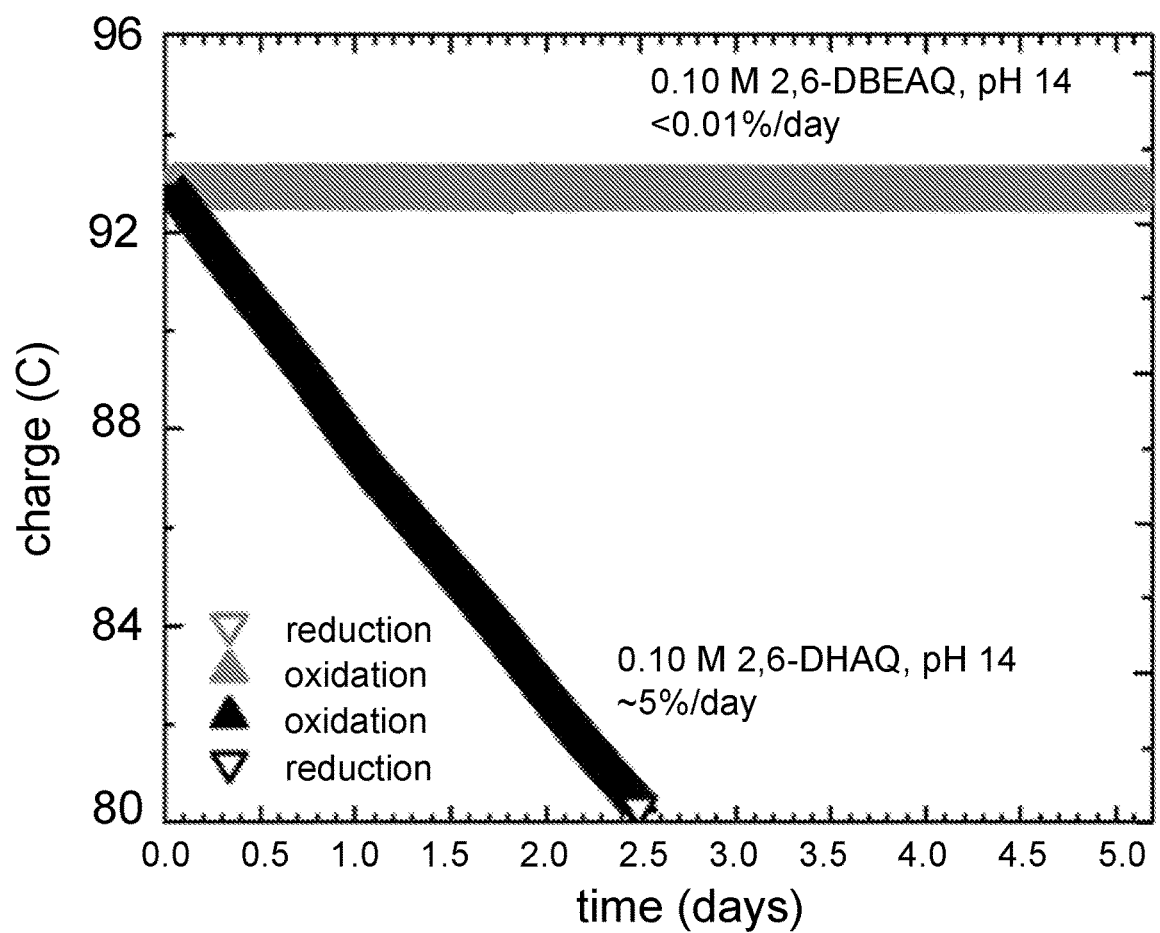
FIG. 9. Unbalanced compositionally-symmetric cell cycling of 0.10 M 2,6-DBEAQ and 2,6-DHAQ, showing capacity vs. time, both in 1 M KOH (pH 14). The capacity-limiting side was 5 mL 0.1 M 2,6-DBEAQ or DHAQ, while the non-capacity-limiting side was 10 mL of the same. Capacities were obtained by full potentiostatic reduction and oxidation of 5 mL of capacity-limiting side; potential was switched between ±0.2 V when magnitude of current dropped to 2 mA/cm$^2$. Cell cycle period is ~20 min.
Figure 12:
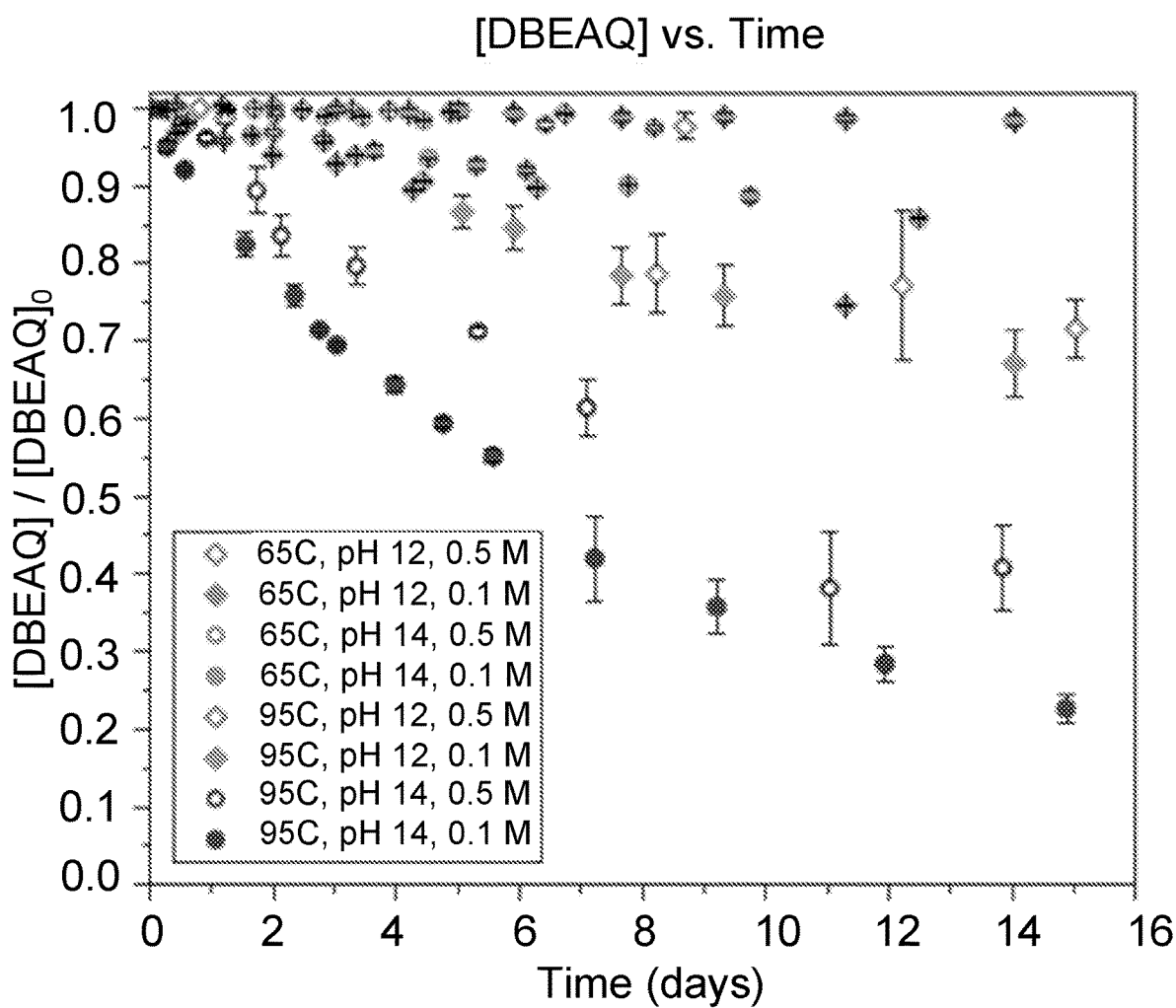
FIG. 12. Time course of 2,6-DBEAQ decomposition at various temperature, pH, and concentration conditions. The remaining concentration of 2,6-DBEAQ relative to the initial concentration vs. time (in days) for samples treated at 65° C. and 95° C., at pH 12 and pH 14, and at 0.1 M and 0.5 M concentration in the oxidized form.
Figure 13A:
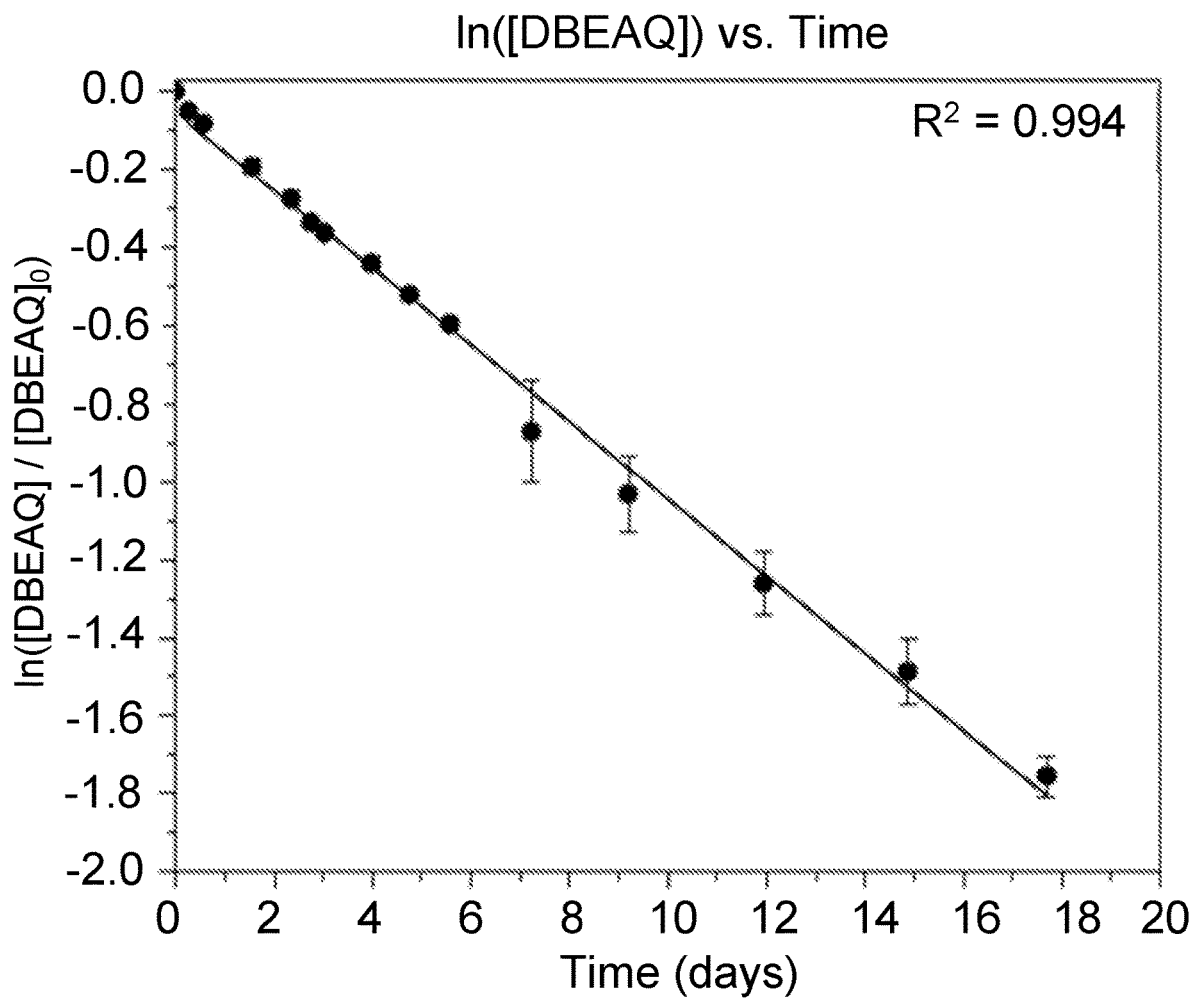
FIGS. 13A-13C. Evidence of pseudo-first order decomposition kinetics with respect to 2,6-DBEAQ. The remaining concentration of 2,6-DBEAQ relative to the initial concentration vs. time (in days) for samples treated at 95° C., at pH 14, and at 0.1 M concentration in the oxidized form, plotted (A) on a semi-logarithmic scale; (B) on a linear scale; (C) as the reciprocal of the 2,6-DBEAQ concentration relative to the initial concentration vs. time.
Figure 13B:
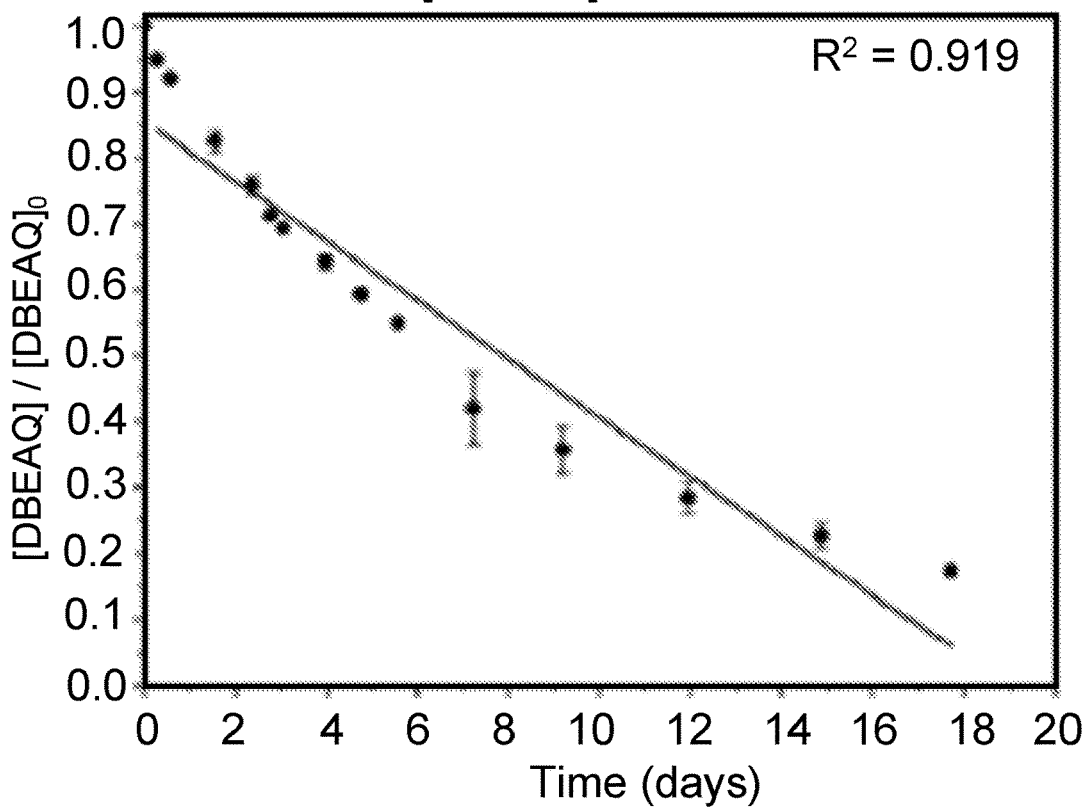
Figure 13C:
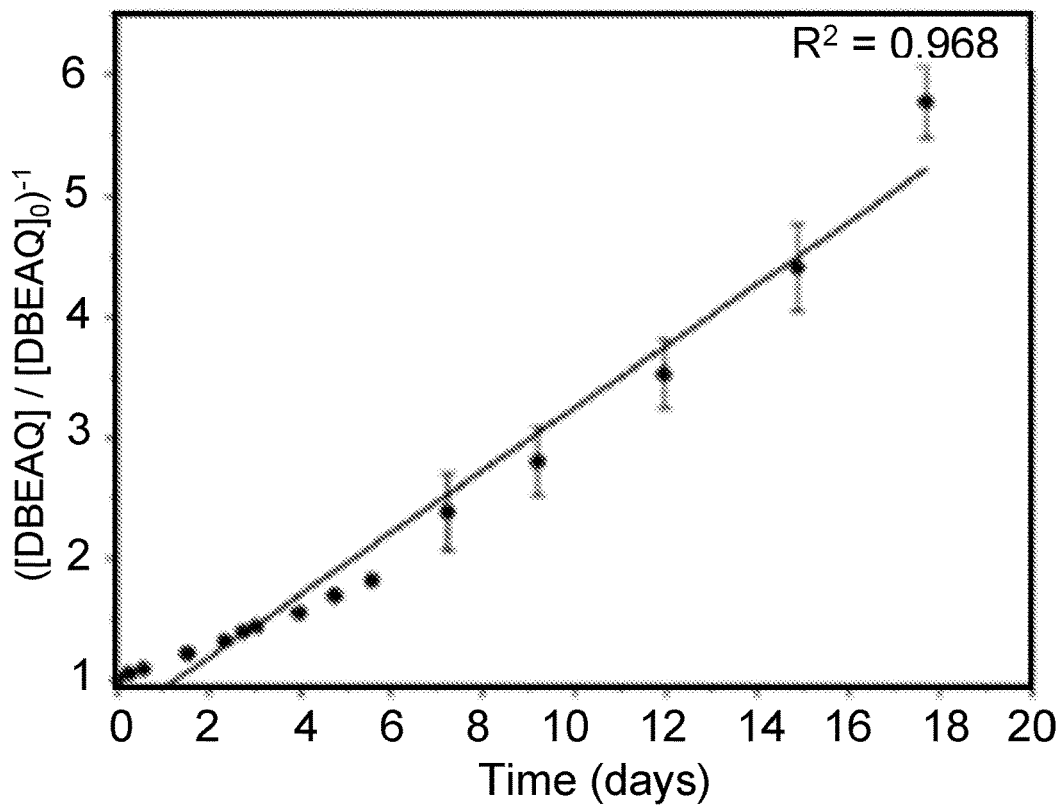

FIG. 8A shows a schematic of the cell setup and the results of unbalanced compositionally-symmetric cell cycling for 2,6-DBEAQ at 0.10 and 0.65 M for durations of 13 and 26 days, respectively (FIGS. 8B and 8C). In both cases, 2,6-DBEAQ exhibited temporal capacity fade rates of <0.01%/day or <3.0%/year, which suggests a loss mechanism that is first order in 2,6-DBEAQ concentration. In contrast, 2,6-DHAQ cycled in a similar cell configuration demonstrated a much higher temporal fade rate of 5%/day (FIG. 9). Temporal capacity fade rates for neutral organic/ organometallic RFBs have been summarized elsewhere.[9] Most systems show fade rates in the range of 0.1-3.5%/day. The temporal fade rate of 2,6-DBEAQ is the lowest ever reported for a quinone-based electrolyte, with the lowest previously reported being for 9,10-anthraquinone-2,6-disulfonate (AQDS) at 0.1-0.2%/day.[10,11] It is on par with that of a recently reported viologen-based flow battery,[9] which exhibited the highest capacity retention rate for any flow battery in the absence of rebalancing processes, with a temporal capacity fade rate of <0.01%/day in symmetric cell testing.[8]

The origin of the higher chemical stability of 2,6-DBEAQ as compared to 2,6-DHAQ is not completely understood; however, we highlight here a few key distinctions that may be responsible. Notably, it is the reduced form of 2,6-DHAQ that has been shown in a previous study to be involved in the loss of redox activity, whereas the reduced form of 2,6-DBEAQ is shown here to be quite stable even at temperatures up to 95° C. Our first observation is that, because the redox potential of 2,6-DBEAQ is ~200 mV higher than that of 2,6-DHAQ, 2,6-DBEAQ should be more stable thermodynamically in its reduced form. Secondly, at high pH, we expect both the reduced hydroquinone core and solubilizing groups to be deprotonated and therefore negatively charged in both molecules. The closer proximity of the negatively charged deprotonated hydroxyl groups in 2,6-DHAQ should lead to a larger intramolecular Coulombic repulsion force, which may contribute to this destabilization of the reduced form of the molecule. Finally, the greater susceptibility to the formation of semiquinone radicals in 2,6-DHAQ, as discussed above, may also be involved in its decreased stability.

The alkyl chain functionalization, while drastically improving lifetime, does not avoid decomposition altogether. By performing elevated temperature chemical stability studies, we have identified that the cleavage of γ-hydroxybutyrate is involved in the decomposition of the oxidized form of 2,6-DBEAQ (FIGS. 10A-10C and FIGS. 11A-11D), and we have characterized the time course of γ-hydroxybutyrate cleavage at pH 12 and pH 14 and at 0.1 M and 0.5 M concentration (FIG. 12 and FIGS. 13A-13C). The results suggest that the half-life of 2,6-DBEAQ at room temperature, pH 14, and 0.1 M concentration in the oxidized form is on the order of 5 years, with substantially slower decomposition in the reduced form relative to the oxidized form and at pH 12 relative to pH 14; these observations are consistent with long redox flow battery lifetime at typical operating cell conditions.

Example 5. Membrane and Full Cell Studies Using 2,6-DBEAQ

Figure 14A:
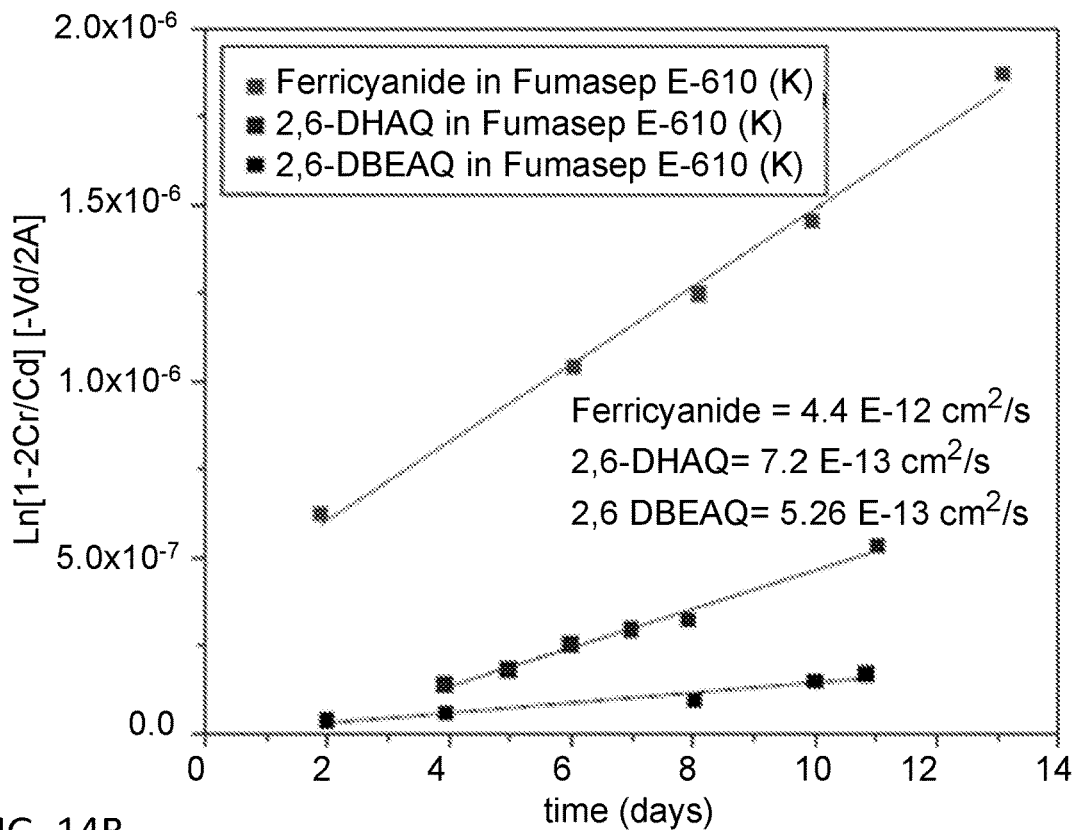
FIG. 14A-14B. (A) The permeability of the oxidized form of 2,6-DBEAQ, 2,6-DHAQ, and potassium ferricyanide across a FUMASEP® E-610 (K) membrane. (B) 2,6-DHAQ in Nafion 212 and FUMASEP® E-610 (K). The slope represents the permeability.
Figure 14B:
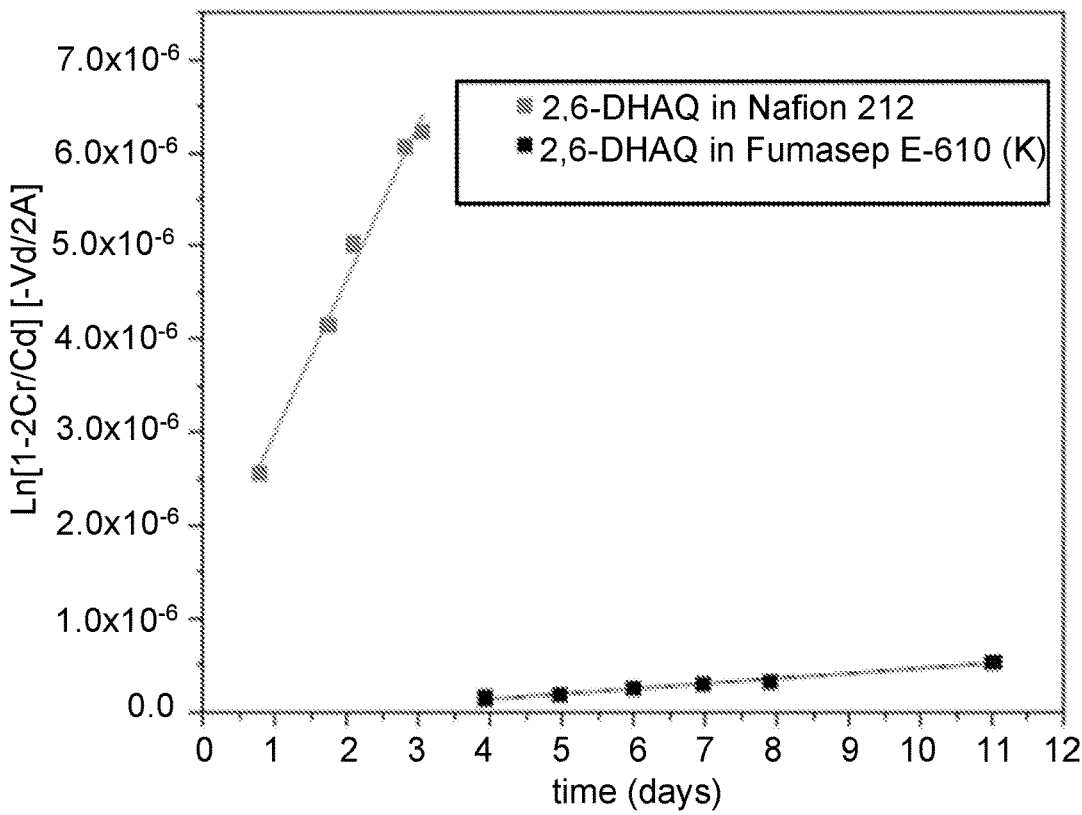
Figure 15:
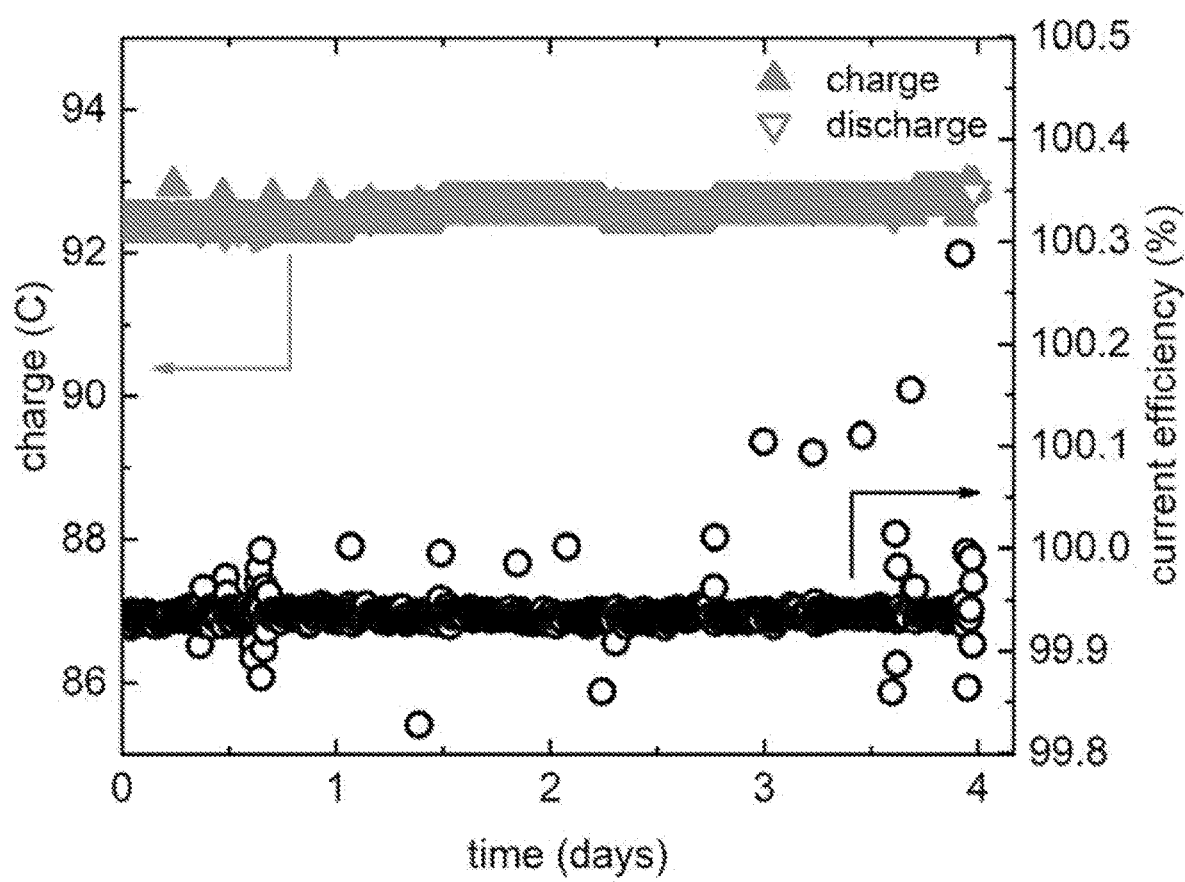
FIG. 15. Capacity and current efficiency (capacity on discharge divided by the capacity of the preceding charge step) as functions of time during galvanostatic cycling of a cell with a negolyte of 5.5 mL 0.1 M 2,6-DBEAQ and posolyte of 15 mL 0.20 M potassium ferrocyanide and 0.08 M potassium ferricyanide, both at pH 14 (880 cycles with each cycle 6.5 minutes long). Galvanostatic cycling was performed at 100 mA/cm$^2$ with voltage cutoffs of 1.4 and 0.6 V on charge and discharge, respectively.

Ion-conductive membranes play a critical role in RFB systems in governing the transport of counter ions across the membranes (ionic conductivity) and the simultaneous transport of redox-active species (membrane crossover). In a compositionally-asymmetric cell, e.g. 2,6-DBEAQ-ferrocyanide system, capacity fade rate can be greatly exacerbated by the irrecoverable crossover of the reactant to the other side of the electrolyte.[12] To limit capacity fade by this mechanism, while retaining high permselectivity, we surveyed a range of cation-exchange membranes, including the industry standard NAFION®-based perfluorosulfonic acid (PFSA) membranes, by characterizing both their $K^+$ conductivity and permeability of 2,6-DBEAQ and ferricyanide (more permeable than ferrocyanide). FUMASEP® E-600 series membranes, which comprise a non-fluorinated, sulfonated polyaryletherketone-copolymer backbone, delivered the best performance. The membrane displayed a low area specific resistance (ASR) of ~1 Ω·cm$^2$ in 1 M $K^+$ solution, which is comparable to Nafion 212. It also showed an extremely low 2,6-DBEAQ and ferricyanide permeability of $5.26 \times 10^{-13}$ cm$^2$/s and $4.4 \times 10^{-12}$ cm$^2$/s, respectively (FIGS. 14A-14B), which are at least an order of magnitude lower than Nafion 212 systems. To further prove the low permeability of redox-active species, we constructed a low concentration 2,6-DBEAQ-ferri/ferrocyanide full cell at pH 14, using a FUMASEP® E-620(K) membrane. Over a period of 4-day (~880 cycles) galvanostatic cycling testing, the cell showed immeasurably low capacity fade and a current efficiency around ~99.94% (FIG. 15). The low 2,6-DBEAQ permeabilities measured ex situ using the nutating table setup translate to negligible crossover of 2,6-DBEAQ in an operating cell, and additional contributions to crossover that are not present in the nutating table tests, such as electromigration and pressure from active pumping of electrolytes[13], are unimportant. These low permeabilities, together with the fact that FUMASEP® E-600-series membranes do not contain fluorine, implies that their use in a DBEAQ-ferri/ferrocyanide full cell affords a potentially robust configuration for a long-lasting RFB with low power cost (in $/kW) for fully installed systems.

Figure 16A:
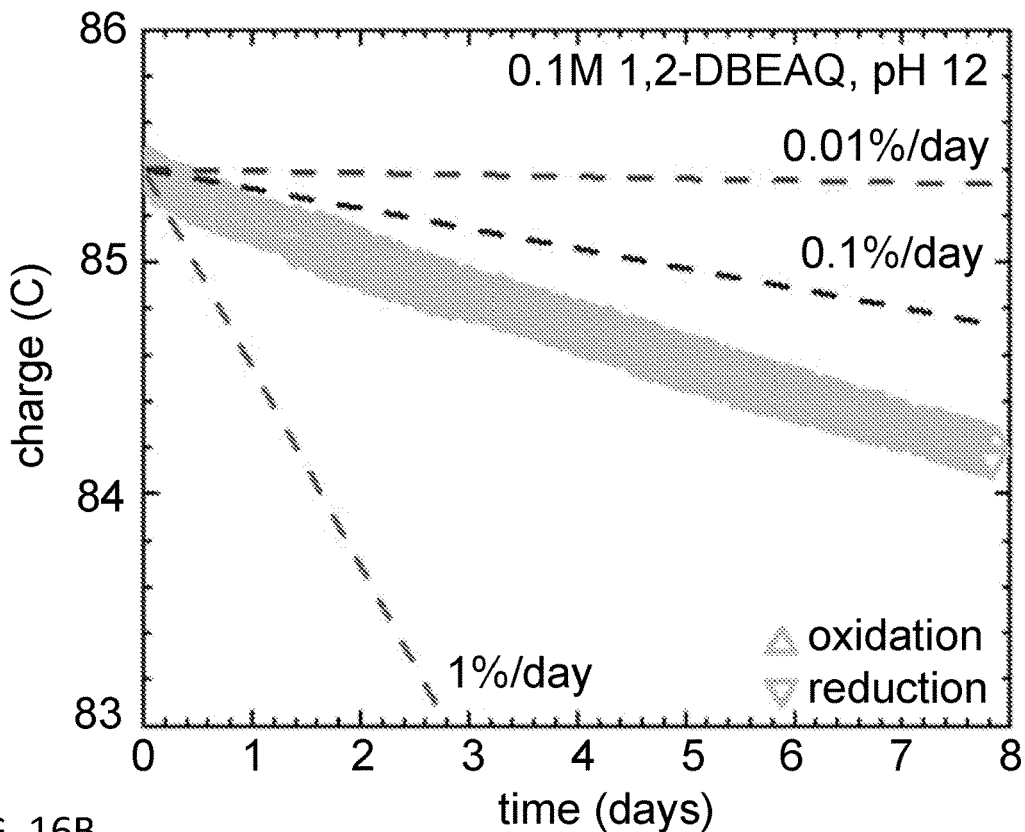
FIG. 16A-16B. Unbalanced compositionally-symmetric cell cycling of 0.10 M (A) 1,2- and (B) 1,8-DBEAQ, showing capacity vs. time, both in 0.01 M KOH (pH 12).
Figure 16B:
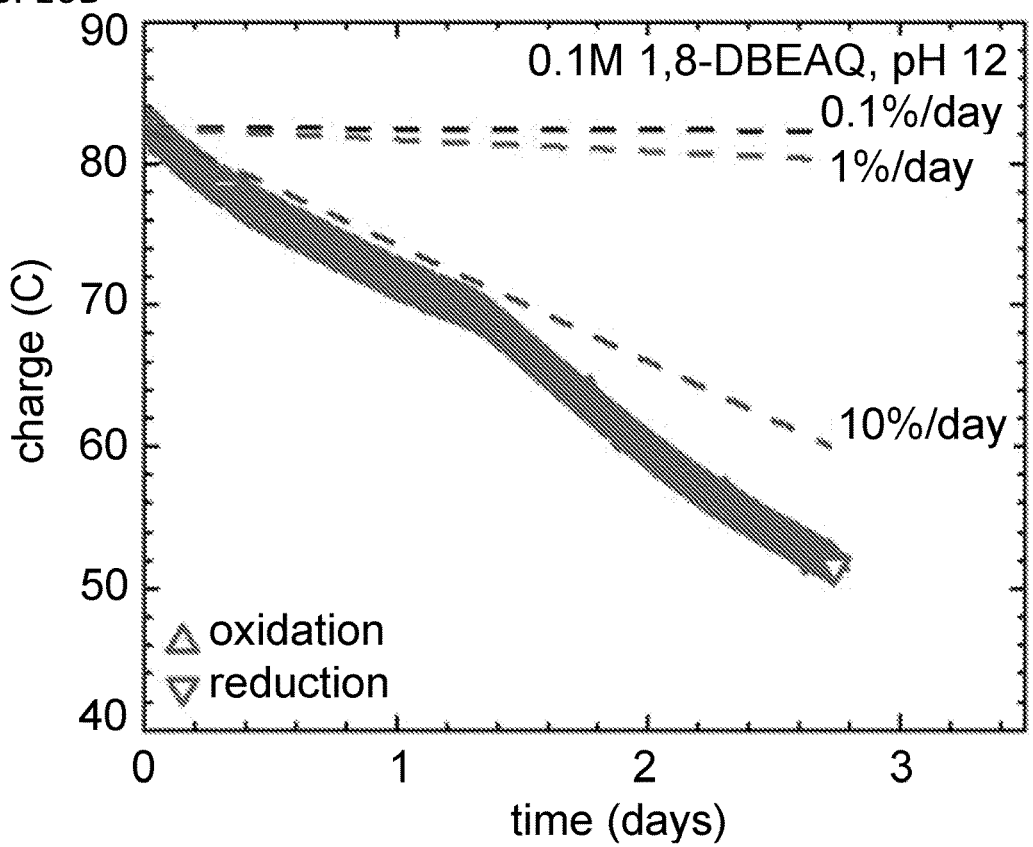

To reduce the corrosivity of the system and the ferricyanide decomposition rate, which is exacerbated at high pH[14,15], we performed the full cell tests of 2,6-DBEAQ at a more moderate electrolyte condition of pH 12. Symmetric cell cycling of 1,2-(FIG. 16A) and 1,8-DBEAQ (FIG. 16B) at pH 12 showed higher temporal fade rates—greater than 0.1 and 10%/day, respectively—than 2,6-DBEAQ at the same pH (<0.01%/day, FIG. 17) and were therefore not tested in full cell experiments. Theoretical calculations suggest that these isomers are more thermodynamically susceptible to hydroxide or water-induced γ-hydroxybutyrate cleavage than 2,6-DBEAQ (Table 2). Given the 0.6 M solubility measured for 2,6-DBEAQ at pH 12 (Table 3), subsequent cell tests were performed at 0.5 M in order to examine the performance of a full cell with reasonable energy density.

TABLE 3

Effect of solubility and full cell voltage when paired against a potassium ferrocyanide-based of posolyte on theoretical energy densities of 2,6-DHAQ and different DBEAQ isomers, with the solubility of potassium ferrocyanide estimated to be 0.5M at pH 14 and 1.25M at pH 12. Solubilities for potassium ferricyanide and 2,6-DBEAQ at pH 14 and 12 are reported in Table 1. For 2,6-DBEAQ and 2,6-DHAQ, cell voltages were obtained from the OCV at 50% SOC from full-cell tests, whereas differences in CV-obtained redox potentials between DBEAQ and potassium ferri/ferrocyanide were used for 1,2- and 1,8-DBEAQ.

| Negolyte | Solubility (M) at pH 14 (pH 12) | Cell Voltage (V) | Theoretical Energy Density (Wh/L) at pH 14 (pH 12) |
|---|---|---|---|
| 2,6-DHAQ | 0.06 | 1.20 | 11.4 |
| 2,6-DBEAQ | 1.1 (0.60) | 1.05 | 11.5 (17.2) |
| 1,2-DBEAQ | 0.9 | 1.04 | 10.9 |
| 1,8-DBEAQ | 0.75 | 1.01 | 10.2 |

Figure 19A:
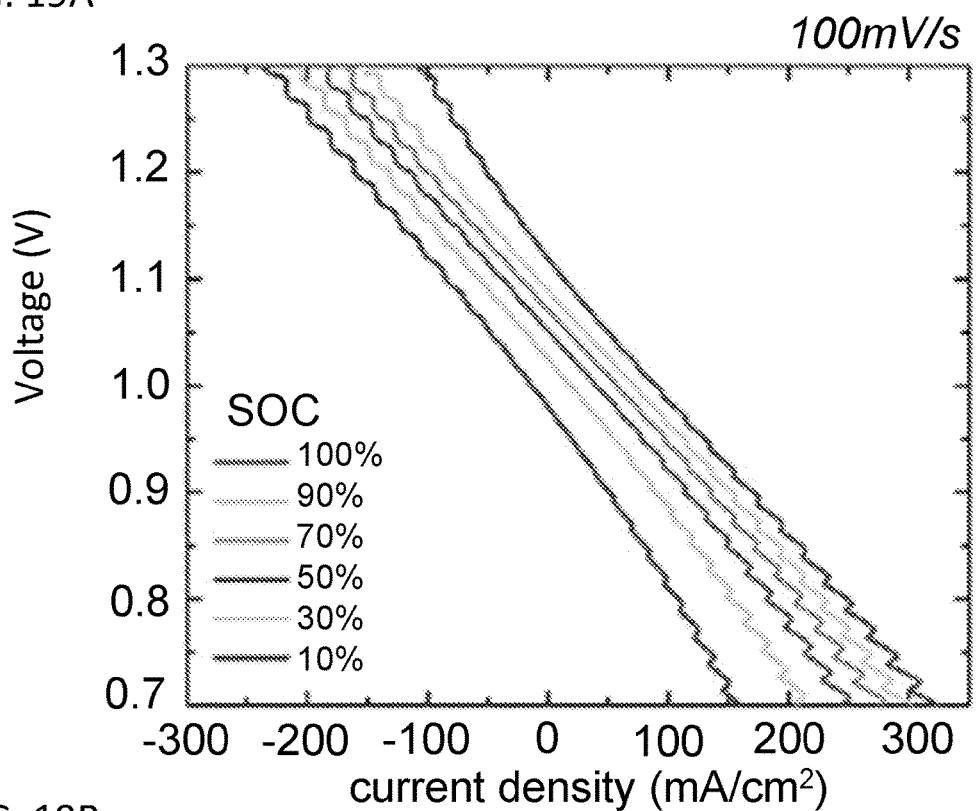
Figure 19B:
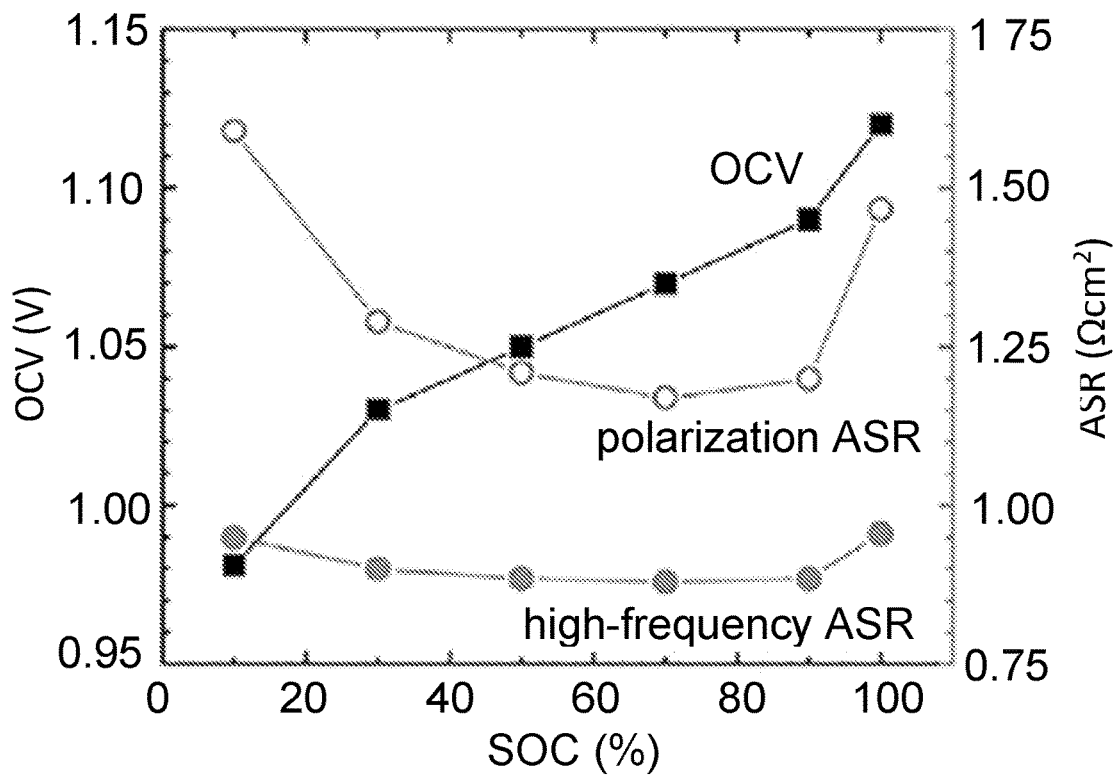
Figure 19C:
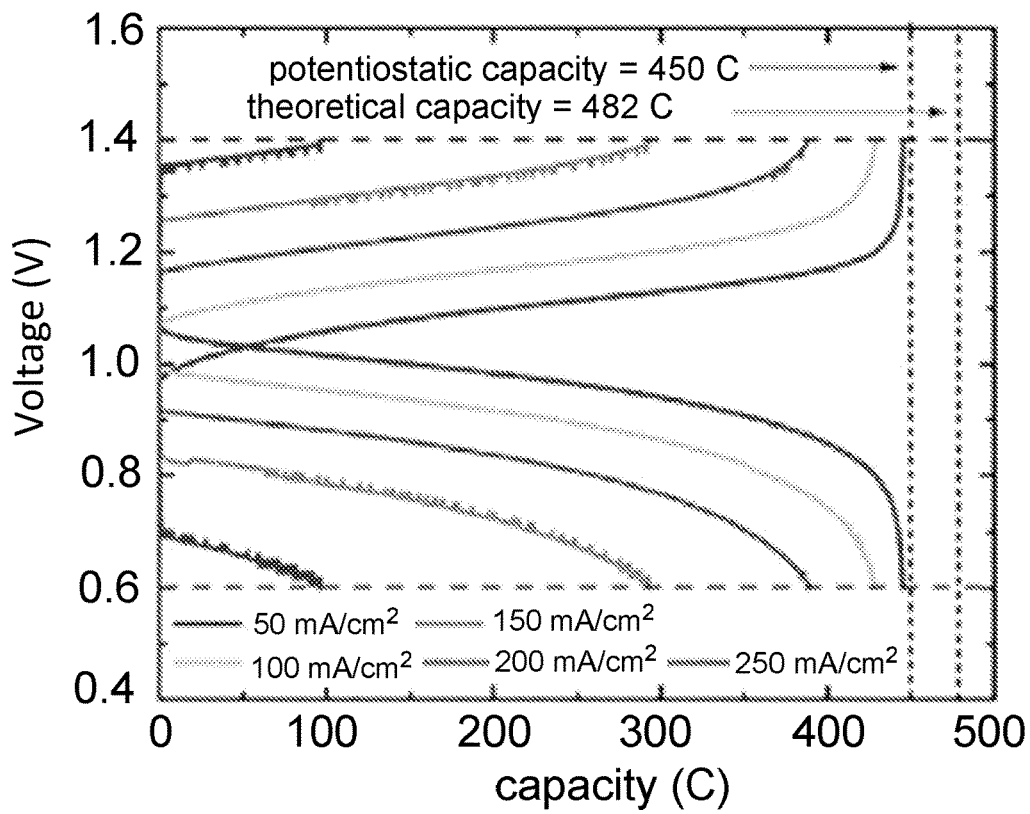
Figure 19D:
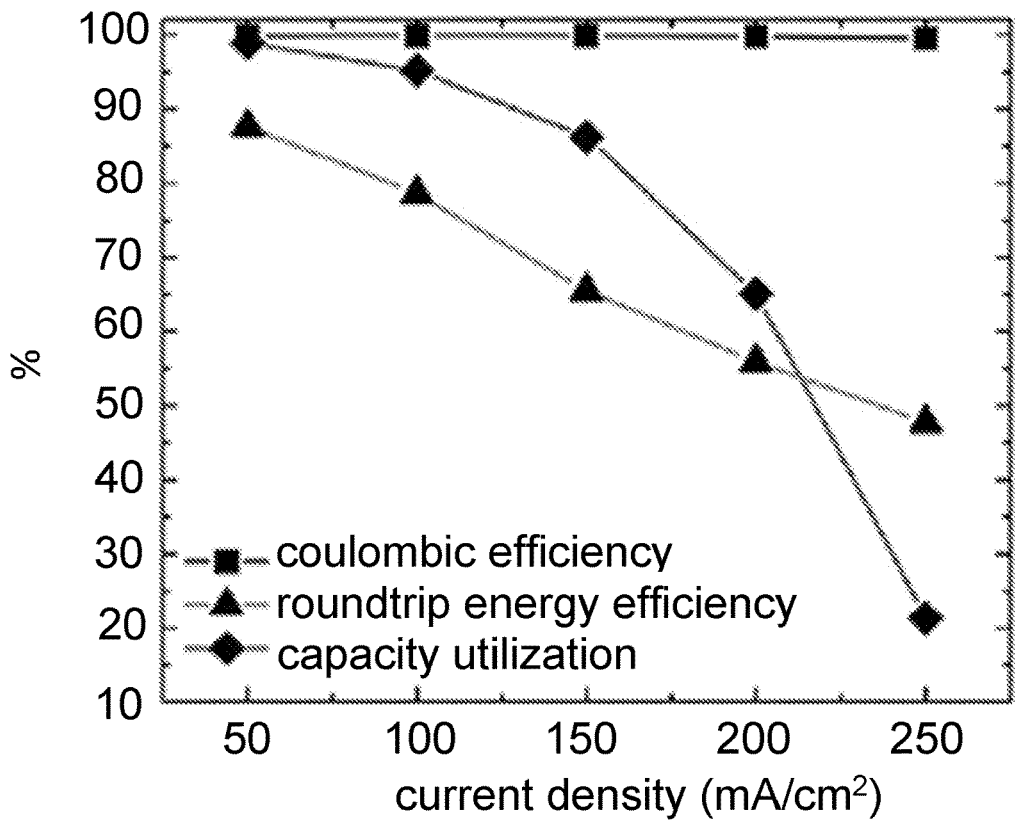

From the Pourbaix diagram of 2,6-DBEAQ (FIGS. 18A-18B), its reduction potential becomes pH independent above pH 11.5 and is not expected to change during cell cycling. Polarization and capacity utilization measurements with a negolyte containing 0.5 M 2,6-DBEAQ are shown in FIGS. 19A-19D. Polarization studies (FIG. 19A) at room temperature showed a near-linear relationship between current density and voltage at currents close to the open-circuit voltage (OCV), which increased from 0.97 V at 10% SOC to 1.12 V at 100% SOC (FIG. 19B). Between 80% and 90% of the polarization area-specific resistance (ASR) is accounted for by the high-frequency resistance measured using EIS, which largely reflects membrane resistance. A peak galvanic power density of 0.24 W/cm$^2$ was realized at 100% SOC (FIG. 20). This power density is about half of that previously reported in a 2,6-DHAQ-ferrocyanide cell[16], owing to the higher OCV of the latter (1.20 V as opposed to 1.05 V at 50% SOC) and smaller area-specific resistance (0.858 Ωcm$^2$ as opposed to 1.2 Ωcm$^2$ at 50% SOC). When voltage and current have a linear, Ohmic relationship, the peak galvanic power density is given by $p_{max}=V_{oc}^2/r$, where VOC is the open-circuit potential and r is the area-specific resistance. The low permeability of the FUMASEP® membrane to the fastest-crossing species (i.e., 200 years required for 50% loss through crossover of ferricyanide) permits, in principle, a four-fold reduction in the membrane thickness, which would raise the power density significantly.

In order to avoid temporal variations in accessible capacity during full cell cycling caused by changes in membrane resistance[8], each galvanostatic half-cycle was finished with a potential hold at the potential limit (1.4 V after charge, 0.6 V after discharge), until the magnitude of the current density fell below 2 mA/cm$^2$. Over a 5-day test period, a capacity fade rate of 0.05%/day or 0.001%/cycle was observed (FIG. 21A). A parallel cycling test was performed in which a potentiostatic charge-discharge cycle was executed after every 20 galvanostatic cycles; a capacity fade rate of 0.04%/day was observed in that case (FIG. 22B). It has been shown that capacity retention rates using both cycling protocols yield virtually identical results.[8]

These full cell measurements, however, showed roughly 4-fold increase in capacity fade compared with the <0.01%/day observed during symmetric cycling tests (FIGS. 8B-8C), suggesting additional capacity fade mechanisms not observed during symmetric-cell studies. In-depth chemical and electrochemical analysis (FIGS. 22A-22B) was performed to probe the chemical decomposition and crossover of DBEAQ from the capacity limiting side. Electrolytes in a cell compositionally identical to that in FIG. 21A but cycled for 11 days were subjected to NMR (FIG. 22A) and CV (FIG. 22B) analysis. From these results, no evidence of DBEAQ decomposition and crossover was found after examining the negolyte and posolyte before and after cycling. Based on the detection limit of NMR (0.1 mM DBEAQ) and CV techniques under the experimental conditions chosen, the upper limit of the capacity fade rate caused by 2,6-DBEAQ decomposition and/or membrane crossover was ~0.01%/day, similar to our symmetric cell study. We therefore hypothesize that other capacity fade mechanisms, such as precipitation of 2,6-DBEAQ in the posolyte after crossing over, might be operative but untraceable by NMR and CV techniques due to the slow capacity fade rate, which corresponds to a total loss of <0.5% of 2,6-DBEAQ over a 6-day testing period. One other such mechanism might be leakage of the negolyte due to poorer adhesion between the thinner FUMASEP® membrane and the Viton gasket in the full cell than between NAFION® N117 and the gasket in the symmetric cell. Indeed, the total capacity fade in FIG. 21B corresponds to a total loss over the entire 6-day cycling period of ~10 μL of negolyte volume, which is roughly one fifth of a droplet. When translated to an equivalent current density (0.5 μA/cm$^2$), this negolyte loss rate is well within expectation for seepage of the electrolyte into spaces between the gaskets and/or interface between the membrane and gaskets, as compared to an analogous leak rate estimated from a previous study of capacity fade in an anthraquinone-based flow battery with this cell architecture (0.09-0.12 mA/cm$^2$).[14]

Example 6. Permeability of Oxidized 2,6-DBEAQ Across Membranes

The permeability of the oxidized form of 2,6-DBEAQ and potassium ferricyanide across a FUMASEP® E-620(K) membrane was evaluated with a lab-made two-compartment cell. In the first case, the donating side was filled with a solution of 2,6-DBEAQ (0.1 M) in 1.6 M KOH, while the receiving side was filled with 1.6 M KOH. For potassium ferricyanide permeability, the donating side was filled with potassium ferricyanide (0.3 M) in 1 M KOH, while the receiving side was filled with 1.9 M KOH. Both compartments had the same volume. The cell was continuously agitated on a nutating table. At different time intervals, aliquots were taken from the receiving side, diluted, characterized by UV-Vis spectrophotometry, and replaced by fresh KOH solution. The electrolyte volumes on both sides were checked periodically to ensure that there was negligible water flux across the membrane, which might affect the apparent reactant permeability. The concentration was calculated from a calibration curve and the permeability of 2,6-DBEAQ was calculated based on Fick's law using the following equation:

$$P = \frac{\Delta \ln\left(1 - \frac{2c_t}{c_0}\right)\left(\frac{V_0 l}{2A}\right)}{\Delta t}$$

where P is permeability (cm$^2$/s), A is the effective membrane area (cm$^2$), t is elapsed time (s), $c_t$(mol/L) is the concentration of active species in the receiving side at time t, $V_o$ is the volume of the solution in either compartment (5 cm$^3$), l is the thickness of the membrane (~20 μm), $c_o$ is the concentration of 2,6-DBEAQ in the donating side at time zero (0.1 mol/L), and Δ represents a finite difference.

Example 7. Aqueous Flow Battery with 2,6-DBEAQ the Negative Electrolyte and Potassium Ferrocyanide as the Positive Electrolyte A flow battery was constructed using a solution of 2,6-DBEAQ produced as described in Example 1. Cell hardware from Fuel Cell Tech. (Albuquerque, N. Mex.) was used to assemble a zero-gap flow cell configuration, similar to a previous report (supplemental information in the paper by K. Lin et al. Science 349, 1529 (2015)). Pyrosealed POCO graphite flow plates with serpentine flow patterns were used for both electrodes. Each electrode had a 5 cm² geometric surface area covered by a stack of three sheets of Sigracet SGL 39AA porous carbon paper pre-baked in air for 8 h at 400° C. A sheet of pretreated NAFION® 212 membrane served as the ion-selective membrane between the carbon electrodes. Pretreatment of the NAFION® 212 membrane was performed by first heating it at 80° C. in de-ionized water for 20 minutes and then soaking in 5% hydrogen peroxide solution at room temperature for 35 minutes. These pre-treated membranes were stored in 0.1 M KOH solution at room temperature. The outer portion of the space between the electrodes was gasketed by Teflon sheets with the area over the electrodes cut out. Torque applied during cell assembly was 90 lb-in on each of 8 bolts. The electrolytes were fed into the cell through PFA tubing, at a rate <60 ml/min controlled by Cole-Parmer Micropump gear pumps. The cell was run inside a nitrogen-filled glove box with an $O_2$ partial pressure of about 1 to 2 ppm. Cell polarization measurements, impedance spectroscopy, and charge-discharge cycling were performed using a Biologic VSP 300 potentiostat. The posolyte volume and composition when assembled was 30 mL of 0.22 M potassium ferrocyanide, 0.02 M potassium ferricyanide and 1 M KOH. The capacity-limiting negolyte was prepared by dissolving 1.2 mmoles of 2,6-DBEAQ (0.5 g) in its oxidized form in 1.2 M KOH solution (6 mL) resulting a 0.2 molar 2,6-DBEAQ solution.

For a full cell study, the electrolytes were assembled in the fully discharged state, deaerated and brought into a nitrogen-filled glovebox. The oxygen level was maintained at <2 ppm during cycling. Galvanostatic cycling was performed at ±0.1 A/cm² at room temperature, with voltage limits of 0.6 and 1.4 V, controlled by a Gamry 30K Booster potentiostat.

The open-circuit voltage was 1.02 V at 50% state of charge with respect to the negolyte. Our experiments have shown that the loss of capacity of a cell based on a 2,6-DBEAQ negative electrolyte was lower than that of a comparable cell based on a 2,6-dihydroxyanthraquinone negative electrolyte.

Example 8. Redox Chemistry of 2,6-DBEAQ Vs. 2,6-DHAQ

Following our previous study on 2,6-DHAQ[17] and literature reports[1,18] on quinone electrochemistry in the absence of proton donors, we simulated the CV of 2,6-DBEAQ as representing two reversible electron transfer steps at two different potentials $E_1$ and $E_2$. The separation between simulated redox potentials for the first ($E_1$) and second ($E_2$) electron reductions for 2,6-DBEAQ is considerably narrower than the corresponding peak separation for 2,6-DHAQ[17] (6 mV vs. 60 mV). An important implication of this difference is that there is a smaller driving force for the formation of semiquinone radicals between fully oxidized and fully reduced 2,6-DBEAQ species than there is for 2,6-DHAQ. In order to demonstrate why this is the case, we first explain the effect of $E_1$-$E_2$ separation on the reduction mechanism and then draw a connection between the reduction potential difference and the semiquinone concentration.

The pH dependence of the proton-coupled electron transfer (POET) redox reaction for a generalized anthraquinone (AQ) is often visualized by the nine-membered square scheme (FIG. 7). The horizontal direction indicates electron transfer (ET), and the vertical direction indicates proton transfer (PT or protonation). Under strongly alkaline conditions, where the pH is higher than the second $pK_a$ ($pK_{a2}$) of the reduced AQ ($AQ^{2-}$), no protonation of the semiquinone anion will take place, and reduction proceeds via two ET steps, from AQ to a semiquinone (AQ-•) at $E_1$, and from AQ-• to $AQ^{2-}$ at $E_2$ which is typically <$E_1$. Depending on the value of $E_1$-$E_2$, the mechanism of AQ reduction in alkaline conditions can either be a concerted one-step, two-electron process or two single-electron processes. When $E_2$ becomes more negative relative to $E_1$, a stepwise process via a semiquinone radical is followed, as in AQ reduction in aprotic solvents.[1,19] Under these conditions, a comproportionation reaction, where AQ and $AQ^{2-}$ combine to generate AQ-• semiquinone (Equation 3) is thermodynamically favorable. The equilibrium constant for this comproportionation ($K_{eq\_comp}$) can be obtained by dividing the equilibrium constants of $E_1$ (Equation 4) by that of $E_2$ (Equation 5), which now becomes Equation 6.[18] The ratio between semiquinone concentration and the geometric mean of the concentrations of the oxidized and reduced forms of AQ can now be seen as an increasing function of $E_1$-$E_2$.

$$AQ + e^- \rightleftharpoons AQ^- \quad \text{(Eq. 1)}$$

$$AQ^- + e^- \rightleftharpoons AQ^{2-} \quad \text{(Eq. 2)}$$

$$AQ + AQ^{2-} \rightleftharpoons 2AQ^- \quad \text{(Eq. 3)}$$

$$E_1 = \frac{RT}{ZF}\ln K_{eq1};\ K_{eq1} = \frac{[AQ^-]}{[AQ]} = \exp\left(\frac{zF}{RT}E_1\right) \quad \text{(Eq. 4)}$$

$$E_2 = \frac{RT}{ZF}\ln K_{eq2};\ K_{eq2} = \frac{[AQ^{2-}]}{[AQ^-]} = \exp\left(\frac{zF}{RT}E_2\right) \quad \text{(Eq. 5)}$$

$$K_{eq\_comp} = \frac{K_{eq1}}{K_{eq2}} = \frac{[AQ^-]^2}{[AQ]\cdot[AQ^{2-}]} = \exp\left[\frac{zF}{RT}(E_1 - E_2)\right] \quad \text{(Eq. 6)}$$

This equation directly relates the concentration of semiquinone species to the $E_1$-$E_2$ separation and suggests that $K_{eq\_comp}$ for semiquinone formation is 2.83 times higher for 2,6-DHAQ than it is for 2,6-DBEAQ for the same AQ:$AQ^{2-}$ ratio, based on their respective $E_1$-$E_2$ separations.

The differences in energy between the first and second reduction can also be estimated with electronic structure calculations. Conformers of the oxidized, one-electron reduced, and two-electron reduced forms of 2,6-DHAQ and 2,6-DBEAQ were generated with the UFF force field using RDKit.[6] The redox active sites of the one-electron and two-electron reduced forms were paired with one and two potassium cations, respectively. The deprotonated carboxyl and hydroxyl groups were also paired with potassium cations. This pairing is done to approximate the ion pairing behavior of the molecules in solution in lieu of an explicit solvent, as has been done previously.[20] The relative energies of the first and second reduction were calculated with both semiempirical methods (PM7 COSMO) and density functional theory (DFT) methods in a polarizable continuum model (PCM) implicit solvent (B3LYP/6-311+G(d,p)). The DFT single point energies were evaluated at the B3LYP/6-

31G(d) (no PCM) minima. Typically, when calculating reduction potentials, a calibration scheme is employed,[19] or the relative energetics of all molecules are computed relative to a fixed molecule where the experimental result is known[19]; the latter strategy is used in this case with 2-6 DHAQ used as the internal standard. We find that using DFT is necessary to qualitatively predict these differences (though the shift is overestimated) in the first and second reduction. This suggests that such a behavior can be screened for in future studies, at least for quantitative estimation of semiquinone presence.

TABLE 4

Estimated difference in potential between the first and the second reduction for 2,6-DHAQ and 2,6-DBEAQ.

| Negolyte | B3LYP/6-311+G(d,p) PCM Estimated $E_1$-$E_2$ (V) |
|---|---|
| 2,6-DHAQ* | 0.060 |
| 2,6-DBEAQ | −0.133 |

*Note that the energy differences are calibrated so that the differences for 2,6-DHAQ are fixed to experiment.

Example 9. Decomposition of 2,6-DBEAQ

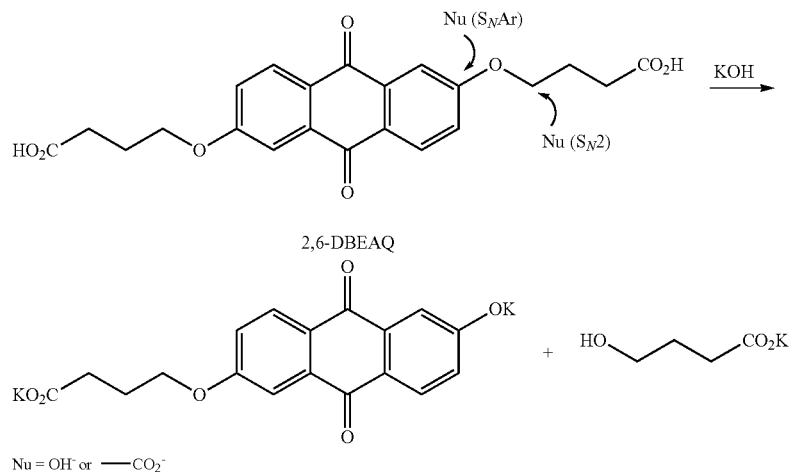

Scheme 5. Proposed decomposition mechanisms for 2,6-DBEAQ

Nu = OH⁻ or —$CO_2^-$

Chemical stability studies at elevated temperature indicate that the oxidized form of 2,6-DBEAQ is susceptible to decomposition by γ-hydroxybutyrate cleavage (Scheme 5), as confirmed by $^1$H NMR.[21] Notably, cleavage of a second γ-hydroxybutyrate moiety leads to 2,6-dihydroxyanthraquinone (2,6-DHAQ), whose capacity fade rate, has been reported to be 5%/day.[21,22] The rate of 2,6-DBEAQ decomposition has been shown to be considerably slower at pH 12 relative to pH 14 at 95° C. and 0.1 M concentration (FIGS. 23E, 23F, and 24A-24D).[21] Noting the influence of pH on the degradation rate and that both hydroxide and carboxylate may act as nucleophiles in the decomposition (Scheme 5), we therefore expect further enhancement in stability with lower pH operating conditions and with suppression of the carboxylate-mediated intramolecular nucleophilic substitution reaction. We designed an analogue of 2,6-DBEAQ but with phosphonate-terminated functional groups, DPPEAQ, appearing to deliver both of these desired outcomes.

Example 10. Synthesis of DPPEAQ

Scheme 6.
Synthesis of (((9,10-dioxo-9,10-dihydroanthracene-2,6-diyl)bis(oxy))bis (propane-3,1-diyl))bis(phosphonic acid), abbreviated as 2,6-DPPEAQ

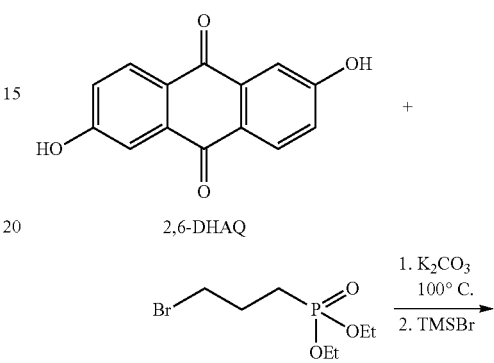

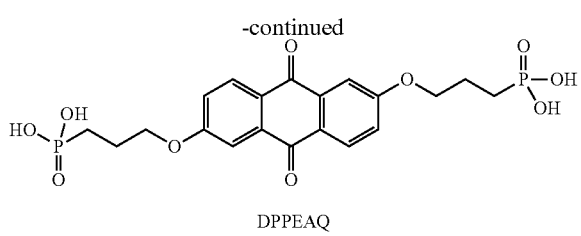

DPPEAQ 2,6-dihydroxyanthraquinone (2,6-DHAQ) was purchased from AK Scientific. All other chemicals were purchased from Sigma Aldrich. All chemicals were used as received unless specified otherwise.

2,6-DHAQ (10 mmol) was mixed with anhydrous $K_2CO_3$ (40 mmol) and diethyl (3-bromopropyl)phosphonate (30 mmol) in DMF (50 mL). The reaction mixture was then heated to 100° C. overnight. After removing the solvent, the solid was washed thoroughly with DI water. The product was analyzed by $^1$H NMR and used for the next reaction step without further purification. The ester precursor of DPPEAQ was dissolved in dichloromethane (100 mL), and trimethylsilyl bromide (TMSBr) (100.0 mmol) was added. After 15 h stirring at room temperature, the solvent and excess TMSBr were distilled off. The mixture was washed thoroughly with DI water and hexane, then vacuum dried to yield yellow solid. Final yield: 98%.

DPPEAQ was synthesized by the route illustrated in Scheme 6, which presents several advantages that make it particularly suitable for grid storage. The simple synthesis uses only two steps, an O-alkylation reaction and hydrolysis of the ester, to introduce the highly soluble phosphonic acid terminal groups. Both synthesis steps achieved >98% yield, facilitating scale-up without the need for more resource-intensive purification such as chromatography and thus presenting a feasible pathway for large scale industrial manufacturing.

The $^1$H NMR spectrum of (((9,10-dioxo-9,10-dihydroanthracene-2,6-diyl)bis(oxy))bis(propane-3,1-diyl))bis(phosphonic acid) (DPPEAQ) is shown in FIG. 25.

Example 11. Permeability and Solubility Tests of DPPEAQ

Permeability Measurements

The permeability of the electroactive molecules was measured in a lab-made two compartment diffusion cell. A 0.1 M solution of DPPEAQ in KOH at pH 9 and pH 14 was placed on the donating side and paired with 0.2 M KCl at pH 9 and pH 14 solution on the receiving side, to balance both the potassium concentration and the ionic strength between sides. To keep the solutions under agitation, the cell was placed on a nutating table. The increase of DPPEAQ concentration in the receiving side was measured as a function of time with UV-visible absorption spectrophotometry (Ocean Optics Flame-S Spectrometer Assembly). For each time point, a 400 μL aliquot of the solution on the receiving was taken, diluted, measured by UV-Visible and replaced by fresh 0.2 M KCl solution.

Due to a very low crossover and to the detection limit of the spectrometer we were only able to estimate a maximum value of DPPEAQ permeability. According to the derivation of Fick's Law as reported in our previous paper[21], DPPEAQ permeability must be lower than $3.4 \times 10^{-13}$ $cm^2/s$. Ferricyanide permeability has been measured and published previously for this membrane and it is equal to $4.4 \times 10^{-12}$ $cm^2/s$.[21]

Solubility Tests

The solubility limit of DPPEAQ was measured in the oxidized form by adding the potassium salt of DPPEAQ (prepared by reacting DPPEAQ with potassium hydroxide in water) until no further solid could be dissolved. The mixture was adjusted to pH 9. After filtering the mixture through a PTFE 0.45 μm syringe filter, a saturated solution of DPPEAQ at pH 9 was obtained. The saturated solution was then diluted by a known amount while maintaining a pH of 9, and the concentration was evaluated by UV-Vis (Agilent Cary 60 spectrophotometer). The concentration was calculated according to a pre-calibrated absorbance-concentration curve of known concentrations of DPPEAQ at pH 9. The resulting value of the solubility of the oxidized form of DPPEAQ at pH 9 is 0.75 M.

The solubility of the oxygen-sensitive reduced form of DPPEAQ was not measured but was assumed to be higher than the oxidized form because: (1) no precipitation after full electrochemical reduction of DPPEAQ was observed, and (2) the increased negative charges of DPPEAQ in the reduced form compared to DPPEAQ in the oxidized form is expected to render quinone-quinone interactions even more unfavorable and increase its solubility.

Whereas the solubility of 2,6-DBEAQ at pH 9 (<35 mM) is impractically low for use in a cell, the phosphonate functional group affords DPPEAQ a much higher solubility at pH 9 (0.75 M) to enable the operation of DPPEAQ under milder conditions. When similar elevated temperature chemical studies were performed for DPPEAQ at pH 9 as well as at pH 12, no significant decomposition was observed in either case (FIGS. 23A-23D). 2,6-DBEAQ and DPPEAQ do, however, exhibit a similar extent of decomposition at pH 14 (FIGS. 24A-24D). The differing relative stabilities of DPPEAQ and 2,6-DBEAQ at pH 12 (at 95° C. and 0.1 M concentration), in contrast to the similar extent of their observed decomposition at pH 14, may be due to a competition between multiple decomposition mechanisms that vary in a pH-dependent manner. The concentration of hydroxide ions at pH 14 is tenfold higher than the concentration of either molecule at 0.1 M, as opposed to tenfold lower at pH 12. In particular, we propose a hydroxide-mediated nucleophilic substitution reaction ($S_NAr$ or $S_N2$) that dominates the decomposition of both molecules at pH 14. However, at a lower pH of 12, an intramolecular reaction with carboxylate acting as the nucleophile dominates in the decomposition of 2,6-DBEAQ, while no analogous intramolecular reaction of DPPEAQ at pH 12 can take place due to much weaker nucleophilicity of bulked phosphonate compared with carboxylate. The difference in the dominant mechanisms of 2,6-DBEAQ decomposition at pH 12 and 14 that we are proposing is also consistent with the observation that the initial rate of degradation is not 100-fold slower at pH 12 relative to pH 14. Unlike the oxidized form of DPPEAQ, its reduced form, obtained by electrochemical reduction, exhibits robust chemical stability even at pH 14 (FIGS. 26A-26C). Collectively, these results suggest the high stability of DPPEAQ between pH 9 and 12. In addition, the operability at lower pH serves to decrease the corrosion of battery systems and enable the use of less expensive materials.

Example 12. Cyclic Voltammetry (CV) and Rotating Disk Electrode (RDE) Measurements of DPPEAQ Glassy carbon was used as the working electrode for all three-electrode CV tests. RDE experiments were conducted using a Pine Instruments Modulated Speed Rotator AFMSRCE equipped with a 5 mm diameter glassy carbon working electrode, a Ag/AgCl reference electrode (BASi, pre-soaked in a 3 M KCl solution), and a graphite counter electrode. The diffusion coefficient of the oxidized form of DPPEAQ was calculated using the Levich equation, which relates the mass-transport-limited current to the number of electrons transferred (n), the area of the electrode (A), and the concentration of redox-active species in the electrolyte (C), by plotting the mass-transport-limited current against the square root of the rotation rate (FIGS. 27A-27B) with the following parameters: n=2, F=96,485 Coulombs/mol, A=0.196 $cm^2$, C=5 mM, kinematic viscosity of 1 M KOH v=$1.08 \times 10^{-6}$ $m^2/s$. The resulting value of the diffusion coefficient for the oxidized form of DPPEAQ is $1.37 \times 10^{-6}$ $cm^2/s$.

Figure 28A:
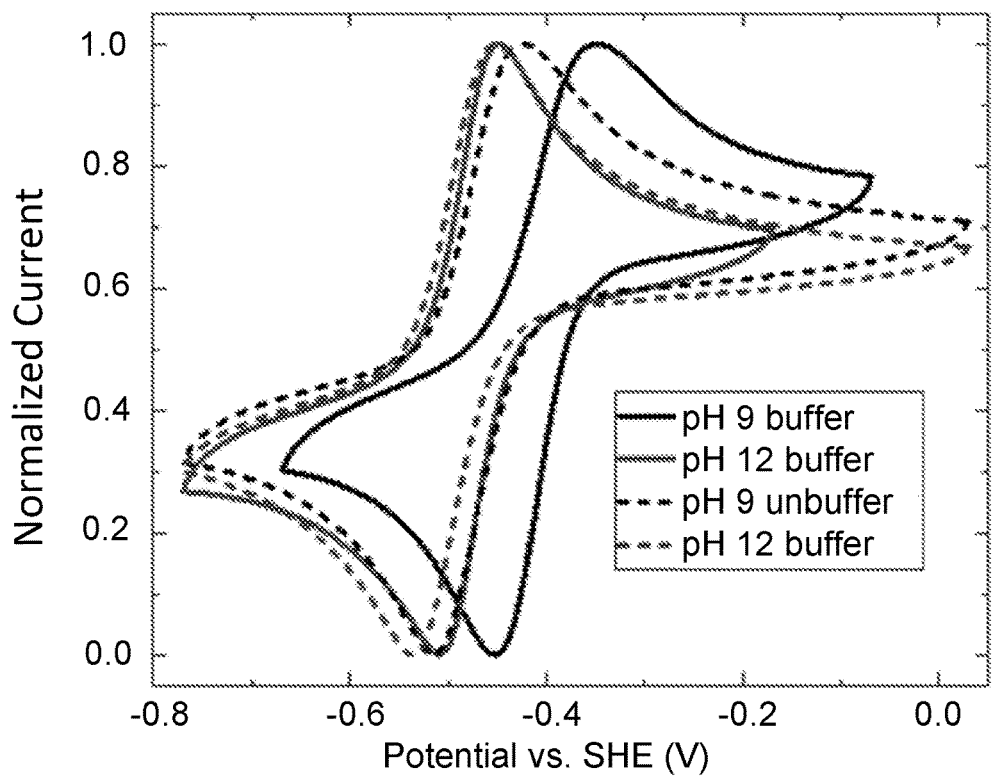

Based on cyclic voltammetry (CV), DPPEAQ exhibits a reversible redox peak at −0.47 V vs. SHE ($E_{1/2}$) in pH 9 unbuffered aqueous solution and at −0.49 V vs. SHE ($E_{1/2}$)

in pH 12 unbuffered aqueous solution (FIG. 28A). In contrast, in buffered pH 9 and pH 12 solutions, DPPEAQ shows redox potentials of −0.39 vs. SHE ($E_{1/2}$) and −0.47 V vs. SHE ($E_{1/2}$) respectively (FIG. 29), conforming to the pH-dependent CV behavior of quinones.[1] During the cell cycling process, the proton-coupled redox reactions of quinones in water can alter the pH, as the reduction of quinones in aqueous solution consumes protons, thereby increasing pH, whereas oxidation of hydroquinones in aqueous solution releases protons, thereby decreasing pH. These pH fluctuations should be reversible during cell cycling.

Example 13. Cycling Stability Measurements of DPPEAQ

Figure 28B:
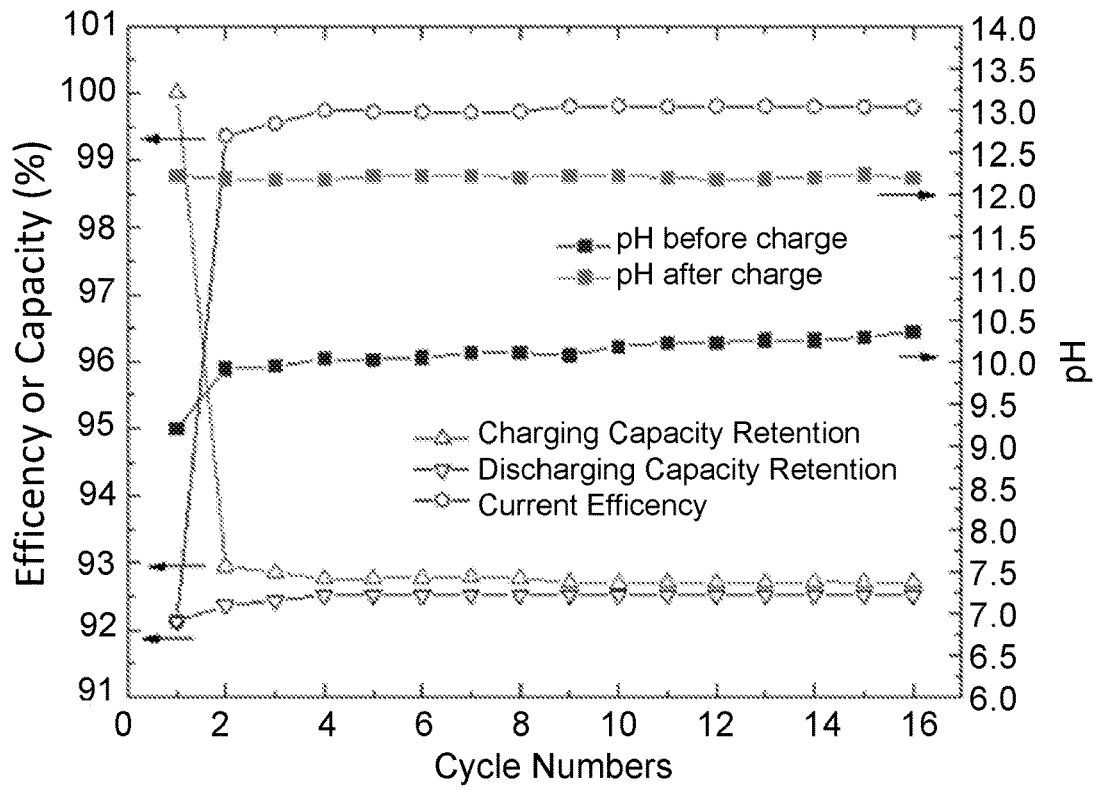
Figure 28C:
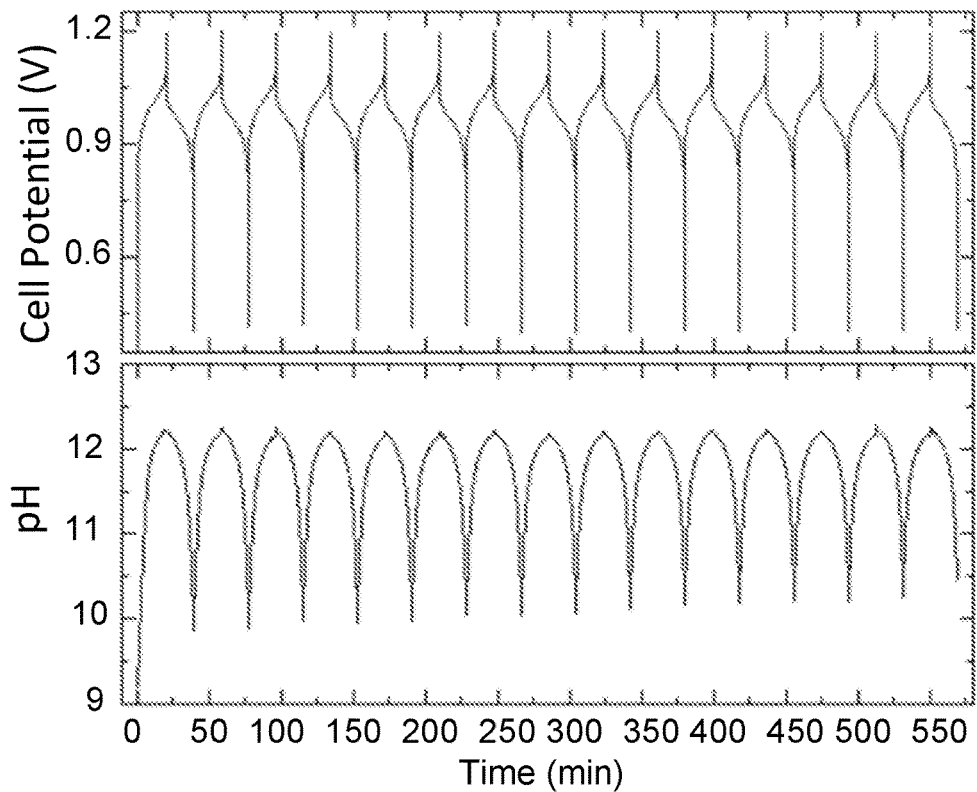
Figure 28D:
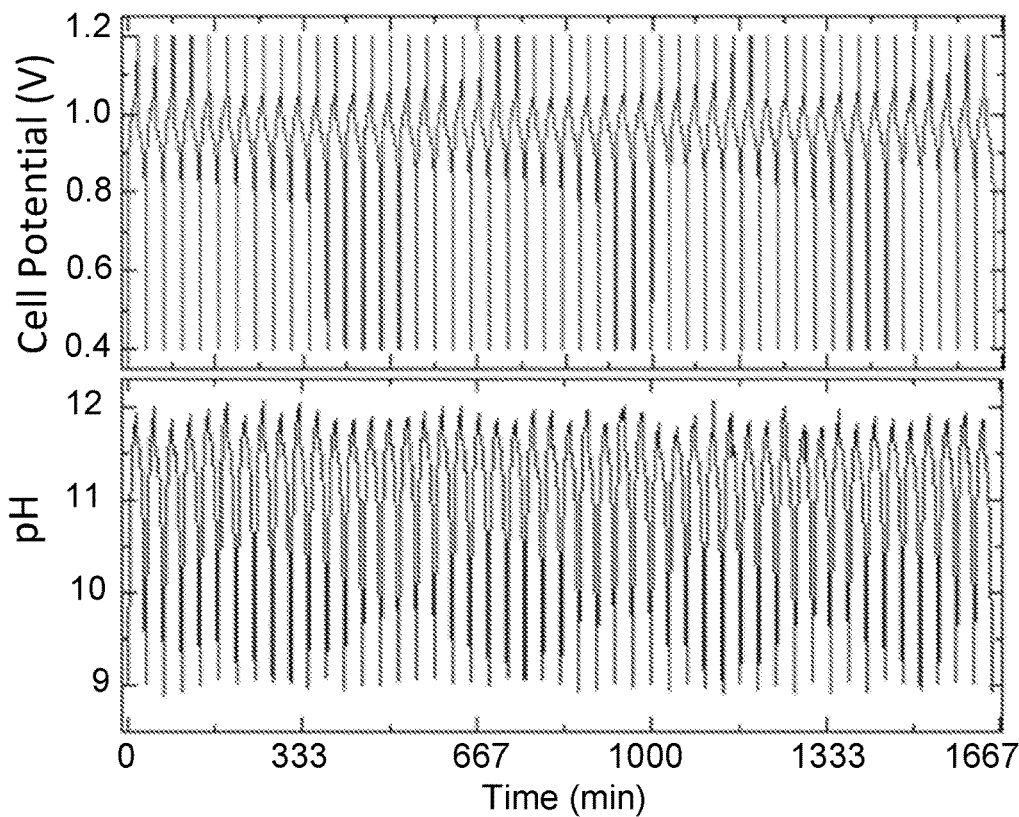

To prove the pH reversibility and cycling stability, a cell was assembled with a negolyte including 0.1 M DPPEAQ in 1 M KCl, the pH of which was monitored by a pH probe immersed in the solution, and a posolyte comprising 0.1 M $K_4Fe(CN)_6$ and 0.01 M $K_4Fe(CN)_6$ in 1 M KCl, separated by a FUMASEP® E-620(K) membrane (FIGS. 28B-28C). The pH of both sides was adjusted to 9 by adding a trace of KOH.

Operating at pH 9 enhances the stability of the posolyte as well as the negolyte, as the decomposition rate of ferricyanide, which is typically used as a posolyte in neutral and alkaline batteries, is increased at high pH.[15,23] The cell was cycled at a constant current density of ±20 mA/cm² for 16 cycles using voltage cut-offs of 0.4 V and 1.2 V. During the first charge cycle, the negolyte pH increased from 9.2 to 12.2. After the first discharge cycle, the pH decreased to 9.9 instead of 9.2. We attribute the increase in pH in the discharged state to the consumption of atmospheric oxygen dissolved in the solution and reservoir. When hydroquinones are oxidized electrochemically during cell discharge, the increase in pH that occurred during charging is reversible. If, however, hydroquinones, in any protonation state, are instead oxidized by molecular oxygen, then an irreversible increase in pH occurs. In this case, the quinone serves as a mediator for the oxygen reduction reaction (ORR), which has the effect of increasing the pH. After the first cycle, the current efficiency exceeded 99%, and both the potential and pH cycles exhibited high reproducibility. The negolyte pH fluctuated reversibly between approximately 10 and 12 during the charge and discharge process. The discharge capacity did not fade after 16 cycles (9.5 hours), indicating that the battery was capable of operating with minimal capacity fade, consistent with the demonstrated high chemical stability. The negolyte pH in the charged state remained at approximately pH 12.2, suggesting that the redox reaction becomes pH independent at pH values higher than 12.2. In contrast, the negolyte pH in the discharged state continued to slowly increase to 10.4 after 16 cycles (9.5 hours), which we attribute to oxygen penetration. We anticipate that with oxygen penetration, the negolyte pH in the discharged state will continue to gradually increase and may eventually exceed 12.2 in both the charged and discharged states after long-term cycling. The posolyte pH remained stable, as the redox reactions of ferri-ferrocyanide do not involve protons. To exclude oxygen penetration causing pH increasing, another cell was cycled in the glove box instead of glove bag. As shown in the FIG. 28D, both the potential and pH cycles were quite reproducible. The pH in the discharged state stayed around pH 9 as the beginning and the pH in the charged state stayed around pH 12, suggesting the feasibility of cell cycling between pH 9 and 12 when oxygen was eliminated.

The cycling stability of the DPPEAQ electrolyte was also studied by a previously published symmetric cell method.[24] Although the oxidized form of DPPEAQ is readily soluble at pH 9, proton-coupled electron transfer raises the pH of the electrolyte when it is reduced. Such pH fluctuations can produce misleading results in symmetric cell testing unless the starting pH is above the cutoff point for proton-coupled electron transfer. The experiment shown in FIG. 30A demonstrates the capacity fade behavior of a symmetric cell at pH 13, using +−200 mV to access >99% of the theoretical capacity of the 4.5 mL of 0.1 M limiting electrolyte, the cell was cycled for 6 days at pH 13, averaging 0.02%/day of capacity fade (FIG. 28A).

Example 14. Full Cell Measurements of DPPEAQ in an Aqueous Flow Battery

Figure 30A:
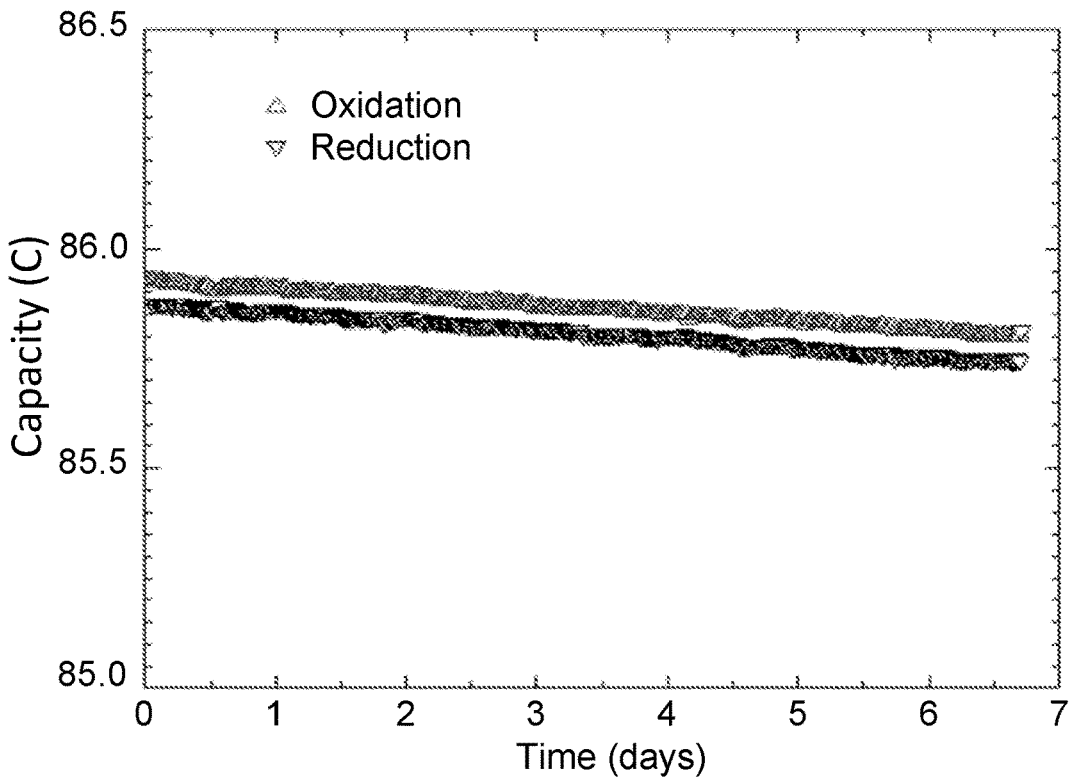
Figure 30B:
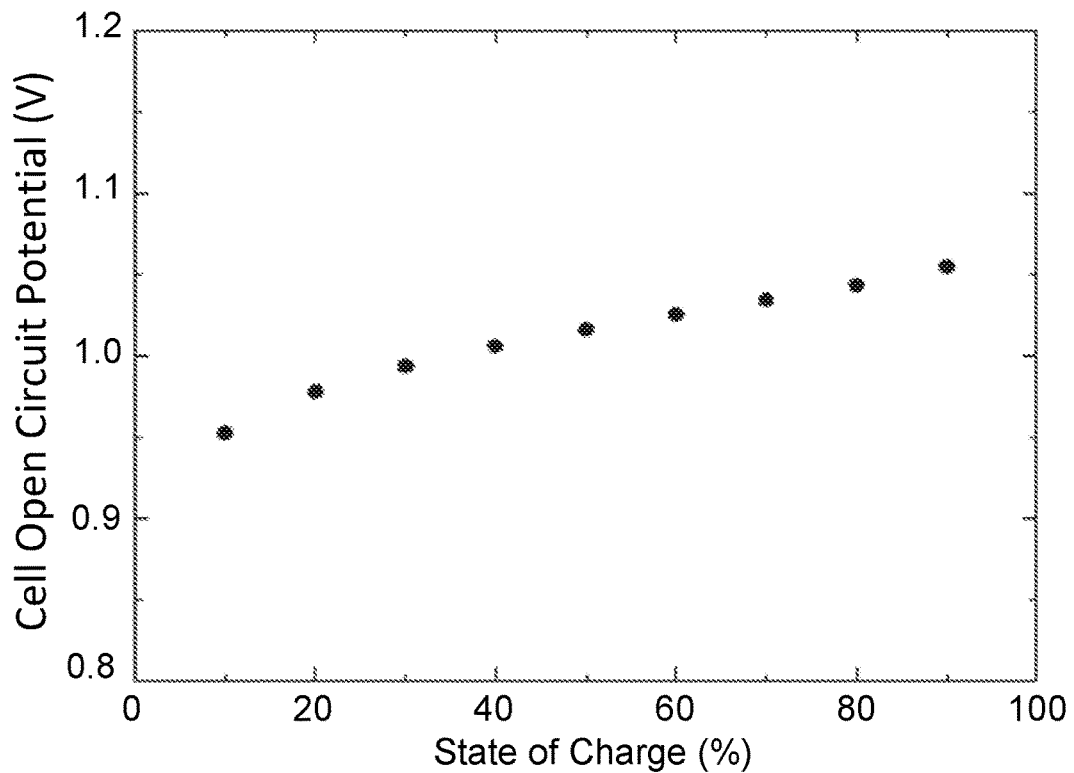
Figure 30C:
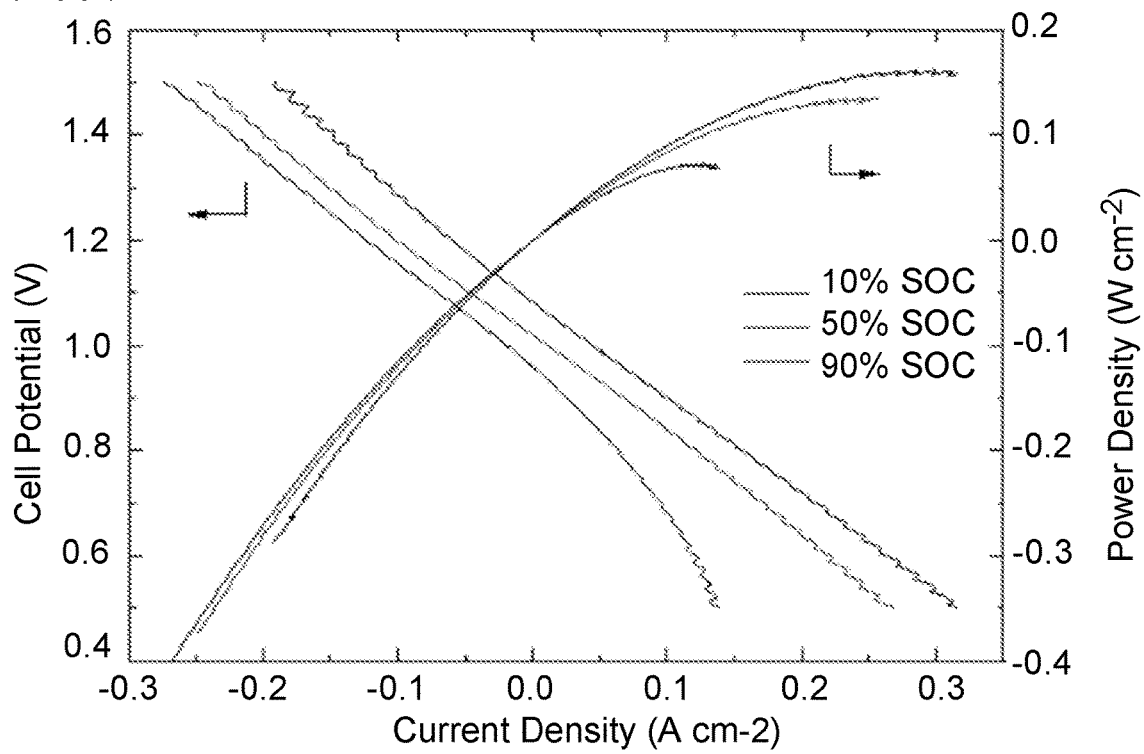

High concentration and long-term full cell testing was performed at 20° C. with solutions of 0.5 M DPPEAQ in the negolyte and 0.4 M $K_4Fe(CN)_6$, 0.1 M $K_3Fe(CN)_6$ in the posolyte, both dissolved in aqueous solution with pH adjusted to approximately 9 by the addition of traces of KOH. The high solubility and high charge of DPPEAQ enable the use of less supporting electrolyte without compromising the ionic conductivity of the solution. These solutions were pumped through a flow cell constructed from graphite flow plates and carbon paper electrodes, separated by a FUMASEP® E-620 (K) membrane, which has a high conductivity and low permeability to DPPEAQ and ferricyanide as reported in the supporting information. The RFB was charged stepwise at constant voltage (1.5 V) with a 10% increment in the state of charge (SOC) at room temperature; polarization curves were measured at 10%, 50%, and 90% states of quinone charge (SOC). The OCV at 50% SOC is approximately 1.02 V. As the SOC increased from 10% to 90%, the open-circuit potential increased from 0.95 V to 1.05 V (FIG. 30B). In the galvanic direction, peak power densities were 0.073 W $cm^{-2}$ and 0.160 W $cm^{-2}$ at these same SOCs, respectively (FIG. 30C). The area-specific resistance (ASR) of the membrane (~1.3 Ωcm², determined by high-frequency electrochemical impedance spectroscopy (EIS) in the full cell) was responsible for approximately 80% of the ASR of the entire cell (~1.6 Ωcm², DC polarization). It is anticipated that a membrane with lower resistivity will raise the power density significantly.

Figure 30D:
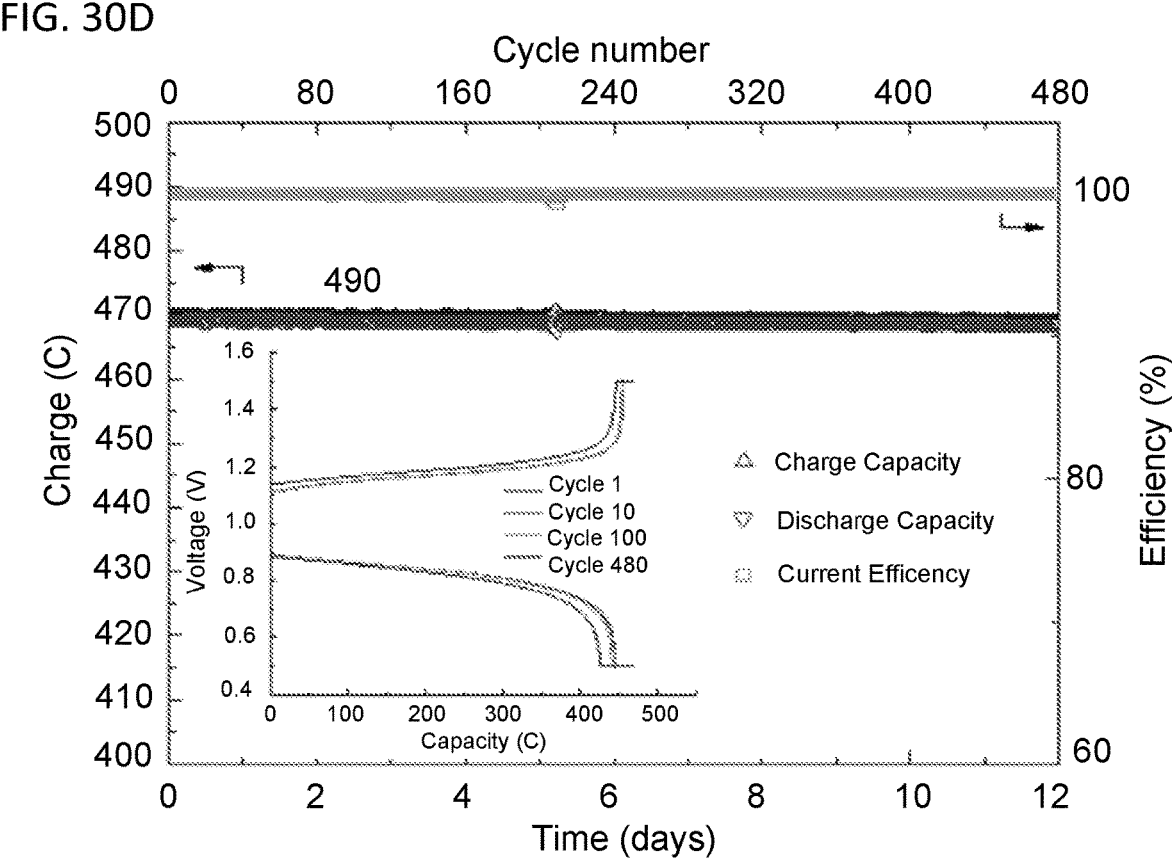

The cell was cycled at a constant current density of ±0.1 A cm⁻², and each galvanostatic half-cycle was finished with a potential hold at the potential limit (1.5 V after charge, 0.5 V after discharge) until the magnitude of the current density fell below 2 mA/cm² to avoid temporal variations in accessible capacity during full cell cycling caused by changes in membrane resistance. The cell was cycled for 480 cycles, which required 12.3 days to complete at 100 mA cm⁻². The average capacity retention over the 480 cycles was 99.99964%/cycle at an average Coulombic efficiency greater than 99%, which reflects a capacity fade rate of 0.00036%/cycle or 0.014%/day (FIG. 30D). This temporal fade rate is lower than any other RFB chemistry that has been published to date, including a viologen-based flow battery with a capacity fade rate of 0.0011%/cycle or 0.033%/day in full cell testing.[25] After 12.3 days of cycling, the pH of the discharged negolyte was measured to have increased to nearly 13 as we predicted. Although the cell was run in a glove bag with nitrogen flowing, some oxygen was inadvertently introduced during the initial set-up. As mentioned previously, this influx of oxygen would have caused homogeneous oxidation of the charged negolyte and an associated permanent increase in the pH of the negolyte. The same experiment was also done in the glove box, showing the reversible pH fluctuations during quinone cell cycling when oxygen was eliminated (FIG. 31).

In conclusion, by functionalizing an anthraquinone with phosphonate groups, we demonstrate a nearly neutral RFB negolyte with high solubility and high stability. A full cell at 0.5 M concentration, exhibited an OCV of 1V, high performance and a low capacity fade rate (0.00036%/cycle, 0.014%/day). This is the highest reported capacity retention rate of any aqueous organic RFB chemistry, approaching the requirements for grid storage applications. We also study and demonstrate the reversible pH fluctuations during quinone cell cycling. This work demonstrates the knowledge and experience gained from studying the stability of organic molecules in both oxidized and reduced redox states can be used to develop new stable molecule structures to achieve aqueous organic flow battery with long lifetime.

REFERENCES

1. M. Quan, D. Sanchez, M. F. Wasylkiw, and D. K. Smith, "Voltammetry of Quinones in Unbuffered Aqueous Solution: Reassessing the Roles of Proton Transfer and Hydrogen Bonding in the Aqueous Electrochemistry of Quinones", Journal of American Chemical Society 129, 12847 (2007). 2. D. Karandur, K. Y. Wong, and B. M. Pettitt, "Solubility and Aggregation of Gly(5) in Water", *J Phys. Chem. B* 118, 9565 (2014).
3. K. Lin, Q. Chen, M. R. Gerhardt, L. Tong, S. B. Kim, L. Eisenach, A. W. Valle, D. Hardee, R. G. Gordon, M. J. Aziz, and M. P. Marshak, "Alkaline Quinone Flow Battery", *Science* 349,1529 (2015).
4. A. J. Esswein, J. Goeltz, and D. Amadeo, "High Solubility Iron Hexacyanides", Patent US 2014/0051003 A1 (Feb. 20, 2014 2014).
5. J. J. P. Stewart, Mopac2016, Version: 17.1731.
6. Rdkit: Open Source Cheminformatic Software (http[://]www.rdkit.org/).
7. M. R. Gerhardt, L. Tong, R. Gómez-Bombarelli, Q. Chen, M. P. Marshak, C. J. Galvin, A. Aspuru-Guzik, R. G. Gordon, and M. J. Aziz, "Anthraquinone Derivatives in Aqueous Flow Batteries", *Advanced Energy Materials* 1601488 (2017).
8. M. -A. Goulet and M. J. Aziz, "Flow Battery Molecular Reactant Stability Determined by Symmetric Cell Cycling Methods", J. Electrochem. Soc. 165, in press (2018).
9. B. Yang, L. Hoober-Burkhardt, S. Krishnamoorthy, A. Murali, G. K. S. Prakash, and S. R. Narayanan, "High-Performance Aqueous Organic Flow Battery with Quinone-Based Redox Couples at Both Electrodes", *Journal of The Electrochemical Society* 163, A1442 (2016).
10. A. Khataee, K. Wedege, E. Drazevic, and A. Bentien, "Differential pH as a Method for Increasing Cell Potential in Organic Aqueous Flow Batteries", Journal of Materials Chemistry A (2017).
11. M. R. Gerhardt, L. Tong, R. Gómez-Bombarelli, Q. Chen, M. P. Marshak, C. J. Galvin, A. Aspuru-Guzik, R. G. Gordon, and M. J. Aziz, "Anthraquinone Derivatives in Aqueous Flow Batteries", *Advanced Energy Materials* 1601488 (2017).
12. R. Chen and R. Hempelmann, "Ionic Liquid-Mediated Aqueous Redox Flow Batteries for High Voltage Applications", Electrochemistry Communications 70, 56 (2016).
13. R. Darling, K. Gallagher, W. Xie, L. Su, and F. Brushett, "Transport Property Requirements for Flow Battery Separators", *Journal of The Electrochemical Society* 163, A5029 (2015).
14. J. Luo, A. Sam, Hu, C. DeBruler, X. Wei, W. Wang, and T. L. Liu, "Unraveling pH Dependent Cycling Stability of Ferricyanide/Ferrocyanide in Redox Flow Batteries", *Nano Energy* (2017).
15. S. Y. Reece, "Metal Complexes of Substituted Catecholates and Redox Flow Batteries Containing the Same", United States Patent (2016).
16. K. Lin, R. Gómez-Bombarelli, E. S. Beh, L. Tong, Q. Chen, A. Valle, A. Aspuru-Guzik, M. J. Aziz, and R. G. Gordon, "A Redox-Flow Battery with an Alloxazine-Based Organic Electrolyte", *Nature Energy* 1, 16102 (2016).
17. K. Lin, Q. Chen, M. R. Gerhardt, L. Tong, S. B. Kim, L. Eisenach, A. W. Valle, D. Hardee, R. G. Gordon, M. J. Aziz, and M. P. Marshak, "Alkaline Quinone Flow Battery", *Science* 349, 1529 (2015).
18. C. Costentin, "Electrochemical Approach to the Mechanistic Study of Proton-Coupled Electron Transfer", *Chem. Rev.* 108, 2145 (2008).
19. M. T. Huynh, C. W. Anson, A. C. Cavell, S. S. Stahl, and S. Hammes-Schiffer, "Quinone 1 e⁻ and 2 e−/2 H⁺ Reduction Potentials: Identification and Analysis of Deviations from Systematic Scaling Relationships", *J Am Chem Soc* 138, 15903 (2016).
20. S. Er, C. Suh, M. P. Marshak, and A. Aspuru-Guzik, "Computational Design of Molecules for anAll-Quinone Redox Flow Battery", *Chem. Sci.* 6, 885 (2015).
21. Kwabi, D. G.; Lin, K.; Ji, Y.; Kerr, E. F.; Goulet, M.-A.; De Porcellinis, D.; Tabor, D. P.; Pollack, D. A.; Aspuru-Guzik, A.; Gordon, R. G.; Aziz, M. J., Alkaline Quinone Flow Battery with Long Lifetime at pH 12. *Joule* 2018.
22. Goulet, M. -A.; Aziz, M. J., Flow Battery Molecular Reactant Stability Determined by Symmetric Cell Cycling Methods. *J. Electrochem. Soc.* 2018, 165, in press.
23. S. Y. Reece, "Metal Complexes of Substituted Catecholates and Redox Flow Batteries Containing the Same", United States Patent (2016).
24. V. Dieterich, J. Milshtein, J. Barton, T. Carney, R. Darling, and F. Brushett, "Estimating the Cost of Organic Battery Active Materials: A Case Study on Anthraquinone Disulfonic Acid", Translational Materials Research in press, (2018).
25. Beh, E. S.; De Porcellinis, D.; Gracia, R. L.; Xia, K. T.; Gordon, R. G.; Aziz, M. J., A Neutral pH Aqueous Organic—Organometallic Redox Flow Battery with Extremely High Capacity Retention. *ACS Energy Letters* 2017, 639-644.

Other embodiments are described in the claims.

What is claimed is:

1. A redox flow battery comprising:
a first aqueous electrolyte comprising a first redox active material; and
a second aqueous electrolyte comprising a second redox active material that is a compound of formula I:

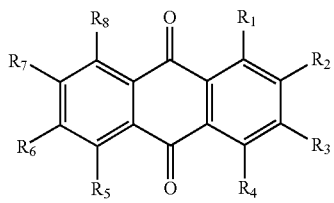

or an ion, salt, or hydroquinone thereof,
wherein each of $R_1$-$R_8$ is independently H; halo; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo; $-NO_2$; $-OR_a$; $-N(R_a)_2$; $-C(=O)R_a$; $-C(=O)OR_a$; $-S(=O)_2R_a$; $-S(=O)_2OR_a$; $-OS(=O)_2OR_a$; $-P(=O)R_{a2}$; $-P(=O)(OR_a)_2$; and $-OP(=O)(OR_a)_2$; $-X_1$-$L_1$-C(O)O-$Y_1$; $-X_2$-$L_2$-C(O)O-$Y_2$; $-X_3$-$L_3$-P(=O)(OY_3)_2$; or $-X_4$-$L_4$-P(=O)(OY_4)_2$;

wherein each $R_a$ is independently H; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; or optionally substituted $C_{1-9}$ heteroaryl having one to four heteroatoms independently selected from O, N, and S;

$X_1$, $X_2$, $X_3$, and $X_4$ are independently O, S, or $CH_2$; $L_1$, $L_2$, $L_3$, and $L_4$ are independently $C_1$-$C_6$ alkylene; and $Y_1$, $Y_2$, $Y_3$, and $Y_4$ are independently H or optionally substituted $C_1$-$C_6$ alkyl, provided that one and only one of $R_1$-$R_8$ is $-X_1$-$L_1$-C(O)O-$Y_1$ or $-X_3$-$L_3$-P(=O)(OY_3)_2$ and one and only one of $R_1$-$R_8$ is $-X_2$-$L_2$-C(O)O-$Y_2$ or $-X_4$-$L_4$-P(=O)(OY_4)_2$.

2. The battery of claim 1, wherein $X_1$ and $X_2$ are O, and/or wherein each of $R_1$-$R_8$ is independently H; halo; optionally substituted $C_{1-6}$ alkyl; $-X_1$-$L_1$-C(O)O-$Y_1$; or $-X_2$-$L_2$-C(O)O-$Y_2$, provided $R_2$ is $-X_1$-$L_1$-C(O)O-$Y_1$ or $-X_2$-$L_2$-C(O)O-$Y_2$, and/or wherein $R_2$ is $-X_1$-$L_1$-C(O)O-$Y_1$ and $R_6$ is $-X_2$-$L_2$-C(O)O-$Y_2$, and/or
wherein $Y_1$ and $Y_2$ are H.

3. The battery of claim 1, wherein $X_3$ and $X_4$ are O, and/or wherein each of $R_1$-$R_8$ is independently H; halo; optionally substituted $C_{1-6}$ alkyl; $-X_3$-$L_3$-P(=O)(OY_3)_2$; or $-X_4$-$L_4$-P(=O)(OY_4)_2$, provided $R_2$ is $-X_3$-$L_3$-(=O)(OY_3)_2$, or $-X_4$-$L_4$-P(=O)(OY_4)_2$, and/or wherein $R_2$ is $-X_3$-$L_3$-P(=O)(OY_3)_2$ and $R_6$ is $-X_4$-$L_4$-P(=O)(OY_4)_2$, and/or
wherein $Y_3$ and $Y_4$ are H.

4. The battery of claim 1, wherein the compound of formula I is

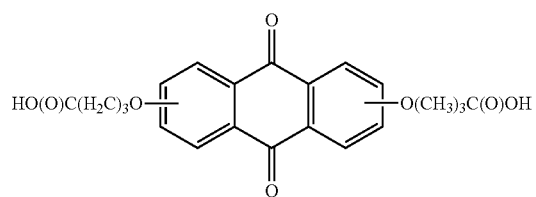

or an ion, salt, or
hydroquinone thereof; wherein $R_2$ is $-O(CH_2)_3C(O)OH$.

5. The battery of claim 1, wherein the compound of formula I is

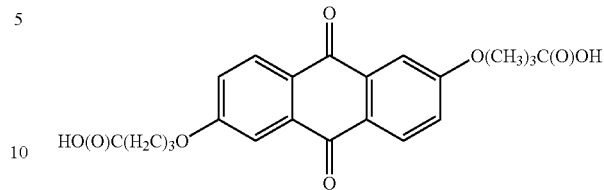

or an ion, salt, or hydroquinone thereof.

6. The battery of claim 1, wherein the compound of formula I is

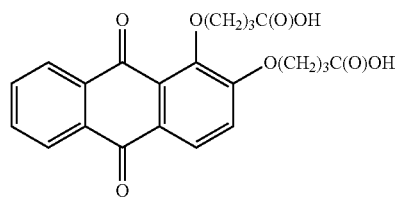

or an ion, salt, or hydroquinone thereof.

7. The battery of claim 1, wherein the compound of formula I is

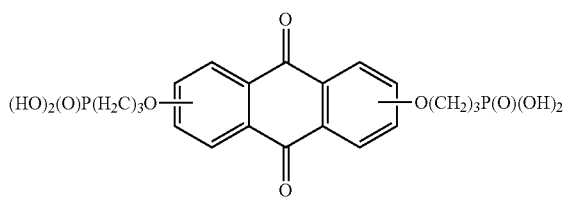

or an ion, salt, or hydroquinone thereof; wherein $R_2$ is $-O(CH_2)_3P(O)(OH)_2$.

8. The battery of claim 1, wherein the compound of formula I is

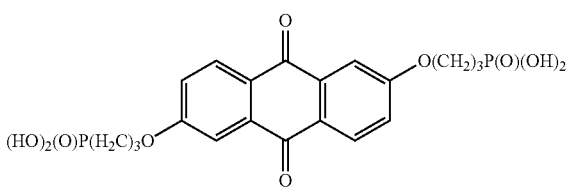

or an ion, salt, or hydroquinone thereof.

9. The battery of claim 1, wherein the second redox active material is the hydroquinone of formula I, which is oxidized to the corresponding quinone during discharge, and/or wherein the pH of the second aqueous electrolyte is ≥7, and/or wherein the first redox active material comprises bromine, chlorine, iodine, oxygen, vanadium, chromium, cobalt, iron, aluminum, manganese, cobalt, nickel, copper, or lead.

10. The battery of claim 9, wherein the pH is from 8 to 13.

11. A compound of formula I:

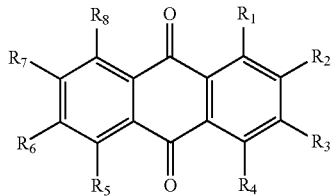

or an ion, salt, or hydroquinone thereof, wherein each of $R_1$-$R_8$ is independently H; halo; optionally substituted $C_{1-6}$ alkyl; optionally substituted $C_{3-10}$ carbocyclyl; optionally substituted $C_{1-9}$ heterocyclyl having one to four heteroatoms independently selected from O, N, and S; optionally substituted $C_{6-20}$ aryl; optionally substituted $C_{1-9}$ heteroaryl having one to four heteroatoms independently selected from O, N, and S; oxo; —$NO_2$; —$OR_a$; —$N(R_a)_2$; —$C(=O)R_a$; —$C(=O)OR_a$; —$S(=O)_2R_a$; —$S(=O)_2OR_a$; —$OS(=O)_2OR_a$; —$P(=O)R_{a2}$; —$P(=O)(OR_a)_2$; and —$OP(=O)(OR_a)_2$; —$X_1$-$L_1$-C(O)O—$Y_1$; —$X_2$-$L_2$-C(O)O—$Y_2$; —$X_3$-$L_3$-P(=O)(OY_3)_2$; or —$X_4$-$L_4$-P(=O)(OY_4)_2$; provided $R_2$ is —$X_1$-$L_1$-C(O)O—$Y_1$, —$X_2$-$L_2$-C(O)O—$Y_2$, —$X_3$-$L_3$-P(=O)(OY_3)_2$, or —$X_4$-$L_4$-P(=O)(OY_4)_2$;

wherein each $R_a$ is independently H; optionally substituted $C_{1-6}$ alkyl; optionally substituted $C_{3-10}$ carbocyclyl;

optionally substituted $C_{1-9}$ heterocyclyl having one to four heteroatoms independently selected from O, N, and S; optionally substituted $C_{6-20}$ aryl; or optionally substituted $C_{1-9}$ heteroaryl having one to four heteroatoms independently selected from O, N, and S;

$X_1$, $X_2$, $X_3$, and $X_4$ are independently O, S, or $CH_2$; $L_1$, $L_2$, $L_3$, and $L_4$ are independently $C_1$-$C_6$ alkylene; and $Y_1$, $Y_2$, $Y_3$, and $Y_4$ are independently H or optionally substituted $C_1$-$C_6$ alkyl, provided that one and only one of $R_1$-$R_8$ is —$X_1$-$L_1$-C(O)O—$Y_1$ or —$X_3$-$L_3$-P(=O)(OY_3)_2$ and one and only one of $R_1$-$R_8$ is —$X_2$-$L_2$-C(O)O—$Y_2$ or —$X_4$-$L_4$-P(=O)(OY_4)_2$, and provided that:

ii. when $R_4$-$R_8$ are H and $R_2$, $R_3$, $R_6$, and $R_7$ are —$O(CH_2)_3(CH_3)$, $R_1$ and $R_5$ are not both —$O(CH_2)_3C(O)OH$;

iii. when $R_4$ and $R_8$ are H and $R_2$, $R_3$, $R_6$, and $R_7$ are —$O(CH_2)_4(CH_3)$, $R_1$ and $R_5$ are not both —$O(CH_2)_4C(O)OH$;

iv. when $R_1$ and $R_8$ are OH and $R_3$-$R_6$ are H, $R_2$ and $R_7$ are not both —$(CH_2)_3C(O)OH$ or —$(CH_2)_3C(O)OCH_3$;

v. when $R_1$, $R_4$, $R_5$, and $R_8$ are $NH_2$ and $R_3$ and $R_6$ are H, $R_2$ and $R_7$ are not both —$O(CH_2)_3C(O)O(CH_2)_4CH_3$;

vi. when $R_1$, $R_3$-$R_5$, $R_7$, and $R_8$ are H, $R_2$ and $R_6$ are not both —$OCH(CH_3)C(O)OCH_3$, —$OCH(CH_3)C(O)OH$, or —$OCH_2C(O)OCH_3$;

vii. when $R_1$, $R_3$, $R_5$, and $R_7$ are H, and $R_4$ and $R_8$ are —$N(R_a)_2$, $R_2$ and $R_6$ are not both —$S(CH_2)_nC(O)OCH_2CH_3$, wherein n is 1 to 5;

viii. when $R_1$ and $R_4$ are $OCH_3$, and $R_5$-$R_8$ are H, $R_2$ and $R_3$ are not both —$CH_2CH_2C(O)OH$, —$CH_2CH_2C(O)OCH_3$, or —$CH_2CH(C(O)CH_3)C(O)OCH_2CH_3$;

ix. when $R_1$ and $R_4$ are OH, and $R_5$-$R_8$ are H, $R_2$ and $R_3$ are not both —$CH_2CH_2C(O)OCH_3$;

x. when $R_1$ and $R_4$-$R_8$ are H, $R_2$ and $R_3$ are not both —$CH_2C(NHC(O)CH_3)(C(O)OCH_2CH_3)_2$ or —$CH_2CH(NHC(O)CH_3)C(O)OCH_2CH_3$;

xv. when $R_3$-$R_7$ are H and $R_1$ is $NH_2$, $R_2$ and $R_8$ are not both —$SCH_2C(O)OH$;

xvi. when $R_3$-$R_8$ are H, $R_1$ and $R_2$ are not both —$OC(O)CH_2CH_2C(O)O$ $CH_2CH_3$;

xvii. when $R_1$, $R_3$-$R_5$, $R_7$, and $R_8$ are H, $R_2$ and $R_6$ are not both —$OC(O)CH_2CH_2C(O)OCH_2CH_3$;

xx. when $R_2$, $R_3$, $R_6$, and $R_7$ are H and $R_4$ and $R_5$ are —$(CH_2)_5CH_3$, $R_1$ and $R_8$ are not both —$(CH_2)_7C(O)OH$;

xxii. when $R_3$ and $R_6$ are H and $R_1$, $R_4$, $R_5$, and $R_8$ are —$NH_2$, $R_2$ and $R7_5$ are not both —$O(CH_2)_3C(O)OCH_3$.

12. The compound of claim 11, wherein $X_1$ and $X_2$ are O, and/or wherein each of $R_1$-$R_8$ is independently H; halo; optionally substituted $C_{1-6}$ alkyl; —$X_1$-$L_1$-C(O)O—$Y_1$; or —$X_2$-$L_2$-C(O)O—$Y_2$, provided $R_2$ is —$X_1$-$L_1$-C(O)O—$Y_1$ or —$X_2$-$L_2$-C(O)O—$Y_2$, and/or wherein $R_2$ is —$X_1$-$L_1$-C(O)O—$Y_1$ and $R_6$ is —$X_2$-$L_2$-C(O)O—$Y_2$, and/or wherein $Y_1$ and $Y_2$ are H.

13. The compound of claim 11, wherein $X_3$ and $X_4$ are O, and/or wherein each of $R_1$-$R_8$ is independently H; halo; optionally substituted $C_{1-6}$ alkyl; —$X_3$-$L_3$-P(=O)(OY_3)_2$; or —$X_4$-$L_4$-P(=O)(OY_4)_2$, provided $R_2$ is —$X_3$-$L_3$-P(=O)(OY_3)_2$, or —$X_4$-$L_4$-P(=O)(OY_4)_2$, and/or wherein $R_2$ is —$X_3$-$L_3$-P(=O)(OY_3)_2$ and $R_6$ is —$X_4$-$L_4$-P(=O)(OY_4)_2$, and/or wherein $Y_3$ and $Y_4$ are H.

14. The compound of claim 11, wherein the compound of formula I is

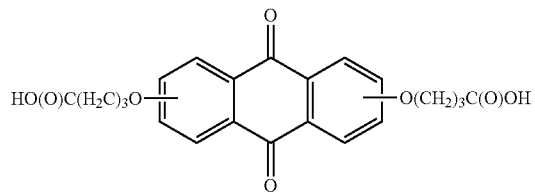

or an ion, salt, or hydroquinone thereof; wherein $R_2$ is —$O(CH_2)_3C(O)OH$.

15. The compound of claim 11, wherein the compound of formula I is

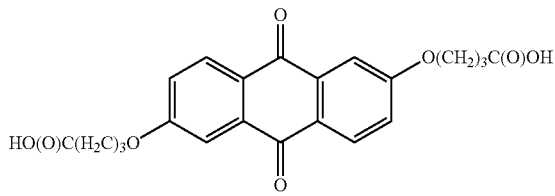

or a salt, ion, or hydroquinone thereof.

16. The compound of claim 11, wherein the compound of formula I is

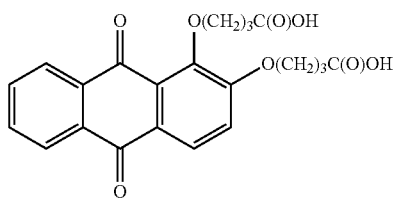
or an ion, salt, or hydroquinone thereof.
17. The compound of claim 11, wherein the compound of formula I is:
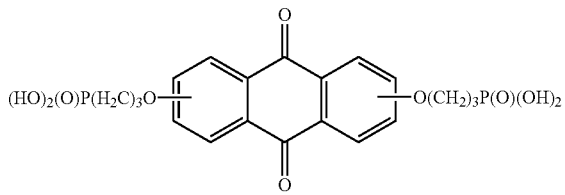
or an ion, salt, or hydroquinone thereof; wherein $R_2$ is —O(CH$_2$)$_3$P(O)(OH)$_2$.
18. The compound of claim 11, wherein the compound of formula 1 is:
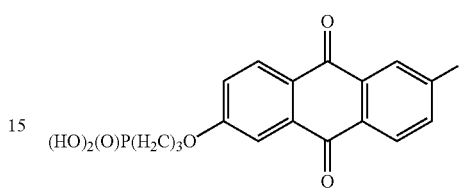
or an ion, salt, or hydroquinone thereof.
* * * * *

UNITED STATES PATENT AND TRADEMARK OFFICE
CERTIFICATE OF CORRECTION

PATENT NO. : 11,724,980 B2
APPLICATION NO. : 16/968684
DATED : August 15, 2023
INVENTOR(S) : Michael J. Aziz et al.

Page 1 of 1

It is certified that error appears in the above-identified patent and that said Letters Patent is hereby corrected as shown below:

In the Claims

Column 39, Claim 3, Lines 48-49, replace "-$X_3$-$L_3$-(=O)(O$Y_3$)$_2$" with --$X_3$-$L_3$-P(=O)(O$Y_3$)$_2$--.

Column 41, Claim 11, Line 46, replace "$R_4$-$R_8$" with --$R_4$ and $R_8$--.

Signed and Sealed this
Fifteenth Day of April, 2025

Coke Morgan Stewart
*Acting Director of the United States Patent and Trademark Office*